(12) United States Patent
Kim et al.

(10) Patent No.: US 9,527,886 B2
(45) Date of Patent: Dec. 27, 2016

(54) AMPHIPATHIC PEPTIDE-LIPASE CONJUGATE HAVING ADVANCED LIPASE ACTIVITY AND USE THEREOF

(75) Inventors: Sun-Chang Kim, Daejeon (KR); Bong Hyun Sung, Daejeon (KR); Kyung Seok Yang, Daejeon (KR); Jun Hyoung Lee, Daejeon (KR); Ki Jung Lim, Daejeon (KR); Myung Keun Park, Daejeon (KR)

(73) Assignees: KOREA ADVANCED INSTITUTE OF SCIENCE AND TECHNOLOGY, Daejeon (KR); INTELLIGENT SYNTHETIC BIOLOGY CENTER, Daejeon (KR)

( * ) Notice: Subject to any disclaimer, the term of this patent is extended or adjusted under 35 U.S.C. 154(b) by 0 days.

(21) Appl. No.: 14/123,513

(22) PCT Filed: Aug. 10, 2012

(86) PCT No.: PCT/KR2012/006412
§ 371 (c)(1),
(2), (4) Date: Jan. 24, 2014

(87) PCT Pub. No.: WO2013/022320
PCT Pub. Date: Feb. 14, 2013

(65) Prior Publication Data
US 2014/0162331 A1 Jun. 12, 2014

(30) Foreign Application Priority Data
Aug. 10, 2011 (KR) ........................ 10-2011-0079609

(51) Int. Cl.
| | |
|---|---|
| *C12N 9/12* | (2006.01) |
| *C07K 7/06* | (2006.01) |
| *C07K 7/08* | (2006.01) |
| *C07K 14/47* | (2006.01) |
| *C12N 9/20* | (2006.01) |
| *C07K 14/46* | (2006.01) |
| *C07K 14/00* | (2006.01) |
| *C12P 7/64* | (2006.01) |

(52) U.S. Cl.
CPC . *C07K 7/06* (2013.01); *C07K 7/08* (2013.01); *C07K 14/001* (2013.01); *C07K 14/463* (2013.01); *C07K 14/47* (2013.01); *C07K 14/4723* (2013.01); *C12N 9/20* (2013.01); *C12P 7/649* (2013.01); *C12Y 301/01003* (2013.01); *C07K 2319/00* (2013.01); *C07K 2319/21* (2013.01)

(58) Field of Classification Search
None
See application file for complete search history.

(56) References Cited

FOREIGN PATENT DOCUMENTS

| | | | |
|---|---|---|---|
| JP | 2002501079 A | | 1/2002 |
| KR | 10-0836596 | * | 6/2008 |
| KR | 100836596 B1 | | 6/2008 |
| WO | 99/48912 A1 | | 9/1999 |
| WO | 2009/129263 A1 | | 10/2009 |
| WO | 2011/066511 A1 | | 6/2011 |

OTHER PUBLICATIONS

Yang et al. J. Biosien. Bioengin. (2009) 107 (6) 599-604.*
Ryu et al. Appl. Microbiol. Biotechnol. (2006) 70, 321-326.*
English translation of Korean Patent 10-0836596.*
Xing et al. Microbial Cell Factories (Apr. 2011) 10, 42.*
Hughes et al., "Production of *Candida antarctica* lipase B gene open reading frame using automated PCR gene assembly protocol on robotic workcell and expression in an ethanologenic yeast for use as resin-bound biocatalyst in biodiesel production," J. of Laboratory Automation, vol. 16, No. 1, pp. 17-37, Feb. 2011.
Lee, Hyun Ji, International Search Report and Written Opinion, Korean Intellectual Property Office, PCT/KR2012/006412, Feb. 27, 2013.
Lee, J. H. et al., "Enhanced expression of tandem multimers of the antimicrobial peptide buforin II in *Escherichia coli* by the DEAD-box protein and trxB mutant," Applied Microbiology and Biotechnology. May 2002 , vol. 58 , No. 6 , pp. 790-796.
Lee, J. H. et al., "Acidic Peptide-Mediated Expression of the Antimicrobial Peptide Buforin II as Tandem Repeats in *Escherichia coli*," Protein Expression and Purification. Feb. 1998 , vol. 12 , No. 1, pp. 53-60.
Jang, J. H. et al., "Enhancement of the cancer targeting specificity of buforin IIb by fusion with an anionic peptide via a matrix metalloproteinases-cleavable linker," Peptides. May 2011 , vol. 32 , No. 5, pp. 895-899.
Akoh, C. C. et al., "Enzymatic Approach to Biodiesel Production," Journal of Agricultural and Food Chemistry. Oct. 2007 , vol. 55 , No. 22 , pp. 8995-9005.
Xing et al., "Streamlined protein expression and purification using cleavable self-aggregating tags," Microbial Cell Factories, vol. 10, No. 1, pp. 42, Jun. 2, 2011.
Wu et al., "Active protein aggregates induced by terminally attached self-assembling peptide ELK16 in *Escherichi coli*," Microbial Cell Factories, vol. 10, No. 1, pp. 9, Feb. 15, 2011.
Tudor, Mark, Extended European Search Report, Euopean Patent Office, EP 12822946, Feb. 27, 2015.
Shibahara Naoji, Japanese Office Action, Japanese Intellectual Patent Office, JP Application No. 2014-523877, Apr. 13, 2015.
Decision to Grant a Patent, KR Pat. Appl. No. 10-2012-0088042, Korean Intellectual Property Office, Sep. 26, 2016.

* cited by examiner

*Primary Examiner* — Nashaat Nashed
(74) *Attorney, Agent, or Firm* — Joseph R. Baker, Jr.; Gavrilovich, Dodd & Lindsey LLP

(57) ABSTRACT

Disclosed are an amphipathic peptide-lipase conjugate with enhanced lipase activity, a polynucleotide coding for the conjugate, an expression vector carrying the polynucleotide, a transformant anchoring the expression vector therein, a method for preparing the conjugate, a lipolysis method using the conjugate, and a method for producing biodiesel using the lipase.

12 Claims, 10 Drawing Sheets

Figure 8
Wild type M37
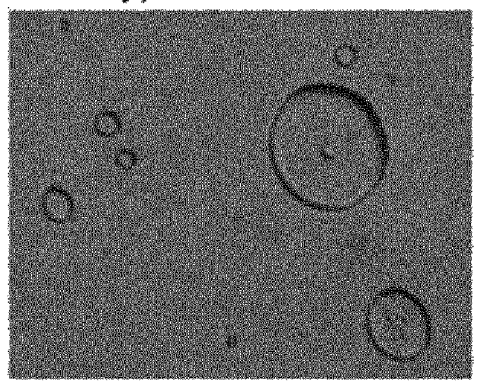 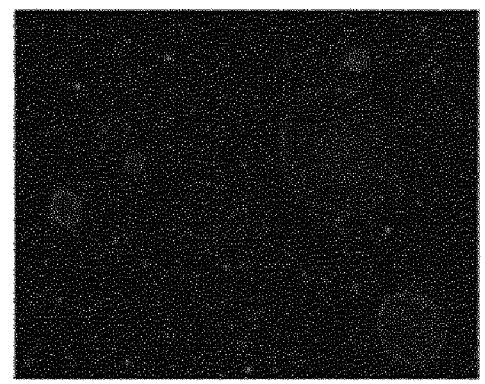
NKC-fused M37
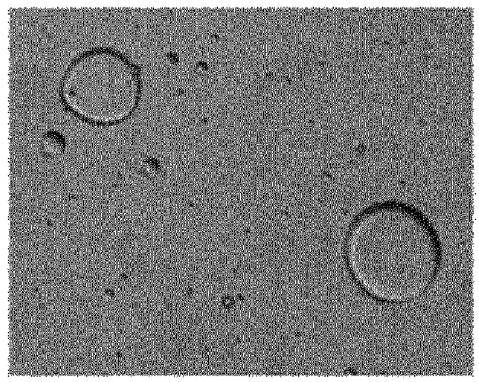 

Figure 9
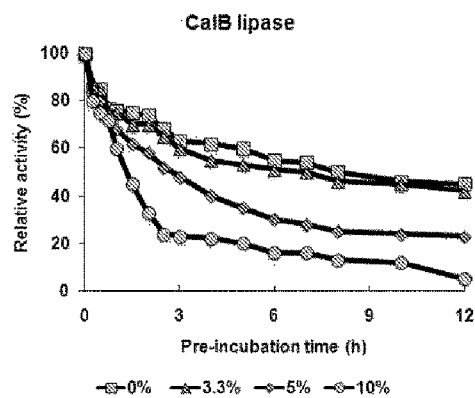
a. CalB lipase
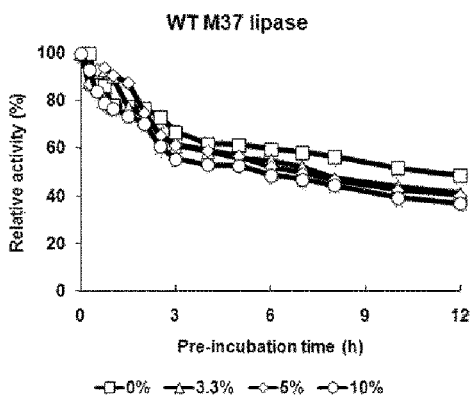
b. WT M37 lipase
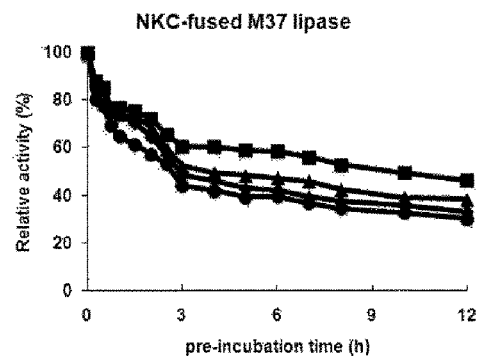
c. NKC-fused M37 lipase

AMPHIPATHIC PEPTIDE-LIPASE CONJUGATE HAVING ADVANCED LIPASE ACTIVITY AND USE THEREOF

CROSS REFERENCE TO RELATED APPLICATIONS

This application is a U.S. National Stage Application filed under 35 U.S.C. §371 and claims priority to International Application No. PCT/KR2012/006412, filed Aug. 10, 2012, which application claims priority under 35 U.S.C. §119 to Korean Application No. 10-2011-0079609, filed Aug. 10, 2011, the disclosures of which are incorporated herein by reference.

TECHNICAL FIELD

The present invention relates to an amphipathic peptide-lipase conjugate with advanced lipase activity, a polynucleotide coding for the conjugate, an expression vector comprising the polynucleotide, a transformant anchoring the expression vector therein, a method for constructing the conjugate, a lipolysis method using the conjugate, and a method for producing biodiesel using the lipase.

BACKGROUND ART

Lipase (triacylglycerol acylhydrolase, EC3.1.1.3) is an enzyme that catalyzes the hydrolysis of triglycerides into fatty acids and glycerides or glycerols and performs an essential role as one of the three digestive enzymes, together with amylase and protease, which digest foods. Lipases are naturally sourced from a broad range of organisms including animals, plants and microbes.

In addition to playing important roles in lipid metabolism in vivo, lipases are useful for enhancing the flavor of cheese, increasing free fatty acids upon vegetable fermentation, deepening the flavor upon meat fermentation, and lipolyzing fish. Further, the use of lipases has now extended to the synthesis of expensive, optically pure isomers. Moreover, lipases find application in a variety of industries. As some examples thereof, the applications of lipases in the dairy industry include making cheese via the hydrolysis of milk fats and the lysis of butterfat or cream. In the detergent industry, lipases can be used to prepare laundry detergents or washing machine detergents. The enzymes can reduce the environmental load of detergent products since they save energy by enabling a lower wash temperature to be used. The scope of application of lipases in the oleochemical industry is enormous, including the manufacture of unsaturated fatty acids and soaps and the production of cocoa butter from cheap palm oil. In the paper manufacturing industry, lipases are utilized to remove resins or rosins from woods and ink from waste paper. Turning to the pharmaceutical industry, the use of lipases includes the synthesis of separate R- and S-optical isomers, the separation of racemates and the manufacture of drugs. The cosmetic industry applies lipases to the production of skin cosmetics including waxes, suntan creams, and bath products. Also, lipases are useful in the energy industry as a means for producing biodiesel from vegetable oil.

Currently, biodiesel, emerging as new renewable energy, has been produced using chemical catalyst-based methods throughout the world. However, their commercialization has not yet been successful because of the use of a large amount of organic solvents, the high expense of environmental disposal, and high energy consumption attributed to high reaction temperature. For these reasons, intensive attention is paid to processes employing lipase as a catalyst. These processes enjoy the advantage of saving energy thanks to low reaction temperatures, reducing the production cost by creating profits from the by-product glycerol, and being almost free of environmental pollution. However, the enzyme is poor in terms of stability and efficiency vs. cost. The immobilization of the enzyme has been suggested as a way to overcome the drawbacks, but remains distant as a solution to the problem of how to improve enzyme properties. Thus, active research is being done to improve the industrial utility of the enzyme by increasing its enzymatic activity.

Rather than the development of inexpensive and potent lipases, for example, indirect alternatives, such as modified reaction conditions for lipases and enzyme immobilization, have been used to solve the problems associated with lipases. Alternatively, searching for new lipases using metagenomics has been done, but has had no noteworthy achievements. In order to improve the activity of lipases and their substrate specificity, thermal resistance and stability, extensive studies have been done into which the X-ray crystallographic data of various lipases have been collected and the lipases have been modified in such a manner that amino acid residues of the active site and the surrounding area are substituted using protein engineering techniques such as site-directed mutagenesis. Although this brings about an improvement in the activity of lipases, the improvement is only partial.

DISCLOSURE

Technical Problem

Given this background, the present inventors conceived that the low accessibility of lipases to their substrates is due to the poor solubility of the substrates, and discovered that a lipase, when associated with an amphipathic peptide, that is, a peptide having both hydrophilic and hydrophobic moieties, is improved in accessibility, bindability and reactivity to its substrates which has led to the present invention.

Technical Solution

It is therefore an object of the present invention to provide an amphipathic peptide-lipase conjugate which exhibits higher lipase activity than does lipase alone.

It is another object of the present invention to provide a polynucleotide encoding the conjugate, an expression vector comprising the polynucleotide, and a transformant comprising the expression vector therein.

It is a further object of the present invention to provide a method for preparing the amphipathic peptide-lipase conjugate.

It is still a further object of the present invention to provide a lipolysis method using the amphipathic peptide-lipase conjugate.

It is still another object of the present invention to provide a method for producing biodiesel using the amphipathic peptide-lipase conjugate.

Advantageous Effects

Being significantly improved in reactivity to lipid substrates and thus in enzymatic activity, the lipases conjugated with amphipathic peptides in accordance with the present invention, even if used in a small amount, guarantee a sufficient lipid conversion rate in fields that require lipase, such as biodiesel production. In addition, the lipase conjugates of the present invention do not require the use of additional surfactants, thus providing an economical benefit.

DESCRIPTION OF DRAWINGS

The above and other objects, features and other advantages of the present invention will be more clearly understood from the following detailed description taken in conjunction with the accompanying drawings, in which:

FIG. 8 shows the localization of the NKC-fused M37 lipase to lipid particles using fluorescence microscopy;

FIG. 9 shows enzyme activities of the *Candida antarctica* lipase B (A), wild-type M37 lipase (B) and NKC-fused M37 lipase (C), measured at predetermined times with 12 h of incubation at 40° C. The hydrolytic activities of the *Candida antarctica* lipase B, wild-type M37 and NKC-fused M37 lipase were measured in 0%, 3.3%, 5%, and 10% methanol-aqueous solutions.

BEST MODE

Figure 1:
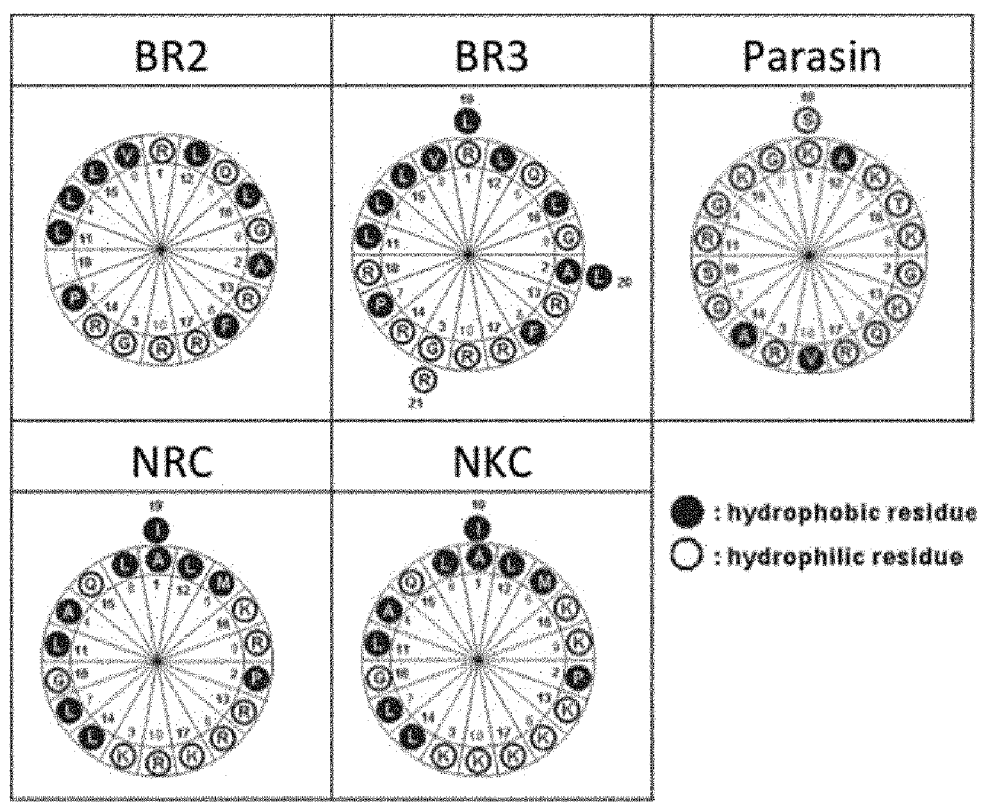
FIG. 1 shows diagrams of the Schiffer-Edmundson wheel projection of amphipathic peptides where No. 1 represents residue 1 of the peptides and filled circles and open circles indicate hydrophobic and hydrophilic amino acids, respectively.

In accordance with an aspect thereof, the present invention provides an amphipathic peptide-lipase conjugate in which a lipase is conjugated with an amphipathic peptide.

The term "amphipathic peptide," as used herein, refers to a peptide that comprises polar amino acids on the polar face and non-polar amino acids on the no-polar face. Included among the polar amino acid residues are cysteine, glutamine, threonine, tyrosine, serine and asparagine while examples of the non-polar amino acid residues include phenylalanine, tryptophane, methionine, proline, valine, isoleucine, leucine, glycine and alanine. In the present invention, the amphipathic peptide serves as a medium for enhancing the binding and reactivity of the lipase to its substrate lipids. In the amphipathic peptide, the polar amino acid residues or the non-polar amino acid residues may be present in close proximity in the amino acid sequence. Alternatively, the amino acid residues may be distributed randomly irrespective of their polarity on the amino acid sequence, but become positioned spatially close to each other because of the effects that polarity has on the three dimensional structure, forming a polar face and a non-polar face.

As long as it can conjugate to a lipase and improve the accessibility or reactivity of the enzyme to the substrate, any amphipathic peptide may be used for the purpose of the present invention. Examples of the amphipathic peptide include Buforin IIb (SEQ ID NO: 1), B0 (SEQ ID NO: 2), Paracin I (SEQ ID NO: 3), NKC (SEQ ID NO: 4), and NRC (SEQ ID NO: 5), but are not limited thereto. In addition, no particular limitations are imparted to the length of the amphipathic peptide if it can act to enhance accessibility and reactivity to the substrate of the lipase to which it is conjugated. In a preferred embodiment, buforin IIb, B0, paracin I, NKC and NRC were employed.

As mentioned above, the amphipathic peptide useful in the present invention may be a peptide comprising an amino acid sequence selected from the group consisting of SEQ ID NO: 1 to 5. In addition, peptides comprising at least 70%, preferably at least 80%, more preferably at least 90%, more preferably at least 95%, and most preferably at least 98% homology to the amino acid sequence with SEQ ID NO: 1 to 5 may be employed as amphipathic peptides in the present invention provided that they retain the biological function of substantially enhancing lipase activity. It is appreciated that peptide variants, even if mutated in part by deletion, modification, substitution or addition, fall within the scope of the present invention as long as they exhibit biological activity that is identical to or corresponds to the amphipathic peptides.

As used herein, the term "lipase" refers to an enzyme that catalyzes the hydrolysis of fat. In detail, when acting on neutral fats, lipases are responsible for the degradation of triacyglycerides into diacyglycerides and the degradation of monoacylglycerides into fatty acids and glycerine. On the whole, lipases are abundantly found in the pancreatic fistula in animals while plants contain lipases in seeds such as wheat, castor bean, beans, etc. If it has the biological activity of hydrolyzing lipids, any type of lipase may be used in the present invention, without limitation. For instance, the lipase TliA (thermostable lipase), derived from *Pseudomonas fluorescens*, or the lipase M37, derived from *Photobacterium lipolyticum* may be used. Information about lipases may be obtained from a known database, such as GenBank, NIH. For example, TliA and M37 may be searched for with the accession numbers of AAD09856 and AAS78630, respectively. TliA and M37 may be lipases comprising, but not limited to, the amino acid sequences of SEQ ID NO: 6 and 7, respectively. Also useful in the present invention, as discussed above, are proteins having at least 70%, preferably at least 80%, more preferably at least 90%, more preferable still at least 95%, and most preferably at least 98% homology to the amino acid sequence with SEQ ID NO: 6 or 7 provided that they have a substantial biological activity to degrade lipids. Furthermore, it is appreciated that peptide variants, even if mutated in part by deletion, modification, substitution or addition, fall within the scope of the present invention as long as they exhibit biological activity identical or corresponding to the amphipathic peptides.

As used herein, the term "amphipathic peptide-lipase conjugate" refers to an amphipathic peptide that is coupled to a lipase in such a manner as not to compromise the biological activity of the lipase. In the amphipathic peptide-lipase conjugate, the amphipathic peptide is coupled to the lipase chemically, enzymatically or by genetic manipulation to form a fusion protein.

The amphipathic peptide may be coupled directly or via a linker to the lipase.

As used herein, the term "linker" refers to any moiety which connects two different fusion partners (e.g., biological polymers) by use of a hydrogen bond, electrostatic interaction, van der waals force, a disulfide bond, a salt bridge, hydrophobic interaction, a covalent bond, etc. In a preferred embodiment, the linker has at least one cysteine residue which can participate in at least one disulfide bond under physiological conditions or other standard peptide conditions (e.g., conditions for purifying or storing peptides). In addition to connecting the fusion partners, the linker may serve as a spacer and provide a space between the fusion partners or as a hinge to provide flexibility or rigidity for the conjugate. The linker may be a peptidyl linker or a non-peptidyl linker. Direct connection between the fusion partners via a peptide bond or a disulfide bond is within the scope of the role of the linker.

The term "non-peptidyl linker," as used herein, refers to a biocompatible linker consisting of at least two repeating units with a non-peptidyl covalent bond between the repeating units.

Examples of the non-peptidyl linker useful in the present invention include polyethylene glycol (PEG) homopolymers, polypropylene glycol homopolymers, ethylene glycol-propylene glycol copolymers, polyoxyethylated polyol, polyvinyl alcohols, polysaccharides, dextran, polyvinyl ethyl ether, biodegradable polymers, lipid polymers, chitins, hyarulinic acid and a combination thereof, with a preference for polyethylene glycol homopolymers. Their derivatives that have already been known in the art or can be readily prepared on the technical level of the art are within the scope of the present invention. More preferably, the polyethylene glycol homopolymer is in a bifunctional aldehyde form, with a molecular weight of from 1 to 5 kDa and most preferably with a molecular weight of 3.4 kDa, so that the aldehyde groups at opposite ends can form covalent bonds with the terminal amine groups of two polypeptides, thereby linking the amphipathic peptide to lipase. Particularly, aldehyde functional groups at opposite ends effectively allow non-specific reactions to be kept to a minimum.

In addition, no particular limitations are imposed on the state of conjugation between the amphipathic peptide and the lipase. In this context, the amphipathic peptide may be linked to either the N- or the C-terminus of the lipase, or two amphipathic peptides are linked to both the N- and the C-terminus of the lipase, respectively. For example, buforin IIb, B0, paracin I, NKC or NRC may be fused to the N-terminus of the lipase TliA (SEQ ID NO: 8 to 12), to the N-terminus of the lipase M37 (SEQ ID NO: 13 to 17), to the C-terminus of the lipase TliA (SEQ ID NO: 18 to 22), to the C-terminus of the lipase M37 (SEQ ID NO: 23 to 27), to both the N- and the C-terminus of the lipase TliA (SEQ ID NO: 28 to 32), or to both the N- and the C-terminus of the lipase M37 (SEQ ID NO: 33 to 37).

In one embodiment of the present invention, buforin IIb, B0, paracin I, NKC or NRC was used as an amphipathic peptide while TliA or M37 served as a lipase. The amphipathic peptide was connected to the N-terminus of the lipase to construct an amphipathic peptide-lipase which was found to have lipolysis activity up to 10-fold higher than that of the wild-type lipase itself (FIGS. 4 to 7). Thus, when conjugated with an amphipathic peptide, the lipolysis activity of a lipase is increased so that it can be used in various fields requiring lipolysis, with great economical profit. The amphipathic peptide-lipase was also observed to have improved accessibility to lipid particles (FIG. 8). In addition, the amphipathic peptide-lipase conjugate, NKC-M37 lipase, exhibited higher stability and lipolysis activity, compared to the wild-type lipase M37, even in the presence of methanol, one of the ingredients used in making biodiesel (FIGS. 9 and 10), suggesting that the amphipathic peptide-lipase conjugate of the present invention can be useful in producing biodiesel.

In accordance with another aspect thereof, the present invention provides a polynucleotide encoding the conjugate, an expression vector comprising the polynucleotide, and a transformant comprising the expression vector therein.

As use herein, the term "polynucleotide" refers to a polymer molecule composed of many nucleotide monomers covalently bonded in a chain. DNA (deoxyribonucleic acid) and RNA (ribonucleic acid) are examples of polynucleotides with distinct biological function. Thus, the polynucleotide of the present invention may be in the form of DNA or RNA coding for the conjugate.

The polynucleotide according to the present invention may encode, but not limited to, a conjugate in which buforin IIb, B0, paracin I, NKC or NRC is fused to the N-terminus of the lipase TliA (SEQ ID NO: 45 to 49), a conjugate in which buforin IIb, B0, paracin I, NKC or NRC is fused to the N-terminus of the lipase M37 (SEQ ID NO: 50 to 54), a conjugate in which buforin IIb, B0, paracin I, NKC or NRC is fused to the C-terminus of the lipase TliA (SEQ ID NO: 55 to 59), a conjugate in which buforin IIb, B0, paracin I, NKC or NRC is fused to the C-terminus of the lipase M37 (SEQ ID NO: 60 to 64), a conjugate in which buforin IIb, B0, paracin I, NKC or NRC is fused to both the N- and the C-terminus of the lipase TliA (SEQ ID NO: 65 to 69), or a conjugate in which buforin IIb, B0, paracin I, NKC or NRC is fused to both the N- and the C-terminus of the lipase M37 (SEQ ID NO: 70 to 74).

In the polynucleotide coding for the conjugate of the present invention, various modifications may be made in the encoding region provided that they do not change the amino acid sequence of the polypeptide expressed in the coding region, due to codon degeneracy or in consideration of the codons preferred by the organism in which they are to be expressed, and various modifications or alterations may be introduced even in regions other than the coding region so long as they have no influence on the expression of the gene. It is well understood to those skilled in the art that such modifications and alterations are within the scope of the present invention. That is to say, the polynucleotide of the present invention may be modified at one or more nucleic acid bases by substitution, deletion, insertion or a combination thereof as long as the resulting polynucleotides encode functionally equivalent polypeptides, and they are also within the scope of the present invention.

The expression vector comprising the polynucleotide coding for the conjugate in accordance with the present invention may be a vector that allows the polynucleotide to replicate and/or to be expressed in eukaryotic or prokaryotic cells including, but no limited to, mammal cells (e.g., human cells, monkey cells, rabbit cells, rat cells, hamster cells, murine cells, etc.), plant cells, yeasts, insect cells or bacterial cells (e.g., *E. coli*, etc.). In the expression vector, preferably, the nucleotide is operably linked to a proper promoter so that it is expressed in a host cell. Further, the expression vector may contain at least one selection marker. For example, the polynucleotide may be introduced into a phage, a cosmid, a mini-chromosome, or a viral or retroviral vector.

The transformant may be prepared by introducing the expression vector into a host cell. Examples of the host cell useful in the present invention include, but are not limited to, bacterial cells such as *E. coli, Streptomyces, Salmonella typhimurium*, etc.; yeasts; fungi such as *Pichia pastoris*; insect cells such as *Drosophila, Spodoptera*, and Sf9 cells; animal cells such as CHO (chinese hamster ovary cells), SP2/0 (mouse myeloma), human lymphoblastoid, COS, NSO (mouse myeloma), 293T, Bowes melanoma cell, HT-1080, BHK (baby hamster kidney cells), HEK (human embryonic kidney cells), and PERC.6 (human retinal cells); and plant cells. In one embodiment of the present invention, *E. coli* was used as a host cell (Example 2).

The term "introduction," as used herein, refers to the delivery of a vector comprising the polynucleotide coding for the conjugate into a host cell. The introduction may be accomplished by a variety of means known in the art including calcium phosphate-DNA co-precipitation, DEAE-dextran-mediated transfection, polybrene-mediated transfection, electric shock, micro-injection, liposome fusion, lipofection and protoplast fusion. Transfection refers to the transfer of a nucleic acid material of interest into cells by means of infection using viral particles. In addition, the cellular uptake of the expression vector may be achieved using gene bombardment. Herein, the term "introduction" may be used interchangeably with the term "transformation."

In accordance with a further aspect thereof, the present invention provides a method for preparing the amphipathic peptide-lipase conjugate.

Preferably, the method comprises (a) culturing a transformant comprising an expression vector that carries a polynucleotide coding for the amphipathic peptide-lipase conjugate; and (b) recovering the amphipathic peptide-lipase conjugate from the cell culture or culture medium.

The recovery step may be carried out using a purification method such as extraction, affinity chromatography, ion exchange chromatography, gel filtration chromatography, hydrophobic chromatography, protein precipitation, dialysis or a combination thereof, following disrupting the cellular mass from the cell culture or supernatant. The protein of interest that is recovered may be confirmed using a method well known in the art, such as SDS-PAGE, Western blotting, and so on.

In one embodiment of the present invention, genes encoding the amphipathic peptide-lipase conjugates, paracin I-TliA lipase, buforin IIb-TliA lipase, B0-TliA lipase, paracin I-M37 lipase, buforin IIb-M37 lipase, B0-M37 lipase, NKC-M37 lipase and NRC-M37 lipase were prepared and used to construct respective expression vectors carrying them (pET-Par-TliA, pET-Buf-TliA, pET-B0-TliA, pET-Par-M37, pET-Buf-M37, pET-B0-M37, pET-NKC-M37 and pET-NRC-M37). These expression vectors were introduced into *E. coli* to obtain respective transformants which were then cultured. The fusion polypeptides that were in the form of amphipathic peptide-lipase conjugate were recovered from the cultures (Examples 1 and 2, FIGS. 2 and 3).

In accordance with still a further aspect thereof, the present invention provides a method of lypolysis using the amphipathic peptide-lipase conjugate. The method comprises reacting the amphipathic peptide-lipase conjugate with a lipid.

The amphipathic peptide, the lipase and the amphipathic peptide-lipase conjugate are described above. Exhibiting improved accessibility and reactivity to lipid substrates thanks to the amphipathic peptide (FIGS. 4 to 8), the amphipathic peptide-lipase conjugate can be effective in lipolysis. The presence of the amphipathic peptide eliminates the necessity of using an additional surfactant and reduces the amount of lipase so that the amphiphatic peptide-lipase conjugate can hydrolyze lipids in an economically profitable manner.

As long as it serves as a substrate for lipase, any lipid may be employed without particular limitation.

Figure 4:
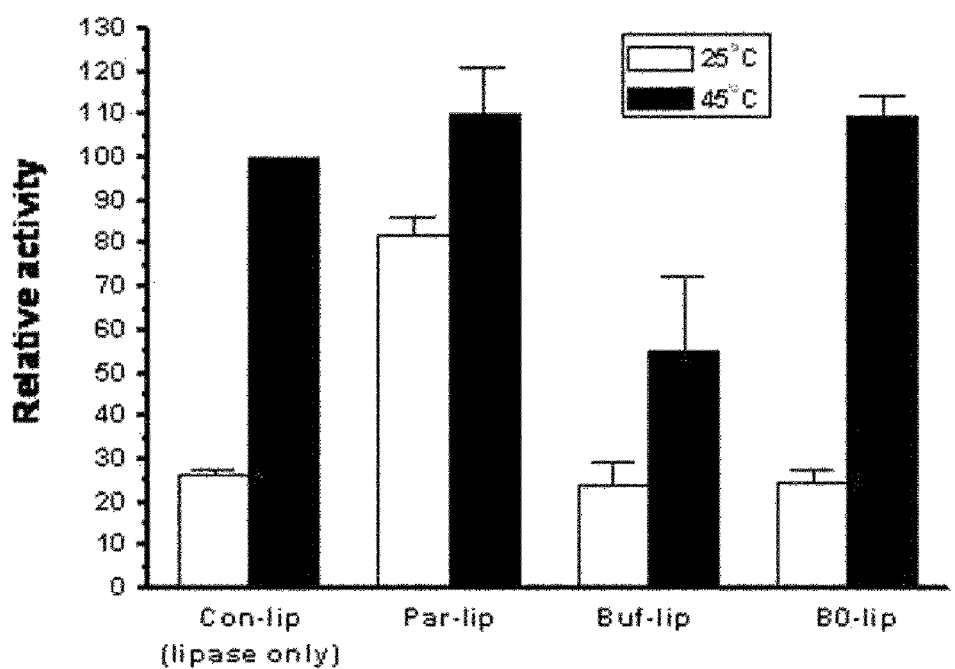
FIG. 4 is a graph showing lipolytic activities of the TliA lipase fused with the amphipathic peptides according to the present invention as measured by colorimetric assay using paranitrophenyl palmitate, which develops a color upon reaction with lipase.
Figure 5:
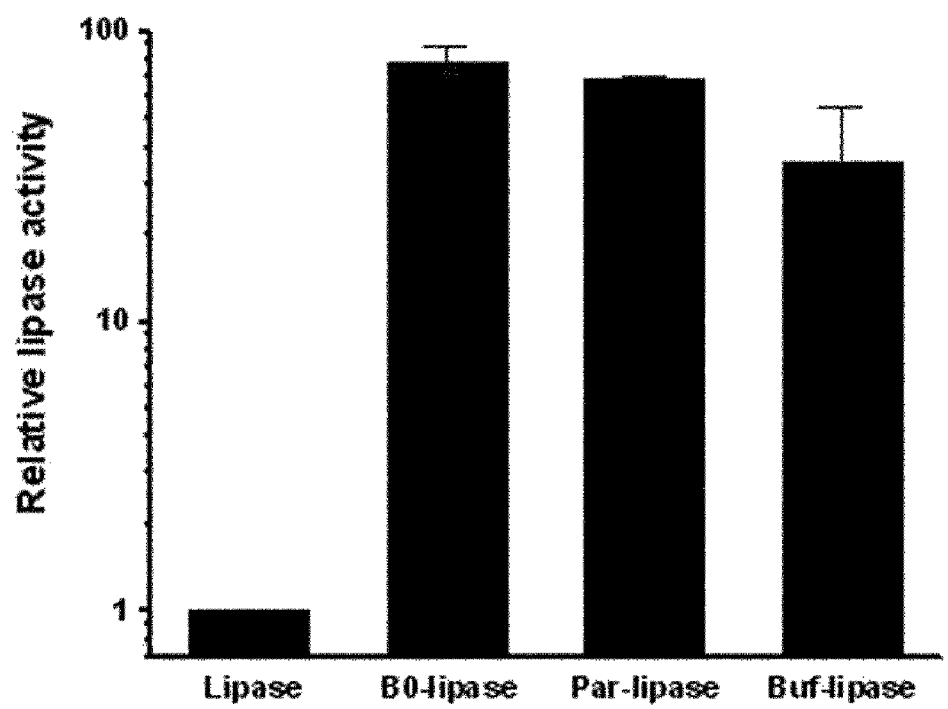
FIG. 5 is a graph showing the lipolytic activity of the TliA lipases prepared according to the present invention as measured by the pH-STAT method.
Figure 6:
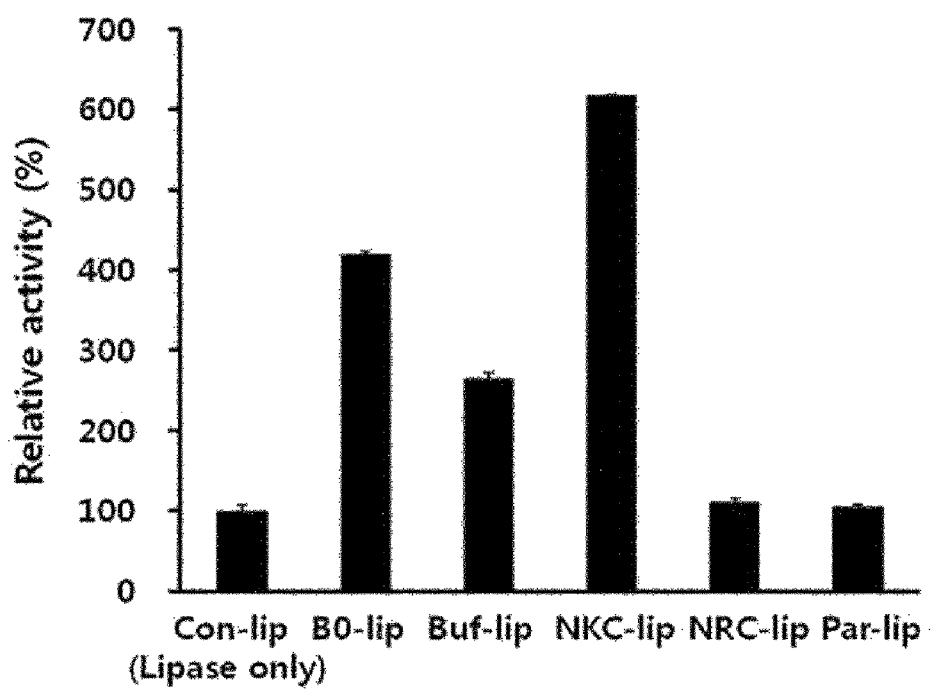
FIG. 6 is a graph showing lipolytic activities of the M37 lipase fused with the amphipathic peptides according to the present invention as measured by colorimetric assay using paranitrophenyl palminate.
Figure 7:
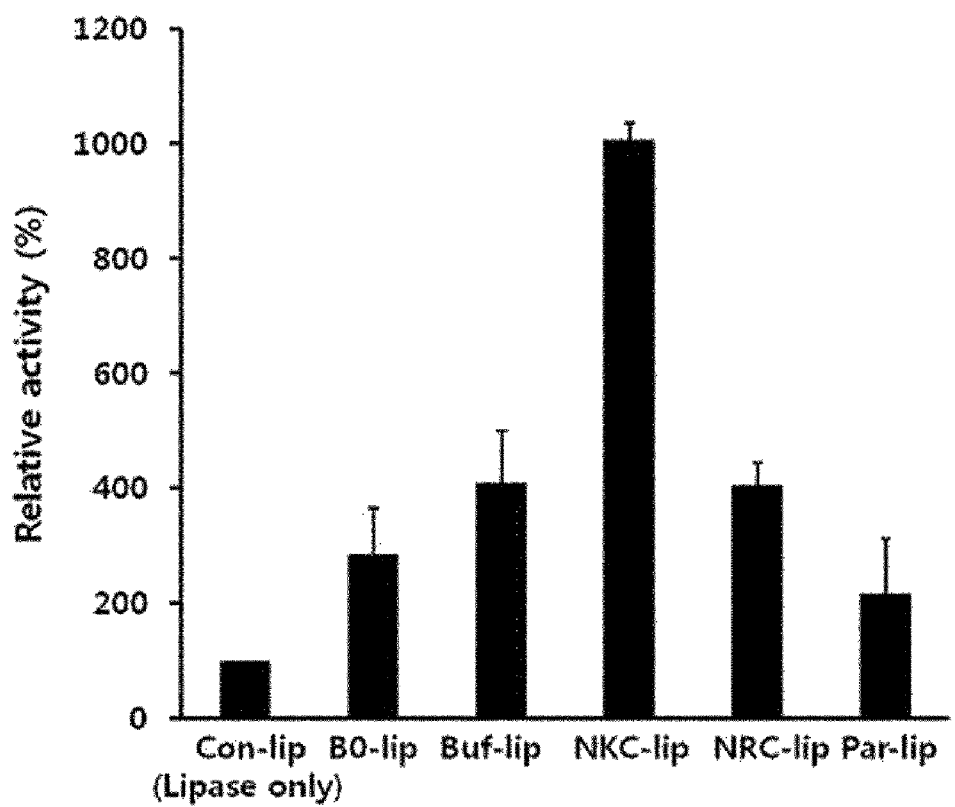
FIG. 7 is a graph showing the lipolytic activity of the M37 lipases prepared according to the present invention as measured by the pH-STAT method.

In one embodiment of the present invention, the lipolysis activity of the conjugate was compared with that of the wild-type lipase, which is void of the amphipathic peptide. For the comparison, paranitrophenyl palmitate and olive oil were used as the substrate. With regard to paranitrophenyl palmitate as a substrate, the activity of lipase TliA was found to increase by approximately 10% when in the form of the conjugate, compared to the wild-type lipase (FIG. 4). The activity of the conjugate comprising lipase M37 was increased 1.2- to 4.2-fold, compared to the wild-type (FIG. 6). When used on olive oil, the activity of lipase TliA, when fused to an amphipathic peptide, was found to increase by approximately 35.5- to 78-fold, compared to lipase TliA itself (FIG. 5). In the case of lipase M37, its lipolysis activity on olive oil was increased approximately 2.2 to 10.2 times when it was in the form of the conjugate, compared to the wild-type (FIG. 7). These data support the conclusion that the conjugates of the present invention can be effective for the hydrolysis of lipids.

In accordance with still another aspect thereof, the present invention provides a method for producing biodiesel using the amphipathic peptide-lipase conjugate.

Preferably, this method comprises, but is not limited to, reacting the amphiphatic peptide-lipase conjugate with oil and/or fats and alcohols.

Alternatively, the method for producing biodiesel may comprise, but is not limited to, (a) introducing the expression vector into a host cell to form a transformant; (b) culturing the transformant and recovering the lipase from the cell culture or culture medium; and (c) reacting oil and/or fats with alcohols in the presence of the lipase to produce biodiesel.

The lipase useful for the production of biodiesel in accordance with the present invention may be in a free form or in an immobilized form. The immobilization of the lipase may be accomplished using a variety of methods well known in the art including, but not limited to, physical methods such as adsoption and entrapment and chemical methods such as covalent bonding and crosslinking.

Among the oil and fats useful in the present invention are natural oil and fats, processed oil and fats and waste oil and fats. More preferable are soybean oil, rapeseed oil, and palm oil. The alcohols useful in the production of biodiesel in the present invention preferably contain 2 to 8 carbon atoms, and more preferably 2 to 4 carbon atoms. Examples of the alcohols include ethanol, methanol, 1-propanol, isopropanol, 1-butanol, 2-butanol, iso-butanol and tert-butanol. The feeding of alcohols may be accomplished using various feeding methods known in the art. For example, alcohols may be fed in a multi-stepwise feeding manner or in a continuous manner.

In one embodiment of the present invention, olive oil or waste oil, and methanol were employed as starting materials for producing biodiesel (Example 5). Typical lipases, such as CalB lipase, are unstable in media with a high content of methanol whereas the lipases of the present invention maintain high activities in 3.3%, 5% and even 10% methanol solutions (FIG. 9). In addition, under a 3-stepwise methanol feeding method (1 molar equivalent), the NKC-M37 lipase of the present invention guarantees a high production yield of biodiesel from olive oil. In fact, it allowed the production yield to be reached 95% faster (a savings of 21 hours) than the wild-type M37 lipase (FIG. 10a). In a 2-stepwise methanol feeding method, which is more economically profitable than the 3-stepwise methanol feeding method, the conjugate of the present invention brought about the maximum conversion yield by 27 hours faster than the wild-type M37 lipase could (FIG. 10b). The maximum conversion rate was also achieved within a far shorter time by the lipase conjugate of the present invention than the wild-type lipase under a 1-step methanol feeding method (FIG. 10c).

In addition, oil wastes are known to be difficult to apply to biodiesel production because of the impurities, free fatty acid and water content therein. Also, its impurities have negative influence on lipases, although they are very cheap. However, the NKC-M37 lipase of the present invention was found to produce biodiesel from oil wastes to a degree similar to that from olive oil or palm oil, demonstrating that the conjugates of the present invention are economically beneficial in biodiesel production (Example 5).

MODE FOR INVENTION

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Development of Fusion Lipases Where Lipase is Fused with Various Amphipathic Peptides Example 1-1

Preparation of Peptide Derivatives

Many different peptides with potent antibacterial activity form amphipathic α-helical structures consisting of hydrophobic and hydrophilic amino acid residues. Antibacterial peptides of excellent amphipathicity, buforin IIb comprising the amino acid sequence of SEQ ID NO: 1 (Korean Patent No. 10-314721), B0, modified from buforin IIb, comprising the amino acid sequence of SEQ ID NO: 2, Paracin I comprising the amino acid sequence of SEQ ID NO: 3 (Korean Patent No. 10-330136), NKC comprising the amino acid sequence of SEQ ID NO: 4, and NRC comprising the amino acid sequence of SEQ ID NO: 5 (Korean Patent No. 10-836596) (Table 1) were prepared by the present inventors and used to construct fusion polypeptides of enhanced lipolytic activity.

TABLE 1

Amphipathic Peptides Used in the Present Invention

| Name | Amino Acid Sequence (N-C) | SEQ ID NO: |
|---|---|---|
| buforin IIb | RAGLQFPVGRLLRRLLRRLLR | 1 |
| B0 | RAGLQFPVG | 2 |
| paracin I | KGRGKQGGKVRAKAKTRSS | 3 |
| NKC | APKAMKLLKKLLKLQKKGI | 4 |
| NRC | APKAMRLLRRLLRLQKKGI | 5 |

The α-helical structures of the five amphipathic peptides can be visualized schematically by using the Schiffer and Edmundson wheel projection, as shown in FIG. 1. In this wheel, each of the consecutive amino acids corresponds to a 100° turn so that the helix has 3.6 residues per turn.

Example 1-2

Construction of Genes Coding for Peptide-Lipase Conjugates

PCR (polymerase reaction reaction) was performed on plasmids pHOPE (Eom, G T, et al., Applied Environ. Microbiol., 71:3468-3474, 2005) and pEML37 (Yang K S, et al., J. Biosci. Bioeng., 107:599-604, 2009), which respectively carry a *Pseudomonas fluorescens*-derived gene coding for lipase TliA, known to have potent enzymatic activity and to guarantee a high conversion rate for biodiesel production, and a *Photobacterium lipolyticum*-derived gene coding for lipase M37, known to be highly resistant to methanol, to amplify the lipase genes which were then fused to the genes encoding the selected amphipathic peptides. The information of primers used in the PCR is shown in Table 2.

TABLE 2

| Primer | Sequence(5'->3') | SEQ ID NO |
|---|---|---|
| pET16-L | 5'-cgtagaggatcgagatctcgatcc-3' | SEQ ID NO: 75 |
| pET-R (Par) | 5'-gccttcgcacgcaccttgcctccctgtttgcctcttcctttacgaccttcgatatggccg-3' | SEQ ID NO: 76 |
| TliA-rev (Par) | 5'-gggaggcaaggtgcgtgcgaaggcaaagacacgttcatccggtgtatttgactacaagaacc-3' | SEQ ID NO: 77 |
| NdeI-TliA-for | 5'-cttaaggcatatgtcaactgatcagcacaccctcg-3' | SEQ ID NO: 78 |
| pET-R (Buf) | 5'-cgacgcagcagacgaccaaccgggaactgcagaccagcacgacgaccttcgatatggccg-3' | SEQ ID NO: 79 |
| TliA-rev (Buf) | 5'-cccggttggtcgtctgctgcgtcgtctgctgcgtcgtctgctgcgtggtgtatttgactacaagaacc-3' | SEQ ID NO: 80 |

TABLE 2-continued

| Primer | Sequence(5'->3') | SEQ ID NO |
|---|---|---|
| pET-R (B0) | 5'-caaccgggaactgcagaccagcacgacgac cttcgatatggccg-3' | SEQ ID NO: 81 |
| TliA-rev(B0) | 5'-gctggtctgcagttcccggttggtggtgta tttgactacaagaacc-3' | SEQ ID NO: 82 |
| pET-R (con) | 5'-acgaccttcgatatggccg-3' | SEQ ID NO: 83 |
| TliA-rev (con) | 5'-cggccatatcgaaggtcgtggtgtatttga ctacaagaacc-3' | SEQ ID NO: 84 |
| M37-rev (Buf) | 5'-cccggttggtcgtctgctgcgtcgtctgct gcgtcgtctgctgcgtgcatctccacgcgc caatgatg-3' | SEQ ID NO: 85 |
| Nde-M37-for | 5'-cttaaggcatatgttataacaaaccgcga tcgca-3' | SEQ ID NO: 86 |
| M37-rev (Par) | 5'-gggaggcaaggtgcgtgcgaaggcaaagac acgttcatccgcatctccacgcgccaatga tg-3' | SEQ ID NO: 87 |
| M37-rev (B0) | 5'-gctggtctgcagttcccggttggtgcatct ccacgcgccaatgatg-3' | SEQ ID NO: 88 |
| M37-rev (NKC) | 5'-actgttgaagaaattgctgaaattacagaa aaaaggcattgcatctccacgcgccaatga tg-3' | SEQ ID NO: 89 |
| M37-rev (NRC) | 5'-tctgttgcgtcgcttgctgcgtttacagaa aaaaggcattgcatctccacgcgccaatga tg-3' | SEQ ID NO: 90 |
| M37-rev (con) | 5'-gcagcggccatatcgaaggtcgtgcatctc cacgcgccaatg-3' | SEQ ID NO: 91 |

Example 1-2-1

Construction of a Gene Encoding a Paracin I/Lipase TliA Conjugate

To construct a gene coding for a paracin I/TliA lipase fusion protein, first, a gene fragment connected to the T7 promoter-ribosomal binding site-His tag in pET16b (Merck biosciences) was amplified by PCR using a pair of primers pET16-L and pET-R (Par).

Separately, PCR was performed on pHOPE using primers TliA-rev (Par) and Nde-TliA-for to synthesize a DNA fragment in which the lipase gene is fused to a part of the paracin.

While the two amplified DNA fragments were used as a substrate, a T7 promoter-ribosomal binding site-His tag-paracin I peptide-lipase gene was amplified by PCR using the primers pET16-L and Nde-TliA-for.

Example 1-2-2

Construction of a Gene Encoding a Buforin IIb/Lipase TliA Conjugate

To construct a gene coding for a buforin IIb/TliA lipase fusion protein, first, a gene fragment connected to the T7 promoter-ribosomal binding site-His tag in pET16b was amplified by PCR using a pair of primers pET16-L and pET-R(Buf).

Separately, PCR was performed on pHOPE using primers TliA-rev (Buf) and Nde-TliA-for to synthesize a DNA fragment in which the lipase gene is fused to a part of the buforin gene.

While the two amplified DNA fragments were used as a substrate, a T7 promoter-ribosomal binding site-His tag-buforin IIb peptide-lipase gene was amplified by PCR using the primers pET16-L and Nde-TliA-for.

Example 1-2-3

Construction of a Gene Encoding a B0/Lipase TliA Conjugate

To construct a gene coding for a B0/TliA lipase fusion protein, first, a gene fragment connected to the T7 promoter-ribosomal binding site-His tag in pET16b was amplified by PCR using a pair of primers pET16-L and pET-R (B0).

Separately, PCR was performed on pHOPE using primers TliA-rev (B0) and Nde-TliA-for to synthesize a DNA fragment in which the lipase gene is fused to a part of the buforin gene.

While the two amplified DNA fragments were used as a substrate, a T7 promoter-ribosomal binding site-His tag-B0 peptide-lipase gene was amplified by PCR using the primers pET16-L and Nde-TliA-for.

Example 1-2-4

Construction of a Control Gene Comprising Lipase TliA

A control DNA devoid of any amphipathic peptide (T7 promoter-ribosomal binding site-His tag-lipase TliA) was amplified. To this end, first, PCR was performed on pET16b using the DNA primers pET16-L and pET-R (con) to synthesize a T7 promoter-ribosomal binding site-His tag gene fragment.

Separately, PCR was performed in the presence of the primers TliA-rev (con) and Nde-TliA-for, with pHOPE serving as a substrate, to amplify a DNA fragment comprising the lipase gene.

While the two amplified DNA fragments were used as a substrate, a T7 promoter-ribosomal binding site-His tag-lipase gene was amplified by PCR using the primers pET16-L and Nde-TliA-for.

Example 1-2-5

Construction of a Gene Encoding a Buforin IIb/Lipase M37 Conjugate

A gene coding for a buforin IIb/M37 lipase fusion protein was constructed. In this regard, first, a gene fragment connected to the T7 promoter-ribosomal binding site-His tag in pET16b was amplified by PCR using a pair of primers pET16-L and pET-R (Buf). Separately, PCR was performed on pEML37 using the primers M37-rev(Buf) and Nde-M37-for to synthesize a DNA fragment in which the lipase gene is fused to a part of the amphipathic peptide gene. While the two amplified DNA fragments were used as a substrate, a T7 promoter-ribosomal binding site-His tag-buforin IIb-lipase gene was amplified by PCR using the primers pET16-L and Nde-M37-for.

Example 1-2-6

Construction of a Gene Encoding a Paracin I/Lipase M37 Conjugate

A gene coding for a paracin I/M37 lipase fusion protein was constructed. In this regard, first, a gene fragment connected to the T7 promoter-ribosomal binding site-His tag in pET16b was amplified by PCR using a pair of primers pET16-L and pET-R (Par). Separately, PCR was performed on pEML37 using the primers M37-rev(Par) and Nde-M37-for to synthesize a DNA fragment in which the lipase gene is fused to a part of the amphipathic peptide gene. While the two amplified DNA fragments were used as a substrate, a T7 promoter-ribosomal binding site-His tag-paracin I-lipase gene was amplified by PCR using the primers pET16-L and Nde-M37-for.

Example 1-2-7

Construction of a Gene Encoding a B0/Lipase M37 Conjugate

A gene coding for a B0/M37 lipase fusion protein was constructed. In this regard, first, a gene fragment connected to the T7 promoter-ribosomal binding site-His tag in pET16b was amplified by PCR using a pair of DNA primers pET16-L and pET-R (B0). Separately, PCR was performed on pEML37 using the primers M37-rev(B0) and Nde-M37-for to synthesize a DNA fragment in which the lipase gene is fused to a part of the amphipathic peptide gene. While the two amplified DNA fragments were used as a substrate, a T7 promoter-ribosomal binding site-His tag-B0 lipase gene was amplified by PCR using the primers pET16-L and Nde-M37-for.

Example 1-2-8

Construction of a Gene Encoding a NKC/Lipase M37 Conjugate

A gene coding for a NKC/M37 lipase fusion protein was constructed. In this regard, first, a gene fragment connected to the T7 promoter-ribosomal binding site-His tag in pET16b was amplified by PCR using a pair of primers pET16-L and pET-R (NKC). Separately, PCR was performed on pEML37 using the primers M37-rev(NKC) and Nde-M37-for to synthesize a DNA fragment in which the lipase gene is fused to a part of the amphipathic peptide gene. While the two amplified DNA fragments were used as a substrate, a T7 promoter-ribosomal binding site-His tag-NKC-lipase gene was amplified by PCR using the primers pET16-L and Nde-M37-for.

Example 1-2-9

Construction of a Gene Encoding a NRC/Lipase M37 Conjugate

A gene coding for an NRC/M37 lipase fusion protein was constructed. To this end, a gene fragment connected to the T7 promoter-ribosomal binding site-His tag in pET16b was amplified by PCR using a pair of primers pET16-L and pET-R (NRC). Separately, PCR was performed on pEML37 using the primers M37-rev(NRC) and Nde-M37-for to synthesize a DNA fragment in which the lipase gene is fused to a part of the amphipathic peptide gene. While the two amplified DNA fragments were used as a substrate, a T7 promoter-ribosomal binding site-His tag-NRC-lipase gene was amplified by PCR using the primers pET16-L and Nde-M37-for.

Example 1-2-10

Construction of a Control Gene Comprising Lipase M37

A control DNA avoid of any amphipathic peptide (T7 promoter-ribosomal binding site-His tag-lipase M37) was amplified. To this end, PCR was performed on pET16b using the DNA primers pET16-L and pET-R (NRC), to synthesize a T7 promoter-ribosomal binding site-His tag gene fragment. Separately, PCR was performed in the presence of the primers M37-rev (con) and Nde-M37-for, with pEML37 serving as a substrate, to amplify a DNA fragment comprising the lipase gene. Then, while the two amplified DNA fragments were used as a substrate, a T7 promoter-ribosomal binding site-His tag-M37 lipase gene was amplified by PCR using the primers pET16-L and Nde-M37-for.

Example 1-3

Figure 2:
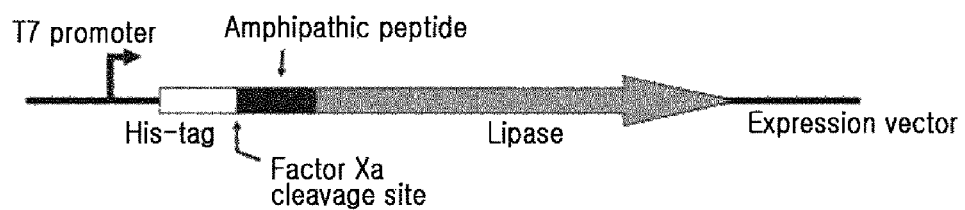
FIG. 2 is a schematic diagram showing the gene structure of a vector for expressing the activity-enhanced lipase.

Construction of Expression Vector Comprising Amphipathic Peptide/Lipase Fusion Protein Gene The T7 promoter-ribosomal binding site-His tag-peptide-lipase conjugate DNAs constructed in Example 1-2 were digested with restriction enzymes BglII and NdeI and cloned into respective pET16b vectors which were previously digested with the same restriction enzymes (FIG. 2). FIG. 2 is a schematic view showing the gene structure of a vector for expressing the activity-enhanced lipase. In the vector, an amphipathic peptide gene is located downstream of a conditional promoter, with the fusion thereof to the N-terminus of the lipase gene. In addition, a histidine-tag is provided, ahead of the amphipathic peptide, for protein purification while a recognition site of the proteinase Factor Xa is intercalated between the histidine tag and the peptide gene, with the aim of removing the histidine tag after expression and purification. After being expressed, the histidine tag-peptide-lipase conjugate was separated using an Ni-column and treated with the enzyme Factor Xa to isolate the desired amphipathic peptide-lipase structure. As mentioned above, the genes are located downstream of the conditional promoter so that the lipase that has enhanced activity because of fusion to the amphipathic peptide can be expressed under the desired conditions.

The cloned plasmids were transformed into E. coli XL1-Blue (Invitrogen), followed by selection on LB plates containing ampicillin. To evaluate whether the plasmids were correctly constructed, they were prepared from colonies grown on the plates and digested with the restriction enzymes BglII and NdeI. The DNA digests were run on agarose gel to measure the sizes thereof and subjected to DNA base sequencing.

As a result, the recombinant expression plasmids carrying TliA lipase (control), paracin I-TliA lipase, buforin IIb-TliA lipase, B0-TliA lipase, M37 lipase (control), paracin I-M37 lipase, buforin IIb-M37 lipase, B0-M37 lipase, NKC-M37 lipase, and NRC-M37 lipase were respectively designated pET-TliA, pET-Par-TliA, pET-Buf-TliA, pET-B0-TliA, pET-M37, pET-Par-M37, pET-Buf-M37, pET-B0-M37, pET-NKC-M37 and pET-NRC-M37.

Example 2

Isolation of Peptide-Lipase Conjugate and Assay for Enzymatic Activity

Example 2-1

Expression of Peptide-Lipase Fusion Protein

Peptide-lipase fusion proteins were expressed. For this, the plasmids constructed previously were electroporated into *E. coli* BL21(DE3) (Merck biosciences) which was then spread over plates. Single colonies thus grown were selected and inoculated into LB broth. At 37° C., the cells were cultured to an optical density of 0.4 at 600 nm. The expression of the peptide-lipase conjugates was induced in the presence of 1 mM IPTG (isopropyl-1-thio-β-D-galactopyranoside). The *E. coli* cells were harvested 4 hours after induction. The expression of the peptide-lipase conjugates of interest was examined by 10% SDS-PAGE. Protein levels were determined using the Bradford assay.

Figure 3:
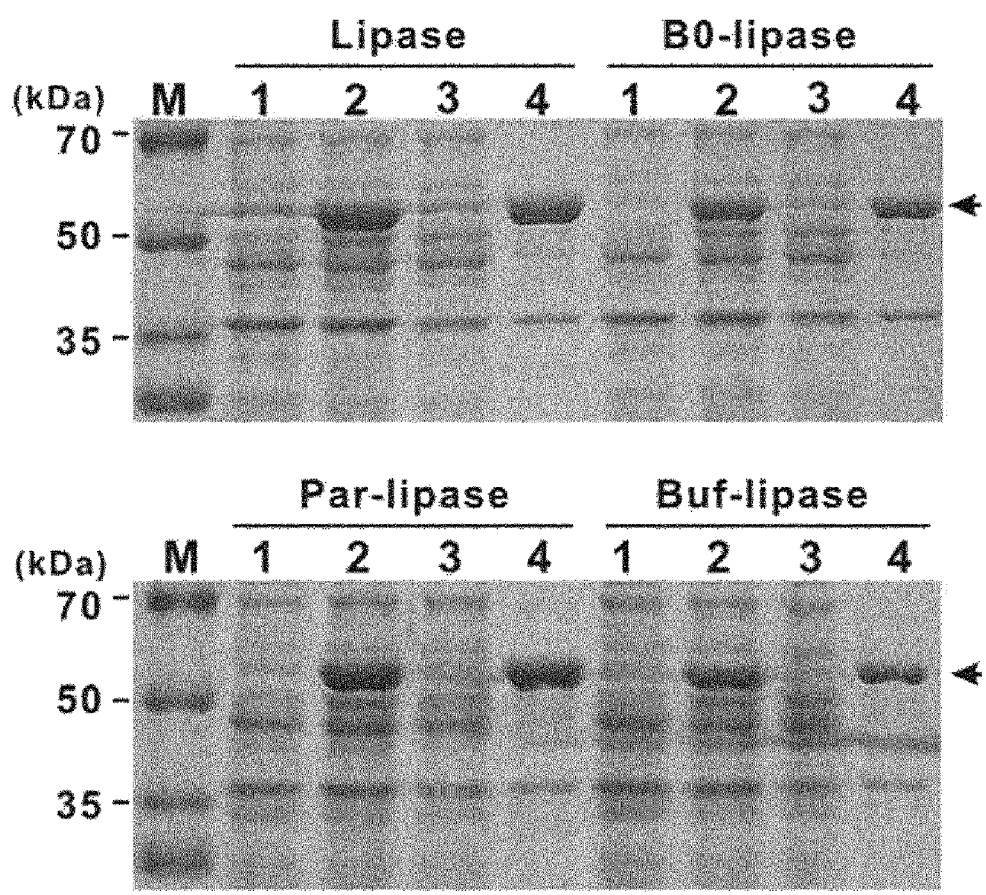
FIG. 3 is an SDS-PAGE photograph showing the expression of the peptide-lipase TliA conjugate.

As a result, the peptide-lipase fusion proteins were observed to be expressed as inclusion bodies in *E. coli* (FIG. 3). With reference to FIG. 3, SDS-PAGE photographs showing the expression of the peptide-lipase TliA fusion protein are provided, where a size marker was run on lane M, cell lysates without IPTG induction on lane 1, cell lysates with IPTG induction on lane 2, soluble supernants of cell lysates with IPTG induction on lane 3, and inclusion bodies with IPTG induction on lane 4, and Par stands for paracin I and Buf for buforin IIb.

Example 2-2

Isolation of Peptide-Lipase Fusion Protein

In order to isolate the recombinant proteins, the *E. coli* cells were suspended in lysis buffer (50 mM $NaH_2PO4$, 300 mM NaCl, pH 8.0) and disrupted by ultrasonication (520 sec, 0.5 cycles, 50% amplitude). After ultrasonication, the cell lysates thus obtained were centrifuged at 4° C. at 12,000 rpm for 20 min to divide a soluble supernatant from a non-soluble portion including inclusion bodies. The peptide-lipase fusion proteins in the non-soluble portion were dissolved in wash buffer (100 mM $NaH_2PO_4$, 10 mM Tris-Cl, 8M urea, pH 6.3), followed by centrifugation to remove celldebris. Thereafter, the supernatant was loaded to NTA ($Ni^{2+}$ nitriloacetic acid) agarose columns (Qiagen, Hilden, Germany) to catch the peptide-lipase fusion proteins and separate them therefrom, followed by membrane dialysis to remove the remaining impurities. To eliminate the His tag used to isolate the fusion proteins, they were treated with Factor Xa (New England Biolab, USA). The confirmation of the purified proteins was achieved by 10% SDS-PAGE and N-terminal amino acid sequencing.

Example 2-3

Assay of Peptide-Lipase Fusion Protein for Lipase Activity

Example 2-3-1

Measurement of Lipase Activity Using Paranitrophenyl Palmitate

Lipase activity was measured by colorimetric assay using p-nitrophenyl palmitate. A solution of 10 mM paranitrophenyl palmitate in acetonitrile, ethanol and 50 mM Tris-HCl solution (pH 8.5) were mixed at a ratio of 1:4:95. To 0.8 mL of the paranitrophenyl palmitate mixture was added 0.2 mL of a fusion protein solution, followed by incubation at 45° C. for 10 min before absorbance at 405 nm was measured. The results are shown in FIGS. 4 and 6. FIG. 4 is a graph showing lipolytic activities of the TliA lipase fused with the amphipathic peptides according to the present invention as measured by colorimetric assay using paranitrophenyl palmitate, which develops a color upon reaction with lipase. FIG. 6 is a graph showing the lipolytic activities of the M37 lipase fused with the amphipathic peptides according to the present invention as measured by colorimetric assay using paranitrophenyl palmitate.

Even at room temperature, as can be seen from the data of FIG. 4, the paracin-TliA fusion lipase (Par-lip) exhibits an enzymatic activity similar to that of the wild-type lipase (control) at the optimal reaction temperature of 45° C. TliA, when fused with paracin I or B0, was found to increase in activity at 45° C. by approximately 10%, compared to the control. It is understood in FIG. 6 that the B0/M37 lipase fusion protein (B0-M37), the buforin IIb/M37 lipase fusion protein (Buf-M37), the NKC/M37 lipase fusion protein (NKC-M37), the NRC/M37 lipase fusion protein (NRC-M37), and the paracin I/M37 lipase fusion protein (Par-M37) increased 4.2-, 2.7-, 6.3-, 1.3- and 1.2-fold in activity, compared to the control, respectively. These data indicate that amphipathic peptides, when fused to lipases, significantly enhance the activity of the lipases.

Example 2-3-2

Measurement of Lipase Activity Using Olive Oil Hydrolysis

For more precise quantitative analysis, the lipase activity was measured by titrating the free fatty acids released by the hydrolysis of olive oil. An olive oil emulsion was prepared by emulsifying 5 mL of olive oil in 450 mL of a 20 mM NaCl, 1 mM $CaCl_2$, 0.5% (w/v) gum arabic solution for 2 min at maximum speed in a Waring blender. After the pH of the substrate emulsion was adjusted to 8.0 by the addition of 10 mM NaOH solution, the enzyme solution was added thereto. The rate of the fatty acid release was measured with a pH titrator (718 Stat Titrino, Metrohm) for 5 min at 50° C. The results are shown in FIGS. 5 and 7. FIG. 5 is a graph showing the lipolytic activity of the TliA lipases prepared according to the present invention as measured by the pH-STAT method. FIG. 7 is a graph showing the lipolytic activity of the M37 lipases prepared according to the present invention as measured by the pH-STAT method.

As is apparent from the data of FIG. 5, the activity of B0-TliA, Par-TliA, Buf-TliA fusion proteins were found to be 78±11.3, 68.5±2.1, and 35.5±19.1 times as large as that of TliA itself, respectively. In addition, as shown in FIG. 7, B0-M37, Buf-M37, NKC-M37, NRC-M37, and Par-M37 were 2.8-, 4.2-, 10.2-, 4.1-, and 2.2-fold increased in activity, respectively, compared to M37 itself.

These data indicate that lipases associated with amphipathic peptides have excellent lipolytic activity as compared to lipases alone.

Example 3

Assay for Increased Accessibility of NKC-Fused M37 Lipase (NKC-M37) to Lipid Substrates The active site of M37 lipase was covered by a lid helix (α3). Most of the hydrophobic residues (Ile97, Trp100, Leu101, and Phe102) present near the lid of M37 lipase were buried and distributed over the active site, suggesting that substrate binding might cause these residues to become exposed and to form a wide hydrophobic surface. Therefore, some conformational change is needed in order for the hydrophobic substrates to access the active site of the M37 lipase.

Conjugation with the amphipathic peptide NKC to the M37 lipase, creates a better state of hydrophobic substrate access to the lipase active site and increasing the affinity between enzyme and substrate. For further evaluation in this context, GFP hybrids with the wild-type M37 or with the NKC-fused M37 lipase were constructed, and localization of these lipases within the lipid particles was determined (FIG. 8). Fluorescence microscopic inspection demonstrated that the NKC-fused M37 lipase was much more localized to lipid particles compared to the wild-type M37 lipase, indicating that these amphipathic peptides necessarily form a functional complex.

Example 4

Assay for Effects of the Amphipathic Peptide on Stability of M37 Lipase Against Methanol Methanol functions as a solvent as well as an enzyme substrate in the process of biodiesel production. However, because general lipases are unstable in a medium that has a high concentration of methanol, the yield of biodiesel production is rather limited. To fully convert 1 molar equivalent of triacylglycerol to its corresponding methyl esters, at least 3 molar equivalents of methanol are needed. However, general lipases were inactivated in a media containing more than 1 molar equivalent (3.3% v/v) of methanol, compared to oil. Thus, the biodiesel production reaction was conducted by adding methanol multi-stepwise to avoid lipase inactivation.

It was previously reported that the M37 lipase clearly showed high stability even in high concentrations of methanol. When the 1-stepwise methanol feeding (3 molar equivalents) method was employed, the M37 lipase resulted in a 70% conversion yield, while CalB lipase (*Candida Antarctica* lipase B) allowed only a small amount of the oil to be converted to biodiesel.

The following experiments were performed to evaluate whether or not the conversion yield of M37 lipase, which is stable even in a high concentration of methanol, is increased when it is associated with an amphipathic peptide.

The NKC-fused M37 lipase was assayed for stability against a high concentration of methanol. In this regard, the residual activity remaining after methanol treatment was measured to evaluate enzyme stability. The stability of CalB lipase, wild-type M37 lipase and NKC-M37 lipase was measured for 12 h in 0%, 3.3%, 5%, and 10% methanol solutions at 4° C. and 40° C.

As a result, the wild-type M37 lipase and the NKC-fused M37 lipase maintained its activity in 3.3%, 5%, and 10% methanol solutions at 4° C. When measured at the actual temperature of trans-esterification reaction, that is, 40° C., in a 10% methanol solution, the stability of NKC-M37 lipase to methanol was slightly lower than that of the wild-type M37 lipase while the CalB lipase was rapidly inactivated in 10% methanol solution at 40° C. (FIG. 9). Thus, the NKC-M37 lipase is quite stable in methanol like the wild-type M37 lipase, indicating that the conjugates of the present invention can be effective in the production of biodiesel.

Example 5

Biodiesel Production Using the NKC-Fused M37 Lipase

As illustrated in FIG. 7, the NKC-M37 lipase showed 10-fold higher catalytic activity compared to the wild-type M37 lipase, indicating that the amphipathic peptides such as NKC are highly effective in improving the catalytic activity of the M37 lipase by increasing the accessibility between lipase and lipid substrates. In this context, biodiesel production reaction processes, and the trans-esterification of olive oil were conducted, using the NKC-M37 lipase with improved catalytic activity.

For biodiesel production, oil/methanol at a stoichiometric molar ratio was placed into a reaction flask and heated to a reaction temperature, with stirring. On the whole, lipases are inactivated when they are subject to a mixture containing more than 1 molar equivalent of methanol compared to the oil. Accordingly, the biodiesel production reaction was conducted by adding methanol in a multiple step manner. However, as demonstrated in Example 4, the wild-type M37 lipase and the NKC-M37 lipase were stable even in the presence of 3 molar equivalents of methanol.

Figure 10:
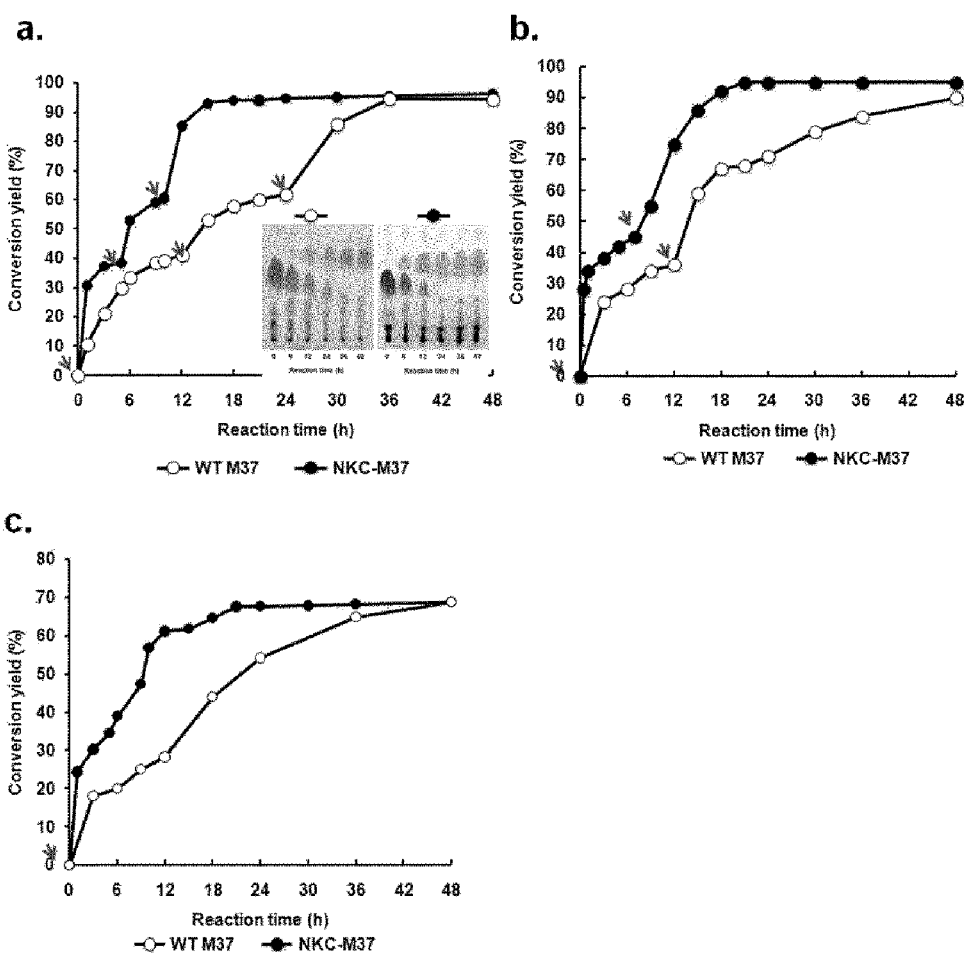
FIG. 10 shows biodiesel production conducted with olive oil using the wild type M37 lipase and NKC-M37 lipase. The biodiesel were quantitatively analyzed by gas chromatography and qualitatively by thin layer chromatography. (A) Time course of three-step trans-esterification of olive oil using the wild-type M37 lipase (open circle) and NKC-fused M37 lipase (closed circle). Also, TLC analysis of the reaction mixture during the transesterification reaction using the wild-type M37 lipase (left) and NKC-fused M37 lipase (right). The arrows indicate the addition of methanol into the reaction mixture. (B) Time course of two-step transesterification of olive oil using the wild-type M37 lipase and NKC-fused M37 lipase. (C) Time course of one-step trans-esterification of olive oil using the wild-type M37 lipase and NKC-fused M37 lipase.

First, the 3-stepwise methanol feeding (1 molar equivalent) method was utilized. The amount of produced biodiesel was analyzed using both gas chromatography and thin layer chromatography (FIG. 10 *a*).

The thin layer chromatography analysis showed that most of the olive oil was found to be converted into biodiesel. FIG. 10 shows the time it takes to reach 95% conversion for the wild-type M37 lipase and for the NKC-M37 lipase. Gas chromatography analysis demonstrated that a biodiesel process using the wild-type M37 lipase resulted in a 95% conversion yield after a 36 hour reaction. However, the NKC-M37 lipase required only 15 hours to reach a 95% conversion yield (FIG. 10 *a*). This data suggests that the amphipathic peptide-fused lipases according to the present invention are useful in the economical and effective production of biodiesel.

As previously mentioned, an enzymatic biodiesel production process currently utilizes a 3-step methanol feeding method because of the low tolerance to methanol. Hence, in order to produce economical and viable biodiesel, an attempt was made to develop an enzymatic biodiesel production process that could utilize a 2-step methanol feeding method. When the 2-step methanol feeding (2 molar equivalents) method was used, the NKC-M37 lipase with highly improved catalytic activity in accordance with the present invention resulted in a conversion rate of at least 90% within 21 hours of the reaction whereas it took as long as 48 hours for the wild-type M37 lipase to reach the same conversion rate (FIG. 10 b), demonstrating that the amphipathic peptide-fused lipases according to the present invention are very efficient catalysts compared to the wild-type lipases. Separately, the NKC-M37 lipase was found to reach the maximum conversion rate much faster than the wild-type M37, under a 1-step methanol feeding method (FIG. 10 c).

In addition, the cost of biodiesel varies depending largely on the cost of the feedstock. It has been reported that the cost of feedstock accounts for more than 70% of the cost of biodiesel production. Higher production costs are likely to induce lower commercial use. To make biodiesel cost competitive over petro-diesel, low cost feedstock such as waste cooking oil, beef tallow, pork lard, and yellow grease are under study. However, impurities, free fatty acids, and high water content in the waste oil greatly reduce the production yield of biodiesel. A previous report disclosed that the M37 lipase is not affected by the free fatty acids and water component in waste oil. When waste oil was utilized using the NKC-M37 lipase, biodiesel was produced to an extent similar to that of olive oil and palm oil. Taken together, the result indicates that the NKC-M37 lipase of the present invention can be used to produce biodiesel with great efficiency.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements.

The invention claimed is:

1. A method for increasing a lipase activity, comprising fusing an amphipathic peptide at the N-terminus of a lipase, wherein the amphipathic peptide is NKC comprising amino acid sequence of SEQ ID NO:4.

2. The method of claim 1, wherein the lipase is *Photobacterium lipolyticum*-derived lipase M37 comprising amino acid sequence of SEQ ID NO:7.

3. The method of claim 1, further comprising amphipathic peptide linked to the C-terminus of the lipase.

4. The method of claim 1, wherein the amphipathic peptide is fused to the lipase via a peptide linker.

5. The method of claim 1, wherein the amphipathic peptide is fused to the lipase via a non-peptidyl linker.

6. The method of claim 5, wherein the non-peptidyl linker is selected from the group consisting of polyethylene glycol homopolymers, polypropylene glycol homopolymers, ethylene glycol-propylene glycol copolymers, polyoxyethylated polyol, polyvinyl alcohols, polysaccharides, dextran, polyvinyl ethyl ether, lipid polymers and any combination thereof.

7. The method of claim 1, wherein the peptide fusion comprises amino acid sequence of SEQ ID NO:16.

8. The method of claim 1, wherein the amphipathic peptide fused to a lipase has at least a 2.2 fold increase in lipase activity for an triglyceride than the lipase without an amphipathic peptide.

9. A method for preparing an amphipathic peptide-lipase conjugate having an increased affinity between the lipase and substrate, comprising:
　(a) culturing a transformant comprising a polynucleotide encoding an amphipathic peptide-lipase fusion in which an amphipathic peptide is fused to the N-terminus of a lipase; and
　(b) recovering the amphipathic peptide-lipase conjugate from the cell culture or culture medium,
　wherein the amphipathic peptide is NKC comprising an amino acid sequence of SEQ ID NO:4.

10. The method of claim 9, wherein the fusion comprises amino acid sequence of SEQ ID NO:16.

11. A method of lipolysis, comprising contacting an amphipathic peptide-lipase fusion in which an amphipathic peptide is fused to the N-terminus of a lipase with a lipid substrate, wherein the amphipathic peptide is NKC comprising amino acid sequence of SEQ ID NO:4.

12. A method for producing biodiesel, comprising contacting an amphipathic peptide-lipase conjugate in which an amphipathic peptide is fused to the N-terminus of a lipase with fat and/or oil together with alcohol,
   wherein the amphipathic peptide is NKC comprising amino acid sequence of SEQ ID NO:4.

\* \* \* \* \*

```
                       SEQUENCE LISTING

<160> NUMBER OF SEQ ID NOS: 91

<210> SEQ ID NO 1
   <211> LENGTH: 21
   <212> TYPE: PRT
   <213> ORGANISM: Artificial Sequence
   <220> FEATURE:
   <223> OTHER INFORMATION: Buforin IIb

<400> SEQUENCE: 1

Arg Ala Gly Leu Gln Phe Pro Val Gly Arg Leu Leu Arg Arg Leu Leu
   1               5                   10                  15

Arg Arg Leu Leu Arg
                   20

<210> SEQ ID NO 2
   <211> LENGTH: 9
   <212> TYPE: PRT
   <213> ORGANISM: Artificial Sequence
   <220> FEATURE:
   <223> OTHER INFORMATION: B0

<400> SEQUENCE: 2

Arg Ala Gly Leu Gln Phe Pro Val Gly
   1               5

<210> SEQ ID NO 3
   <211> LENGTH: 19
   <212> TYPE: PRT
   <213> ORGANISM: Artificial Sequence
   <220> FEATURE:
   <223> OTHER INFORMATION: Paracin I

<400> SEQUENCE: 3

Lys Gly Arg Gly Lys Gln Gly Gly Lys Val Arg Ala Lys Ala Lys Thr
   1               5                   10                  15

Arg Ser Ser

<210> SEQ ID NO 4
   <211> LENGTH: 19
   <212> TYPE: PRT
   <213> ORGANISM: Artificial Sequence
   <220> FEATURE:
   <223> OTHER INFORMATION: NKC
```

<400> SEQUENCE: 4

Ala Pro Lys Ala Met Lys Leu Leu Lys Lys Leu Leu Lys Leu Gln Lys
1               5                   10                  15

Lys Gly Ile

<210> SEQ ID NO 5
<211> LENGTH: 19
<212> TYPE: PRT
<213> ORGANISM: Artificial Sequence
<220> FEATURE:
<223> OTHER INFORMATION: NRC

<400> SEQUENCE: 5

Ala Pro Lys Ala Met Arg Leu Leu Arg Arg Leu Leu Arg Leu Gln Lys
1               5                   10                  15

Lys Gly Ile

<210> SEQ ID NO 6
<211> LENGTH: 476
<212> TYPE: PRT
<213> ORGANISM: Artificial Sequence
<220> FEATURE:
<223> OTHER INFORMATION: lipase TliA

<400> SEQUENCE: 6

Met Gly Val Phe Asp Tyr Lys Asn Leu Gly Thr Glu Ala Ser Lys Thr
1               5                   10                  15

Leu Phe Ala Asp Ala Thr Ala Ile Thr Leu Tyr Thr Tyr His Asn Leu
                20                  25                  30

Asp Asn Gly Phe Ala Val Gly Tyr Gln Gln His Gly Leu Gly Leu Gly
            35                  40                  45

Leu Pro Ala Thr Leu Val Gly Ala Leu Leu Gly Ser Thr Asp Ser Gln
        50                  55                  60

Gly Val Ile Pro Gly Ile Pro Trp Asn Pro Asp Ser Glu Lys Ala Ala
65                  70                  75                  80

Leu Asp Ala Val His Ala Ala Gly Trp Thr Pro Ile Ser Ala Ser Ala
                85                  90                  95

Leu Gly Tyr Gly Gly Lys Val Asp Ala Arg Gly Thr Phe Phe Gly Glu
            100                 105                 110

Lys Ala Gly Tyr Thr Thr Ala Gln Ala Glu Val Leu Gly Lys Tyr Asp
        115                 120                 125

Asp Ala Gly Lys Leu Leu Glu Ile Gly Ile Gly Phe Arg Gly Thr Ser
    130                 135                 140

Gly Pro Arg Glu Ser Leu Ile Thr Asp Ser Ile Gly Asp Leu Val Ser
145                 150                 155                 160

Asp Leu Leu Ala Ala Leu Gly Pro Lys Asp Tyr Ala Lys Asn Tyr Ala
                165                 170                 175

Gly Glu Ala Phe Gly Gly Leu Leu Lys Thr Val Ala Asp Tyr Ala Gly
            180                 185                 190

Ala His Gly Leu Ser Gly Lys Asp Val Leu Val Ser Gly His Ser Leu
        195                 200                 205

Gly Gly Leu Ala Val Asn Ser Met Ala Asp Leu Ser Thr Ser Lys Trp
    210                 215                 220

Ala Gly Phe Tyr Lys Asp Ala Asn Tyr Leu Ala Tyr Ala Ser Pro Thr
225                 230                 235                 240

Gln Ser Ala Gly Asp Lys Val Leu Asn Ile Gly Tyr Glu Asn Asp Pro
                245                 250                 255

Val Phe Arg Ala Leu Asp Gly Ser Thr Phe Asn Leu Ser Ser Leu Gly
        260                 265                 270

Val His Asp Lys Ala His Glu Ser Thr Thr Asp Asn Ile Val Ser Phe
        275                 280                 285

Asn Asp His Tyr Ala Ser Thr Leu Trp Asn Val Leu Pro Phe Ser Ile
        290                 295                 300

Ala Asn Leu Ser Thr Trp Val Ser His Leu Pro Ser Ala Tyr Gly Asp
305                 310                 315                 320

Gly Met Thr Arg Val Leu Glu Ser Gly Phe Tyr Glu Gln Met Thr Arg
                325                 330                 335

Asp Ser Thr Ile Ile Val Ala Asn Leu Ser Asp Pro Ala Arg Ala Asn
        340                 345                 350

Thr Trp Val Gln Asp Leu Asn Arg Asn Ala Glu Pro His Thr Gly Asn
        355                 360                 365

Thr Phe Ile Ile Gly Ser Asp Gly Asn Asp Leu Ile Gln Gly Gly Lys
        370                 375                 380

Gly Ala Asp Phe Ile Glu Gly Gly Lys Gly Asn Asp Thr Ile Arg Asp
385                 390                 395                 400

Asn Ser Gly His Asn Thr Phe Leu Phe Ser Gly His Phe Gly Gln Asp
                405                 410                 415

Arg Ile Ile Gly Tyr Gln Pro Thr Asp Arg Leu Val Phe Gln Gly Ala
        420                 425                 430

Asp Gly Ser Thr Asp Leu Arg Asp His Ala Lys Ala Val Gly Ala Asp
        435                 440                 445

Thr Val Leu Ser Phe Gly Ala Asp Ser Val Thr Leu Val Gly Val Gly
        450                 455                 460

Leu Gly Gly Leu Trp Ser Glu Gly Val Leu Ile Ser
465                 470                 475

<210> SEQ ID NO 7
<211> LENGTH: 340
<212> TYPE: PRT
<213> ORGANISM: Artificial Sequence
<220> FEATURE:
<223> OTHER INFORMATION: lipase M37

<400> SEQUENCE: 7

Met Ser Tyr Thr Lys Glu Gln Leu Met Leu Ala Phe Ser Tyr Met Ser
  1               5                  10                  15

Tyr Tyr Gly Ile Thr His Thr Gly Ser Ala Lys Lys Asn Ala Glu Leu
                20                  25                  30

Ile Leu Lys Lys Met Lys Glu Ala Leu Lys Thr Trp Lys Pro Phe Gln
        35                  40                  45

Glu Asp Asp Trp Glu Val Val Trp Gly Pro Ala Val Tyr Thr Met Pro
    50                  55                  60

Phe Thr Ile Phe Asn Asp Ala Met Met Tyr Val Ile Gln Lys Lys Gly
65                  70                  75                  80

Ala Glu Gly Glu Tyr Val Ile Ala Ile Arg Gly Thr Asn Pro Val Ser
                85                  90                  95

Ile Ser Asp Trp Leu Phe Asn Asp Phe Met Val Ser Ala Met Lys Lys
            100                 105                 110

Trp Pro Tyr Ala Ser Val Glu Gly Arg Ile Leu Lys Ile Ser Glu Ser
        115                 120                 125

Thr Ser Tyr Gly Leu Lys Thr Leu Gln Lys Leu Lys Pro Lys Ser His
    130                 135                 140

```
Ile Pro Gly Glu Asn Lys Thr Ile Leu Gln Phe Leu Asn Glu Lys Ile
145                 150                 155                 160

Gly Pro Glu Gly Lys Ala Lys Ile Cys Val Thr Gly His Ser Lys Gly
                165                 170                 175

Gly Ala Leu Ser Ser Thr Leu Ala Leu Trp Leu Lys Asp Ile Gln Gly
            180                 185                 190

Val Lys Leu Ser Gln Asn Ile Asp Ile Ser Thr Ile Pro Phe Ala Gly
        195                 200                 205

Pro Thr Ala Gly Asn Ala Asp Phe Ala Asp Tyr Phe Asp Asp Cys Leu
    210                 215                 220

Gly Asp Gln Cys Thr Arg Ile Ala Asn Ser Leu Asp Ile Val Pro Tyr
225                 230                 235                 240

Ala Trp Asn Thr Asn Ser Leu Lys Lys Leu Lys Ser Ile Tyr Ile Ser
                245                 250                 255

Glu Gln Ala Ser Val Lys Pro Leu Leu Tyr Gln Arg Ala Leu Ile Arg
            260                 265                 270

Ala Met Ile Ala Glu Thr Lys Gly Lys Lys Tyr Lys Gln Ile Lys Ala
        275                 280                 285

Glu Thr Pro Pro Leu Glu Gly Asn Ile Asn Pro Ile Leu Ile Glu Tyr
    290                 295                 300

Leu Val Gln Ala Ala Tyr Gln His Val Gly Tyr Pro Glu Leu Met
305                 310                 315                 320

Gly Met Met Asp Asp Ile Pro Leu Thr Asp Ile Phe Glu Asp Ala Ile
                325                 330                 335

Ala Gly Leu Leu
        340

<210> SEQ ID NO 8
<211> LENGTH: 497
<212> TYPE: PRT
<213> ORGANISM: Artificial Sequence
<220> FEATURE:
<223> OTHER INFORMATION: Buforin IIb - lipase TliA

<400> SEQUENCE: 8

Arg Ala Gly Leu Gln Phe Pro Val Gly Arg Leu Leu Arg Arg Leu Leu
1               5                   10                  15

Arg Arg Leu Leu Arg Met Gly Val Phe Asp Tyr Lys Asn Leu Gly Thr
                20                  25                  30

Glu Ala Ser Lys Thr Leu Phe Ala Asp Ala Thr Ala Ile Thr Leu Tyr
            35                  40                  45

Thr Tyr His Asn Leu Asp Asn Gly Phe Ala Val Gly Tyr Gln His
    50                  55                  60

Gly Leu Gly Leu Gly Leu Pro Ala Thr Leu Val Gly Ala Leu Leu Gly
65                  70                  75                  80

Ser Thr Asp Ser Gln Gly Val Ile Pro Gly Ile Pro Trp Asn Pro Asp
                85                  90                  95

Ser Glu Lys Ala Ala Leu Asp Ala Val His Ala Ala Gly Trp Thr Pro
            100                 105                 110

Ile Ser Ala Ser Ala Leu Gly Tyr Gly Gly Lys Val Asp Ala Arg Gly
        115                 120                 125

Thr Phe Phe Gly Glu Lys Ala Gly Tyr Thr Thr Ala Gln Ala Glu Val
    130                 135                 140

Leu Gly Lys Tyr Asp Asp Ala Gly Lys Leu Leu Glu Ile Gly Ile Gly
145                 150                 155                 160
```

```
Phe Arg Gly Thr Ser Gly Pro Arg Glu Ser Leu Ile Thr Asp Ser Ile
            165                 170                 175

Gly Asp Leu Val Ser Asp Leu Leu Ala Ala Leu Gly Pro Lys Asp Tyr
            180                 185                 190

Ala Lys Asn Tyr Ala Gly Glu Ala Phe Gly Gly Leu Leu Lys Thr Val
            195                 200                 205

Ala Asp Tyr Ala Gly Ala His Gly Leu Ser Gly Lys Asp Val Leu Val
210                 215                 220

Ser Gly His Ser Leu Gly Gly Leu Ala Val Asn Ser Met Ala Asp Leu
225                 230                 235                 240

Ser Thr Ser Lys Trp Ala Gly Phe Tyr Lys Asp Ala Asn Tyr Leu Ala
            245                 250                 255

Tyr Ala Ser Pro Thr Gln Ser Ala Gly Asp Lys Val Leu Asn Ile Gly
            260                 265                 270

Tyr Glu Asn Asp Pro Val Phe Arg Ala Leu Asp Gly Ser Thr Phe Asn
            275                 280                 285

Leu Ser Ser Leu Gly Val His Asp Lys Ala His Glu Ser Thr Thr Asp
            290                 295                 300

Asn Ile Val Ser Phe Asn Asp His Tyr Ala Ser Thr Leu Trp Asn Val
305                 310                 315                 320

Leu Pro Phe Ser Ile Ala Asn Leu Ser Thr Trp Val Ser His Leu Pro
            325                 330                 335

Ser Ala Tyr Gly Asp Gly Met Thr Arg Val Leu Glu Ser Gly Phe Tyr
            340                 345                 350

Glu Gln Met Thr Arg Asp Ser Thr Ile Ile Val Ala Asn Leu Ser Asp
            355                 360                 365

Pro Ala Arg Ala Asn Thr Trp Val Gln Asp Leu Asn Arg Asn Ala Glu
370                 375                 380

Pro His Thr Gly Asn Thr Phe Ile Ile Gly Ser Asp Gly Asn Asp Leu
385                 390                 395                 400

Ile Gln Gly Gly Lys Gly Ala Asp Phe Ile Glu Gly Gly Lys Gly Asn
            405                 410                 415

Asp Thr Ile Arg Asp Asn Ser Gly His Asn Thr Phe Leu Phe Ser Gly
            420                 425                 430

His Phe Gly Gln Asp Arg Ile Ile Gly Tyr Gln Pro Thr Asp Arg Leu
            435                 440                 445

Val Phe Gln Gly Ala Asp Gly Ser Thr Asp Leu Arg Asp His Ala Lys
450                 455                 460

Ala Val Gly Ala Asp Thr Val Leu Ser Phe Gly Ala Asp Ser Val Thr
465                 470                 475                 480

Leu Val Gly Val Gly Leu Gly Gly Leu Trp Ser Glu Gly Val Leu Ile
            485                 490                 495

Ser

<210> SEQ ID NO 9
<211> LENGTH: 485
<212> TYPE: PRT
<213> ORGANISM: Artificial Sequence
<220> FEATURE:
<223> OTHER INFORMATION: B0 - lipase TliA

<400> SEQUENCE: 9

Arg Ala Gly Leu Gln Phe Pro Val Gly Met Gly Val Phe Asp Tyr Lys
 1               5                  10                  15
```

-continued

```
Asn Leu Gly Thr Glu Ala Ser Lys Thr Leu Phe Ala Asp Ala Thr Ala
             20                  25                  30

Ile Thr Leu Tyr Thr Tyr His Asn Leu Asp Asn Gly Phe Ala Val Gly
         35                  40                  45

Tyr Gln Gln His Gly Leu Gly Leu Gly Leu Pro Ala Thr Leu Val Gly
     50                  55                  60

Ala Leu Leu Gly Ser Thr Asp Ser Gln Gly Val Ile Pro Gly Ile Pro
 65                  70                  75                  80

Trp Asn Pro Asp Ser Glu Lys Ala Ala Leu Asp Ala Val His Ala Ala
                 85                  90                  95

Gly Trp Thr Pro Ile Ser Ala Ser Ala Leu Gly Tyr Gly Gly Lys Val
            100                 105                 110

Asp Ala Arg Gly Thr Phe Phe Gly Glu Lys Ala Gly Tyr Thr Thr Ala
        115                 120                 125

Gln Ala Glu Val Leu Gly Lys Tyr Asp Asp Ala Gly Lys Leu Leu Glu
    130                 135                 140

Ile Gly Ile Gly Phe Arg Gly Thr Ser Gly Pro Arg Glu Ser Leu Ile
145                 150                 155                 160

Thr Asp Ser Ile Gly Asp Leu Val Ser Asp Leu Leu Ala Ala Leu Gly
                165                 170                 175

Pro Lys Asp Tyr Ala Lys Asn Tyr Ala Gly Glu Ala Phe Gly Gly Leu
            180                 185                 190

Leu Lys Thr Val Ala Asp Tyr Ala Gly Ala His Gly Leu Ser Gly Lys
        195                 200                 205

Asp Val Leu Val Ser Gly His Ser Leu Gly Gly Leu Ala Val Asn Ser
    210                 215                 220

Met Ala Asp Leu Ser Thr Ser Lys Trp Ala Gly Phe Tyr Lys Asp Ala
225                 230                 235                 240

Asn Tyr Leu Ala Tyr Ala Ser Pro Thr Gln Ser Ala Gly Asp Lys Val
                245                 250                 255

Leu Asn Ile Gly Tyr Glu Asn Asp Pro Val Phe Arg Ala Leu Asp Gly
            260                 265                 270

Ser Thr Phe Asn Leu Ser Ser Leu Gly Val His Asp Lys Ala His Glu
        275                 280                 285

Ser Thr Thr Asp Asn Ile Val Ser Phe Asn Asp His Tyr Ala Ser Thr
    290                 295                 300

Leu Trp Asn Val Leu Pro Phe Ser Ile Ala Asn Leu Ser Thr Trp Val
305                 310                 315                 320

Ser His Leu Pro Ser Ala Tyr Gly Asp Gly Met Thr Arg Val Leu Glu
                325                 330                 335

Ser Gly Phe Tyr Glu Gln Met Thr Arg Asp Ser Thr Ile Ile Val Ala
            340                 345                 350

Asn Leu Ser Asp Pro Ala Arg Ala Asn Thr Trp Val Gln Asp Leu Asn
        355                 360                 365

Arg Asn Ala Glu Pro His Thr Gly Asn Thr Phe Ile Ile Gly Ser Asp
    370                 375                 380

Gly Asn Asp Leu Ile Gln Gly Gly Lys Gly Ala Asp Phe Ile Glu Gly
385                 390                 395                 400

Gly Lys Gly Asn Asp Thr Ile Arg Asp Asn Ser Gly His Asn Thr Phe
                405                 410                 415

Leu Phe Ser Gly His Phe Gly Gln Asp Arg Ile Ile Gly Tyr Gln Pro
            420                 425                 430

Thr Asp Arg Leu Val Phe Gln Gly Ala Asp Gly Ser Thr Asp Leu Arg
```

```
                435                 440                 445
Asp His Ala Lys Ala Val Gly Ala Asp Thr Val Leu Ser Phe Gly Ala
    450                 455                 460

Asp Ser Val Thr Leu Val Gly Val Gly Leu Gly Leu Trp Ser Glu
465                 470                 475                 480

Gly Val Leu Ile Ser
            485

<210> SEQ ID NO 10
<211> LENGTH: 495
<212> TYPE: PRT
<213> ORGANISM: Artificial Sequence
<220> FEATURE:
<223> OTHER INFORMATION: Paracin I - lipase TliA

<400> SEQUENCE: 10

Lys Gly Arg Gly Lys Gln Gly Gly Lys Val Arg Ala Lys Ala Lys Thr
  1               5                  10                  15

Arg Ser Ser Met Gly Val Phe Asp Tyr Lys Asn Leu Gly Thr Glu Ala
             20                  25                  30

Ser Lys Thr Leu Phe Ala Asp Ala Thr Ala Ile Thr Leu Tyr Thr Tyr
         35                  40                  45

His Asn Leu Asp Asn Gly Phe Ala Val Gly Tyr Gln Gln His Gly Leu
     50                  55                  60

Gly Leu Gly Leu Pro Ala Thr Leu Val Gly Ala Leu Gly Ser Thr
 65                  70                  75                  80

Asp Ser Gln Gly Val Ile Pro Gly Ile Pro Trp Asn Pro Asp Ser Glu
                 85                  90                  95

Lys Ala Ala Leu Asp Ala Val His Ala Ala Gly Trp Thr Pro Ile Ser
            100                 105                 110

Ala Ser Ala Leu Gly Tyr Gly Gly Lys Val Asp Ala Arg Gly Thr Phe
        115                 120                 125

Phe Gly Glu Lys Ala Gly Tyr Thr Thr Ala Gln Ala Glu Val Leu Gly
    130                 135                 140

Lys Tyr Asp Asp Ala Gly Lys Leu Leu Glu Ile Gly Ile Gly Phe Arg
145                 150                 155                 160

Gly Thr Ser Gly Pro Arg Glu Ser Leu Ile Thr Asp Ser Ile Gly Asp
                165                 170                 175

Leu Val Ser Asp Leu Leu Ala Ala Leu Gly Pro Lys Asp Tyr Ala Lys
            180                 185                 190

Asn Tyr Ala Gly Glu Ala Phe Gly Gly Leu Leu Lys Thr Val Ala Asp
        195                 200                 205

Tyr Ala Gly Ala His Gly Leu Ser Gly Lys Asp Val Leu Val Ser Gly
    210                 215                 220

His Ser Leu Gly Gly Leu Ala Val Asn Ser Met Ala Asp Leu Ser Thr
225                 230                 235                 240

Ser Lys Trp Ala Gly Phe Tyr Lys Asp Ala Asn Tyr Leu Ala Tyr Ala
                245                 250                 255

Ser Pro Thr Gln Ser Ala Gly Asp Lys Val Leu Asn Ile Gly Tyr Glu
            260                 265                 270

Asn Asp Pro Val Phe Arg Ala Leu Asp Gly Ser Thr Phe Asn Leu Ser
        275                 280                 285

Ser Leu Gly Val His Asp Lys Ala His Glu Ser Thr Thr Asp Asn Ile
    290                 295                 300

Val Ser Phe Asn Asp His Tyr Ala Ser Thr Leu Trp Asn Val Leu Pro
```

```
            305                 310                 315                 320
    Phe Ser Ile Ala Asn Leu Ser Thr Trp Val Ser His Leu Pro Ser Ala
                    325                 330                 335

Tyr Gly Asp Gly Met Thr Arg Val Leu Glu Ser Gly Phe Tyr Glu Gln
                    340                 345                 350

Met Thr Arg Asp Ser Thr Ile Ile Val Ala Asn Leu Ser Asp Pro Ala
                    355                 360                 365

Arg Ala Asn Thr Trp Val Gln Asp Leu Asn Arg Asn Ala Glu Pro His
                    370                 375                 380

Thr Gly Asn Thr Phe Ile Ile Gly Ser Asp Gly Asn Asp Leu Ile Gln
    385                 390                 395                 400

Gly Gly Lys Gly Ala Asp Phe Ile Glu Gly Gly Lys Gly Asn Asp Thr
                    405                 410                 415

Ile Arg Asp Asn Ser Gly His Asn Thr Phe Leu Phe Ser Gly His Phe
                    420                 425                 430

Gly Gln Asp Arg Ile Ile Gly Tyr Gln Pro Thr Asp Arg Leu Val Phe
                    435                 440                 445

Gln Gly Ala Asp Gly Ser Thr Asp Leu Arg Asp His Ala Lys Ala Val
                    450                 455                 460

Gly Ala Asp Thr Val Leu Ser Phe Gly Ala Asp Ser Val Thr Leu Val
    465                 470                 475                 480

Gly Val Gly Leu Gly Gly Leu Trp Ser Glu Gly Val Leu Ile Ser
                    485                 490                 495

<210> SEQ ID NO 11
<211> LENGTH: 495
<212> TYPE: PRT
<213> ORGANISM: Artificial Sequence
<220> FEATURE:
<223> OTHER INFORMATION: NKC - lipase TliA

<400> SEQUENCE: 11

Ala Pro Lys Ala Met Lys Leu Leu Lys Lys Leu Leu Lys Leu Gln Lys
    1               5                   10                  15

Lys Gly Ile Met Gly Val Phe Asp Tyr Lys Asn Leu Gly Thr Glu Ala
                    20                  25                  30

Ser Lys Thr Leu Phe Ala Asp Ala Thr Ala Ile Thr Leu Tyr Thr Tyr
                    35                  40                  45

His Asn Leu Asp Asn Gly Phe Ala Val Gly Tyr Gln Gln His Gly Leu
                    50                  55                  60

Gly Leu Gly Leu Pro Ala Thr Leu Val Gly Ala Leu Leu Gly Ser Thr
    65                  70                  75                  80

Asp Ser Gln Gly Val Ile Pro Gly Ile Pro Trp Asn Pro Asp Ser Glu
                    85                  90                  95

Lys Ala Ala Leu Asp Ala Val His Ala Gly Trp Thr Pro Ile Ser
                    100                 105                 110

Ala Ser Ala Leu Gly Tyr Gly Gly Lys Val Asp Ala Arg Gly Thr Phe
                    115                 120                 125

Phe Gly Glu Lys Ala Gly Tyr Thr Thr Ala Gln Ala Glu Val Leu Gly
                    130                 135                 140

Lys Tyr Asp Asp Ala Gly Lys Leu Leu Glu Ile Gly Ile Gly Phe Arg
    145                 150                 155                 160

Gly Thr Ser Gly Pro Arg Glu Ser Leu Ile Thr Asp Ser Ile Gly Asp
                    165                 170                 175

Leu Val Ser Asp Leu Leu Ala Ala Leu Gly Pro Lys Asp Tyr Ala Lys
```

```
                180             185             190
Asn Tyr Ala Gly Glu Ala Phe Gly Gly Leu Leu Lys Thr Val Ala Asp
            195                 200                 205

Tyr Ala Gly Ala His Gly Leu Ser Gly Lys Asp Val Leu Val Ser Gly
210                 215                 220

His Ser Leu Gly Gly Leu Ala Val Asn Ser Met Ala Asp Leu Ser Thr
225                 230                 235                 240

Ser Lys Trp Ala Gly Phe Tyr Lys Asp Ala Asn Tyr Leu Ala Tyr Ala
            245                 250                 255

Ser Pro Thr Gln Ser Ala Gly Asp Lys Val Leu Asn Ile Gly Tyr Glu
            260                 265                 270

Asn Asp Pro Val Phe Arg Ala Leu Asp Gly Ser Thr Phe Asn Leu Ser
            275                 280                 285

Ser Leu Gly Val His Asp Lys Ala His Glu Ser Thr Thr Asp Asn Ile
            290                 295                 300

Val Ser Phe Asn Asp His Tyr Ala Ser Thr Leu Trp Asn Val Leu Pro
305                 310                 315                 320

Phe Ser Ile Ala Asn Leu Ser Thr Trp Val Ser His Leu Pro Ser Ala
                325                 330                 335

Tyr Gly Asp Gly Met Thr Arg Val Leu Glu Ser Gly Phe Tyr Glu Gln
            340                 345                 350

Met Thr Arg Asp Ser Thr Ile Ile Val Ala Asn Leu Ser Asp Pro Ala
            355                 360                 365

Arg Ala Asn Thr Trp Val Gln Asp Leu Asn Arg Asn Ala Glu Pro His
370                 375                 380

Thr Gly Asn Thr Phe Ile Ile Gly Ser Asp Gly Asn Asp Leu Ile Gln
385                 390                 395                 400

Gly Gly Lys Gly Ala Asp Phe Ile Glu Gly Gly Lys Gly Asn Asp Thr
                405                 410                 415

Ile Arg Asp Asn Ser Gly His Asn Thr Phe Leu Phe Ser Gly His Phe
                420                 425                 430

Gly Gln Asp Arg Ile Ile Gly Tyr Gln Pro Thr Asp Arg Leu Val Phe
            435                 440                 445

Gln Gly Ala Asp Gly Ser Thr Asp Leu Arg Asp His Ala Lys Ala Val
            450                 455                 460

Gly Ala Asp Thr Val Leu Ser Phe Gly Ala Asp Ser Val Thr Leu Val
465                 470                 475                 480

Gly Val Gly Leu Gly Gly Leu Trp Ser Glu Gly Val Leu Ile Ser
                485                 490                 495

<210> SEQ ID NO 12
<211> LENGTH: 495
<212> TYPE: PRT
<213> ORGANISM: Artificial Sequence
<220> FEATURE:
<223> OTHER INFORMATION: NRC - lipase TliA

<400> SEQUENCE: 12

Ala Pro Lys Ala Met Arg Leu Leu Arg Arg Leu Leu Arg Leu Gln Lys
1               5                   10                  15

Lys Gly Ile Met Gly Val Phe Asp Tyr Lys Asn Leu Gly Thr Glu Ala
            20                  25                  30

Ser Lys Thr Leu Phe Ala Asp Ala Thr Ala Ile Thr Leu Tyr Thr Tyr
        35                  40                  45

His Asn Leu Asp Asn Gly Phe Ala Val Gly Tyr Gln Gln His Gly Leu
```

```
                50                  55                  60
        Gly Leu Gly Leu Pro Ala Thr Leu Val Gly Ala Leu Leu Gly Ser Thr
         65                  70                  75                  80
        Asp Ser Gln Gly Val Ile Pro Gly Ile Pro Trp Asn Pro Asp Ser Glu
                             85                  90                  95
        Lys Ala Ala Leu Asp Ala Val His Ala Ala Gly Trp Thr Pro Ile Ser
                        100                 105                 110
        Ala Ser Ala Leu Gly Tyr Gly Lys Val Asp Ala Arg Gly Thr Phe
                    115                 120                 125
        Phe Gly Glu Lys Ala Gly Tyr Thr Thr Ala Gln Ala Glu Val Leu Gly
                130                 135                 140
        Lys Tyr Asp Asp Ala Gly Lys Leu Leu Glu Ile Gly Ile Gly Phe Arg
        145                 150                 155                 160
        Gly Thr Ser Gly Pro Arg Glu Ser Leu Ile Thr Asp Ser Ile Gly Asp
                             165                 170                 175
        Leu Val Ser Asp Leu Leu Ala Ala Leu Gly Pro Lys Asp Tyr Ala Lys
                        180                 185                 190
        Asn Tyr Ala Gly Glu Ala Phe Gly Gly Leu Leu Lys Thr Val Ala Asp
                    195                 200                 205
        Tyr Ala Gly Ala His Gly Leu Ser Gly Lys Asp Val Leu Val Ser Gly
                210                 215                 220
        His Ser Leu Gly Gly Leu Ala Val Asn Ser Met Ala Asp Leu Ser Thr
        225                 230                 235                 240
        Ser Lys Trp Ala Gly Phe Tyr Lys Asp Ala Asn Tyr Leu Ala Tyr Ala
                             245                 250                 255
        Ser Pro Thr Gln Ser Ala Gly Asp Lys Val Leu Asn Ile Gly Tyr Glu
                        260                 265                 270
        Asn Asp Pro Val Phe Arg Ala Leu Asp Gly Ser Thr Phe Asn Leu Ser
                    275                 280                 285
        Ser Leu Gly Val His Asp Lys Ala His Glu Ser Thr Thr Asp Asn Ile
                290                 295                 300
        Val Ser Phe Asn Asp His Tyr Ala Ser Thr Leu Trp Asn Val Leu Pro
        305                 310                 315                 320
        Phe Ser Ile Ala Asn Leu Ser Thr Trp Val Ser His Leu Pro Ser Ala
                             325                 330                 335
        Tyr Gly Asp Gly Met Thr Arg Val Leu Glu Ser Gly Phe Tyr Glu Gln
                        340                 345                 350
        Met Thr Arg Asp Ser Thr Ile Ile Val Ala Asn Leu Ser Asp Pro Ala
                    355                 360                 365
        Arg Ala Asn Thr Trp Val Gln Asp Leu Asn Arg Asn Ala Glu Pro His
                370                 375                 380
        Thr Gly Asn Thr Phe Ile Ile Gly Ser Asp Gly Asn Asp Leu Ile Gln
        385                 390                 395                 400
        Gly Gly Lys Gly Ala Asp Phe Ile Glu Gly Lys Gly Asn Asp Thr
                             405                 410                 415
        Ile Arg Asp Asn Ser Gly His Asn Thr Phe Leu Phe Ser Gly His Phe
                        420                 425                 430
        Gly Gln Asp Arg Ile Ile Gly Tyr Gln Pro Thr Asp Arg Leu Val Phe
                    435                 440                 445
        Gln Gly Ala Asp Gly Ser Thr Asp Leu Arg Asp His Ala Lys Ala Val
                450                 455                 460
        Gly Ala Asp Thr Val Leu Ser Phe Gly Ala Asp Ser Val Thr Leu Val
        465                 470                 475                 480
```

Gly Val Gly Leu Gly Gly Leu Trp Ser Glu Gly Val Leu Ile Ser
            485                 490                 495

<210> SEQ ID NO 13
<211> LENGTH: 361
<212> TYPE: PRT
<213> ORGANISM: Artificial Sequence
<220> FEATURE:
<223> OTHER INFORMATION: Buforin IIb - lipase M37

<400> SEQUENCE: 13

Arg Ala Gly Leu Gln Phe Pro Val Gly Arg Leu Leu Arg Arg Leu Leu
 1               5                  10                  15

Arg Arg Leu Leu Arg Met Ser Tyr Thr Lys Glu Gln Leu Met Leu Ala
                20                  25                  30

Phe Ser Tyr Met Ser Tyr Tyr Gly Ile Thr His Thr Gly Ser Ala Lys
            35                  40                  45

Lys Asn Ala Glu Leu Ile Leu Lys Lys Met Lys Glu Ala Leu Lys Thr
        50                  55                  60

Trp Lys Pro Phe Gln Glu Asp Asp Trp Glu Val Val Trp Gly Pro Ala
 65                  70                  75                  80

Val Tyr Thr Met Pro Phe Thr Ile Phe Asn Asp Ala Met Met Tyr Val
                85                  90                  95

Ile Gln Lys Lys Gly Ala Glu Gly Glu Tyr Val Ile Ala Ile Arg Gly
            100                 105                 110

Thr Asn Pro Val Ser Ile Ser Asp Trp Leu Phe Asn Asp Phe Met Val
        115                 120                 125

Ser Ala Met Lys Lys Trp Pro Tyr Ala Ser Val Glu Gly Arg Ile Leu
130                 135                 140

Lys Ile Ser Glu Ser Thr Ser Tyr Gly Leu Lys Thr Leu Gln Lys Leu
145                 150                 155                 160

Lys Pro Lys Ser His Ile Pro Gly Glu Asn Lys Thr Ile Leu Gln Phe
                165                 170                 175

Leu Asn Glu Lys Ile Gly Pro Glu Gly Lys Ala Lys Ile Cys Val Thr
            180                 185                 190

Gly His Ser Lys Gly Gly Ala Leu Ser Ser Thr Leu Ala Leu Trp Leu
        195                 200                 205

Lys Asp Ile Gln Gly Val Lys Leu Ser Gln Asn Ile Asp Ile Ser Thr
    210                 215                 220

Ile Pro Phe Ala Gly Pro Thr Ala Gly Asn Ala Asp Phe Ala Asp Tyr
225                 230                 235                 240

Phe Asp Asp Cys Leu Gly Asp Gln Cys Thr Arg Ile Ala Asn Ser Leu
                245                 250                 255

Asp Ile Val Pro Tyr Ala Trp Asn Thr Asn Ser Leu Lys Lys Leu Lys
            260                 265                 270

Ser Ile Tyr Ile Ser Glu Gln Ala Ser Val Lys Pro Leu Leu Tyr Gln
        275                 280                 285

Arg Ala Leu Ile Arg Ala Met Ile Ala Glu Thr Lys Gly Lys Lys Tyr
    290                 295                 300

Lys Gln Ile Lys Ala Glu Thr Pro Leu Glu Gly Asn Ile Asn Pro
305                 310                 315                 320

Ile Leu Ile Glu Tyr Leu Val Gln Ala Ala Tyr Gln His Val Val Gly
                325                 330                 335

Tyr Pro Glu Leu Met Gly Met Met Asp Asp Ile Pro Leu Thr Asp Ile
            340                 345                 350

```
Phe Glu Asp Ala Ile Ala Gly Leu Leu
        355                 360

<210> SEQ ID NO 14
<211> LENGTH: 349
<212> TYPE: PRT
<213> ORGANISM: Artificial Sequence
<220> FEATURE:
<223> OTHER INFORMATION: B0 - lipase M37

<400> SEQUENCE: 14

Arg Ala Gly Leu Gln Phe Pro Val Gly Met Ser Tyr Thr Lys Glu Gln
 1               5                  10                  15

Leu Met Leu Ala Phe Ser Tyr Met Ser Tyr Tyr Gly Ile Thr His Thr
                20                  25                  30

Gly Ser Ala Lys Lys Asn Ala Glu Leu Ile Leu Lys Lys Met Lys Glu
            35                  40                  45

Ala Leu Lys Thr Trp Lys Pro Phe Gln Glu Asp Asp Trp Glu Val Val
    50                  55                  60

Trp Gly Pro Ala Val Tyr Thr Met Pro Phe Thr Ile Phe Asn Asp Ala
 65                  70                  75                  80

Met Met Tyr Val Ile Gln Lys Lys Gly Ala Glu Gly Glu Tyr Val Ile
                85                  90                  95

Ala Ile Arg Gly Thr Asn Pro Val Ser Ile Ser Asp Trp Leu Phe Asn
            100                 105                 110

Asp Phe Met Val Ser Ala Met Lys Lys Trp Pro Tyr Ala Ser Val Glu
        115                 120                 125

Gly Arg Ile Leu Lys Ile Ser Glu Ser Thr Ser Tyr Gly Leu Lys Thr
130                 135                 140

Leu Gln Lys Leu Lys Pro Lys Ser His Ile Pro Gly Glu Asn Lys Thr
145                 150                 155                 160

Ile Leu Gln Phe Leu Asn Glu Lys Ile Gly Pro Glu Gly Lys Ala Lys
                165                 170                 175

Ile Cys Val Thr Gly His Ser Lys Gly Gly Ala Leu Ser Ser Thr Leu
            180                 185                 190

Ala Leu Trp Leu Lys Asp Ile Gln Gly Val Lys Leu Ser Gln Asn Ile
        195                 200                 205

Asp Ile Ser Thr Ile Pro Phe Ala Gly Pro Thr Ala Gly Asn Ala Asp
    210                 215                 220

Phe Ala Asp Tyr Phe Asp Asp Cys Leu Gly Asp Gln Cys Thr Arg Ile
225                 230                 235                 240

Ala Asn Ser Leu Asp Ile Val Pro Tyr Ala Trp Asn Thr Asn Ser Leu
                245                 250                 255

Lys Lys Leu Lys Ser Ile Tyr Ile Ser Glu Gln Ala Ser Val Lys Pro
            260                 265                 270

Leu Leu Tyr Gln Arg Ala Leu Ile Arg Ala Met Ile Ala Glu Thr Lys
        275                 280                 285

Gly Lys Lys Tyr Lys Gln Ile Lys Ala Glu Thr Pro Pro Leu Glu Gly
    290                 295                 300

Asn Ile Asn Pro Ile Leu Ile Glu Tyr Leu Val Gln Ala Ala Tyr Gln
305                 310                 315                 320

His Val Val Gly Tyr Pro Glu Leu Met Gly Met Met Asp Ile Pro
                325                 330                 335

Leu Thr Asp Ile Phe Glu Asp Ala Ile Ala Gly Leu Leu
            340                 345
```

```
<210> SEQ ID NO 15
<211> LENGTH: 359
<212> TYPE: PRT
<213> ORGANISM: Artificial Sequence
<220> FEATURE:
<223> OTHER INFORMATION: Paracin I - lipase M37

<400> SEQUENCE: 15
```

Lys Gly Arg Gly Lys Gln Gly Gly Lys Val Arg Ala Lys Ala Lys Thr
 1               5                  10                  15

Arg Ser Ser Met Ser Tyr Thr Lys Glu Gln Leu Met Leu Ala Phe Ser
            20                  25                  30

Tyr Met Ser Tyr Tyr Gly Ile Thr His Thr Gly Ser Ala Lys Lys Asn
        35                  40                  45

Ala Glu Leu Ile Leu Lys Lys Met Lys Glu Ala Leu Lys Thr Trp Lys
    50                  55                  60

Pro Phe Gln Glu Asp Asp Trp Glu Val Val Trp Gly Pro Ala Val Tyr
65                  70                  75                  80

Thr Met Pro Phe Thr Ile Phe Asn Asp Ala Met Met Tyr Val Ile Gln
                85                  90                  95

Lys Lys Gly Ala Glu Gly Glu Tyr Val Ile Ala Ile Arg Gly Thr Asn
            100                 105                 110

Pro Val Ser Ile Ser Asp Trp Leu Phe Asn Asp Phe Met Val Ser Ala
        115                 120                 125

Met Lys Lys Trp Pro Tyr Ala Ser Val Glu Gly Arg Ile Leu Lys Ile
    130                 135                 140

Ser Glu Ser Thr Ser Tyr Gly Leu Lys Thr Leu Gln Lys Leu Lys Pro
145                 150                 155                 160

Lys Ser His Ile Pro Gly Glu Asn Lys Thr Ile Leu Gln Phe Leu Asn
                165                 170                 175

Glu Lys Ile Gly Pro Glu Gly Lys Ala Lys Ile Cys Val Thr Gly His
            180                 185                 190

Ser Lys Gly Gly Ala Leu Ser Ser Thr Leu Ala Leu Trp Leu Lys Asp
        195                 200                 205

Ile Gln Gly Val Lys Leu Ser Gln Asn Ile Asp Ile Ser Thr Ile Pro
    210                 215                 220

Phe Ala Gly Pro Thr Ala Gly Asn Ala Asp Phe Ala Asp Tyr Phe Asp
225                 230                 235                 240

Asp Cys Leu Gly Asp Gln Cys Thr Arg Ile Ala Asn Ser Leu Asp Ile
                245                 250                 255

Val Pro Tyr Ala Trp Asn Thr Asn Ser Leu Lys Lys Leu Lys Ser Ile
            260                 265                 270

Tyr Ile Ser Glu Gln Ala Ser Val Lys Pro Leu Leu Tyr Gln Arg Ala
        275                 280                 285

Leu Ile Arg Ala Met Ile Ala Glu Thr Lys Gly Lys Lys Tyr Lys Gln
    290                 295                 300

Ile Lys Ala Glu Thr Pro Pro Leu Glu Gly Asn Ile Asn Pro Ile Leu
305                 310                 315                 320

Ile Glu Tyr Leu Val Gln Ala Ala Tyr Gln His Val Val Gly Tyr Pro
                325                 330                 335

Glu Leu Met Gly Met Met Asp Asp Ile Pro Leu Thr Asp Ile Phe Glu
            340                 345                 350

Asp Ala Ile Ala Gly Leu Leu
        355

<210> SEQ ID NO 16
<211> LENGTH: 359
<212> TYPE: PRT
<213> ORGANISM: Artificial Sequence
<220> FEATURE:
<223> OTHER INFORMATION: NKC - lipase M37

<400> SEQUENCE: 16

```
Ala Pro Lys Ala Met Lys Leu Leu Lys Lys Leu Leu Lys Leu Gln Lys
 1               5                  10                  15

Lys Gly Ile Met Ser Tyr Thr Lys Glu Gln Leu Met Leu Ala Phe Ser
            20                  25                  30

Tyr Met Ser Tyr Tyr Gly Ile Thr His Thr Gly Ser Ala Lys Lys Asn
        35                  40                  45

Ala Glu Leu Ile Leu Lys Lys Met Lys Glu Ala Leu Lys Thr Trp Lys
    50                  55                  60

Pro Phe Gln Glu Asp Asp Trp Glu Val Val Trp Gly Pro Ala Val Tyr
65                  70                  75                  80

Thr Met Pro Phe Thr Ile Phe Asn Asp Ala Met Met Tyr Val Ile Gln
                85                  90                  95

Lys Lys Gly Ala Glu Gly Glu Tyr Val Ile Ala Ile Arg Gly Thr Asn
            100                 105                 110

Pro Val Ser Ile Ser Asp Trp Leu Phe Asn Asp Phe Met Val Ser Ala
        115                 120                 125

Met Lys Lys Trp Pro Tyr Ala Ser Val Glu Gly Arg Ile Leu Lys Ile
    130                 135                 140

Ser Glu Ser Thr Ser Tyr Gly Leu Lys Thr Leu Gln Lys Leu Lys Pro
145                 150                 155                 160

Lys Ser His Ile Pro Gly Glu Asn Lys Thr Ile Leu Gln Phe Leu Asn
                165                 170                 175

Glu Lys Ile Gly Pro Glu Gly Lys Ala Lys Ile Cys Val Thr Gly His
            180                 185                 190

Ser Lys Gly Gly Ala Leu Ser Ser Thr Leu Ala Leu Trp Leu Lys Asp
        195                 200                 205

Ile Gln Gly Val Lys Leu Ser Gln Asn Ile Asp Ile Ser Thr Ile Pro
    210                 215                 220

Phe Ala Gly Pro Thr Ala Gly Asn Ala Asp Phe Ala Asp Tyr Phe Asp
225                 230                 235                 240

Asp Cys Leu Gly Asp Gln Cys Thr Arg Ile Ala Asn Ser Leu Asp Ile
                245                 250                 255

Val Pro Tyr Ala Trp Asn Thr Asn Ser Leu Lys Lys Leu Lys Ser Ile
            260                 265                 270

Tyr Ile Ser Glu Gln Ala Ser Val Lys Pro Leu Leu Tyr Gln Arg Ala
        275                 280                 285

Leu Ile Arg Ala Met Ile Ala Glu Thr Lys Gly Lys Lys Tyr Lys Gln
    290                 295                 300

Ile Lys Ala Glu Thr Pro Pro Leu Glu Gly Asn Ile Asn Pro Ile Leu
305                 310                 315                 320

Ile Glu Tyr Leu Val Gln Ala Ala Tyr Gln His Val Val Gly Tyr Pro
                325                 330                 335

Glu Leu Met Gly Met Met Asp Asp Ile Pro Leu Thr Asp Ile Phe Glu
            340                 345                 350

Asp Ala Ile Ala Gly Leu Leu
        355
```

<210> SEQ ID NO 17
<211> LENGTH: 359
<212> TYPE: PRT
<213> ORGANISM: Artificial Sequence
<220> FEATURE:
<223> OTHER INFORMATION: NRC - lipase M37

<400> SEQUENCE: 17

```
Ala Pro Lys Ala Met Arg Leu Leu Arg Arg Leu Leu Arg Leu Gln Lys
  1               5                  10                  15

Lys Gly Ile Met Ser Tyr Thr Lys Glu Gln Leu Met Leu Ala Phe Ser
             20                  25                  30

Tyr Met Ser Tyr Tyr Gly Ile Thr His Thr Gly Ser Ala Lys Lys Asn
         35                  40                  45

Ala Glu Leu Ile Leu Lys Lys Met Lys Glu Ala Leu Lys Thr Trp Lys
     50                  55                  60

Pro Phe Gln Glu Asp Asp Trp Glu Val Val Trp Gly Pro Ala Val Tyr
 65                  70                  75                  80

Thr Met Pro Phe Thr Ile Phe Asn Asp Ala Met Met Tyr Val Ile Gln
                 85                  90                  95

Lys Lys Gly Ala Glu Gly Glu Tyr Val Ile Ala Ile Arg Gly Thr Asn
            100                 105                 110

Pro Val Ser Ile Ser Asp Trp Leu Phe Asn Asp Phe Met Val Ser Ala
        115                 120                 125

Met Lys Lys Trp Pro Tyr Ala Ser Val Glu Gly Arg Ile Leu Lys Ile
    130                 135                 140

Ser Glu Ser Thr Ser Tyr Gly Leu Lys Thr Leu Gln Lys Leu Lys Pro
145                 150                 155                 160

Lys Ser His Ile Pro Gly Glu Asn Lys Thr Ile Leu Gln Phe Leu Asn
                165                 170                 175

Glu Lys Ile Gly Pro Glu Gly Lys Ala Lys Ile Cys Val Thr Gly His
            180                 185                 190

Ser Lys Gly Gly Ala Leu Ser Ser Thr Leu Ala Leu Trp Leu Lys Asp
        195                 200                 205

Ile Gln Gly Val Lys Leu Ser Gln Asn Ile Asp Ile Ser Thr Ile Pro
    210                 215                 220

Phe Ala Gly Pro Thr Ala Gly Asn Ala Asp Phe Ala Asp Tyr Phe Asp
225                 230                 235                 240

Asp Cys Leu Gly Asp Gln Cys Thr Arg Ile Ala Asn Ser Leu Asp Ile
                245                 250                 255

Val Pro Tyr Ala Trp Asn Thr Asn Ser Leu Lys Lys Leu Lys Ser Ile
            260                 265                 270

Tyr Ile Ser Glu Gln Ala Ser Val Lys Pro Leu Leu Tyr Gln Arg Ala
        275                 280                 285

Leu Ile Arg Ala Met Ile Ala Glu Thr Lys Gly Lys Lys Tyr Lys Gln
    290                 295                 300

Ile Lys Ala Glu Thr Pro Pro Leu Glu Gly Asn Ile Asn Pro Ile Leu
305                 310                 315                 320

Ile Glu Tyr Leu Val Gln Ala Ala Tyr Gln His Val Val Gly Tyr Pro
                325                 330                 335

Glu Leu Met Gly Met Met Asp Asp Ile Pro Leu Thr Asp Ile Phe Glu
            340                 345                 350

Asp Ala Ile Ala Gly Leu Leu
        355
```

<210> SEQ ID NO 18
<211> LENGTH: 497
<212> TYPE: PRT
<213> ORGANISM: Artificial Sequence
<220> FEATURE:
<223> OTHER INFORMATION: lipase TliA - Buforin IIb

<400> SEQUENCE: 18

```
Met Gly Val Phe Asp Tyr Lys Asn Leu Gly Thr Glu Ala Ser Lys Thr
 1               5                  10                  15

Leu Phe Ala Asp Ala Thr Ala Ile Thr Leu Tyr Thr Tyr His Asn Leu
             20                  25                  30

Asp Asn Gly Phe Ala Val Gly Tyr Gln Gln His Gly Leu Gly Leu Gly
         35                  40                  45

Leu Pro Ala Thr Leu Val Gly Ala Leu Leu Gly Ser Thr Asp Ser Gln
     50                  55                  60

Gly Val Ile Pro Gly Ile Pro Trp Asn Pro Asp Ser Glu Lys Ala Ala
 65                  70                  75                  80

Leu Asp Ala Val His Ala Ala Gly Trp Thr Pro Ile Ser Ala Ser Ala
                 85                  90                  95

Leu Gly Tyr Gly Gly Lys Val Asp Ala Arg Gly Thr Phe Phe Gly Glu
            100                 105                 110

Lys Ala Gly Tyr Thr Thr Ala Gln Ala Glu Val Leu Gly Lys Tyr Asp
        115                 120                 125

Asp Ala Gly Lys Leu Leu Glu Ile Gly Ile Gly Phe Arg Gly Thr Ser
    130                 135                 140

Gly Pro Arg Glu Ser Leu Ile Thr Asp Ser Ile Gly Asp Leu Val Ser
145                 150                 155                 160

Asp Leu Leu Ala Ala Leu Gly Pro Lys Asp Tyr Ala Lys Asn Tyr Ala
                165                 170                 175

Gly Glu Ala Phe Gly Gly Leu Leu Lys Thr Val Ala Asp Tyr Ala Gly
            180                 185                 190

Ala His Gly Leu Ser Gly Lys Asp Val Leu Val Ser Gly His Ser Leu
        195                 200                 205

Gly Gly Leu Ala Val Asn Ser Met Ala Asp Leu Ser Thr Ser Lys Trp
    210                 215                 220

Ala Gly Phe Tyr Lys Asp Ala Asn Tyr Leu Ala Tyr Ala Ser Pro Thr
225                 230                 235                 240

Gln Ser Ala Gly Asp Lys Val Leu Asn Ile Gly Tyr Glu Asn Asp Pro
                245                 250                 255

Val Phe Arg Ala Leu Asp Gly Ser Thr Phe Asn Leu Ser Ser Leu Gly
            260                 265                 270

Val His Asp Lys Ala His Glu Ser Thr Thr Asp Asn Ile Val Ser Phe
        275                 280                 285

Asn Asp His Tyr Ala Ser Thr Leu Trp Asn Val Leu Pro Phe Ser Ile
    290                 295                 300

Ala Asn Leu Ser Thr Trp Val Ser His Leu Pro Ser Ala Tyr Gly Asp
305                 310                 315                 320

Gly Met Thr Arg Val Leu Glu Ser Gly Phe Tyr Glu Gln Met Thr Arg
                325                 330                 335

Asp Ser Thr Ile Ile Val Ala Asn Leu Ser Asp Pro Ala Arg Ala Asn
            340                 345                 350

Thr Trp Val Gln Asp Leu Asn Arg Asn Ala Glu Pro His Thr Gly Asn
        355                 360                 365
```

```
Thr Phe Ile Ile Gly Ser Asp Gly Asn Asp Leu Ile Gln Gly Gly Lys
        370                 375                 380

Gly Ala Asp Phe Ile Glu Gly Gly Lys Gly Asn Asp Thr Ile Arg Asp
385                 390                 395                 400

Asn Ser Gly His Asn Thr Phe Leu Phe Ser Gly His Phe Gly Gln Asp
                405                 410                 415

Arg Ile Ile Gly Tyr Gln Pro Thr Asp Arg Leu Val Phe Gln Gly Ala
                420                 425                 430

Asp Gly Ser Thr Asp Leu Arg Asp His Ala Lys Ala Val Gly Ala Asp
                435                 440                 445

Thr Val Leu Ser Phe Gly Ala Asp Ser Val Thr Leu Val Gly Val Gly
        450                 455                 460

Leu Gly Gly Leu Trp Ser Glu Gly Val Leu Ile Ser Arg Ala Gly Leu
465                 470                 475                 480

Gln Phe Pro Val Gly Arg Leu Leu Arg Arg Leu Leu Arg Arg Leu Leu
                485                 490                 495

Arg
```

<210> SEQ ID NO 19
<211> LENGTH: 485
<212> TYPE: PRT
<213> ORGANISM: Artificial Sequence
<220> FEATURE:
<223> OTHER INFORMATION: lipase TliA - B0

<400> SEQUENCE: 19

```
Met Gly Val Phe Asp Tyr Lys Asn Leu Gly Thr Glu Ala Ser Lys Thr
1               5                   10                  15

Leu Phe Ala Asp Ala Thr Ala Ile Thr Leu Tyr Thr Tyr His Asn Leu
                20                  25                  30

Asp Asn Gly Phe Ala Val Gly Tyr Gln Gln His Gly Leu Gly Leu Gly
            35                  40                  45

Leu Pro Ala Thr Leu Val Gly Ala Leu Leu Gly Ser Thr Asp Ser Gln
        50                  55                  60

Gly Val Ile Pro Gly Ile Pro Trp Asn Pro Asp Ser Glu Lys Ala Ala
65                  70                  75                  80

Leu Asp Ala Val His Ala Ala Gly Trp Thr Pro Ile Ser Ala Ser Ala
                85                  90                  95

Leu Gly Tyr Gly Gly Lys Val Asp Ala Arg Gly Thr Phe Phe Gly Glu
            100                 105                 110

Lys Ala Gly Tyr Thr Thr Ala Gln Ala Glu Val Leu Gly Lys Tyr Asp
        115                 120                 125

Asp Ala Gly Lys Leu Leu Glu Ile Gly Ile Gly Phe Arg Gly Thr Ser
130                 135                 140

Gly Pro Arg Glu Ser Leu Ile Thr Asp Ser Ile Gly Asp Leu Val Ser
145                 150                 155                 160

Asp Leu Leu Ala Ala Leu Gly Pro Lys Asp Tyr Ala Lys Asn Tyr Ala
                165                 170                 175

Gly Glu Ala Phe Gly Gly Leu Leu Lys Thr Val Ala Asp Tyr Ala Gly
            180                 185                 190

Ala His Gly Leu Ser Gly Lys Asp Val Leu Val Ser Gly His Ser Leu
        195                 200                 205

Gly Gly Leu Ala Val Asn Ser Met Ala Asp Leu Ser Thr Ser Lys Trp
210                 215                 220
```

-continued

Ala Gly Phe Tyr Lys Asp Ala Asn Tyr Leu Ala Tyr Ala Ser Pro Thr
225                 230                 235                 240

Gln Ser Ala Gly Asp Lys Val Leu Asn Ile Gly Tyr Glu Asn Asp Pro
            245                 250                 255

Val Phe Arg Ala Leu Asp Gly Ser Thr Phe Asn Leu Ser Ser Leu Gly
        260                 265                 270

Val His Asp Lys Ala His Glu Ser Thr Thr Asp Asn Ile Val Ser Phe
    275                 280                 285

Asn Asp His Tyr Ala Ser Thr Leu Trp Asn Val Leu Pro Phe Ser Ile
290                 295                 300

Ala Asn Leu Ser Thr Trp Val Ser His Leu Pro Ser Ala Tyr Gly Asp
305                 310                 315                 320

Gly Met Thr Arg Val Leu Glu Ser Gly Phe Tyr Glu Gln Met Thr Arg
            325                 330                 335

Asp Ser Thr Ile Ile Val Ala Asn Leu Ser Asp Pro Ala Arg Ala Asn
        340                 345                 350

Thr Trp Val Gln Asp Leu Asn Arg Asn Ala Glu Pro His Thr Gly Asn
    355                 360                 365

Thr Phe Ile Ile Gly Ser Asp Gly Asn Asp Leu Ile Gln Gly Gly Lys
370                 375                 380

Gly Ala Asp Phe Ile Glu Gly Gly Lys Gly Asn Asp Thr Ile Arg Asp
385                 390                 395                 400

Asn Ser Gly His Asn Thr Phe Leu Phe Ser Gly His Phe Gly Gln Asp
            405                 410                 415

Arg Ile Ile Gly Tyr Gln Pro Thr Asp Arg Leu Val Phe Gln Gly Ala
        420                 425                 430

Asp Gly Ser Thr Asp Leu Arg Asp His Ala Lys Ala Val Gly Ala Asp
    435                 440                 445

Thr Val Leu Ser Phe Gly Ala Asp Ser Val Thr Leu Val Gly Val Gly
450                 455                 460

Leu Gly Gly Leu Trp Ser Glu Gly Val Leu Ile Ser Arg Ala Gly Leu
465                 470                 475                 480

Gln Phe Pro Val Gly
            485

<210> SEQ ID NO 20
<211> LENGTH: 495
<212> TYPE: PRT
<213> ORGANISM: Artificial Sequence
<220> FEATURE:
<223> OTHER INFORMATION: lipase TliA - Paracin I

<400> SEQUENCE: 20

Met Gly Val Phe Asp Tyr Lys Asn Leu Gly Thr Glu Ala Ser Lys Thr
1               5                   10                  15

Leu Phe Ala Asp Ala Thr Ala Ile Thr Leu Tyr Thr Tyr His Asn Leu
            20                  25                  30

Asp Asn Gly Phe Ala Val Gly Tyr Gln Gln His Gly Leu Gly Leu Gly
        35                  40                  45

Leu Pro Ala Thr Leu Val Gly Ala Leu Leu Gly Ser Thr Asp Ser Gln
    50                  55                  60

Gly Val Ile Pro Gly Ile Pro Trp Asn Pro Asp Ser Glu Lys Ala Ala
65                  70                  75                  80

Leu Asp Ala Val His Ala Gly Trp Thr Pro Ile Ser Ala Ser Ala
            85                  90                  95

Leu Gly Tyr Gly Gly Lys Val Asp Ala Arg Gly Thr Phe Phe Gly Glu
            100                 105                 110

Lys Ala Gly Tyr Thr Thr Ala Gln Ala Glu Val Leu Gly Lys Tyr Asp
        115                 120                 125

Asp Ala Gly Lys Leu Leu Glu Ile Gly Ile Gly Phe Arg Gly Thr Ser
    130                 135                 140

Gly Pro Arg Glu Ser Leu Ile Thr Asp Ser Ile Gly Asp Leu Val Ser
145                 150                 155                 160

Asp Leu Leu Ala Ala Leu Gly Pro Lys Asp Tyr Ala Lys Asn Tyr Ala
                165                 170                 175

Gly Glu Ala Phe Gly Leu Leu Lys Thr Val Ala Asp Tyr Ala Gly
            180                 185                 190

Ala His Gly Leu Ser Gly Lys Asp Val Leu Val Ser Gly His Ser Leu
        195                 200                 205

Gly Gly Leu Ala Val Asn Ser Met Ala Asp Leu Ser Thr Ser Lys Trp
    210                 215                 220

Ala Gly Phe Tyr Lys Asp Ala Asn Tyr Leu Ala Tyr Ala Ser Pro Thr
225                 230                 235                 240

Gln Ser Ala Gly Asp Lys Val Leu Asn Ile Gly Tyr Glu Asn Asp Pro
                245                 250                 255

Val Phe Arg Ala Leu Asp Gly Ser Thr Phe Asn Leu Ser Ser Leu Gly
            260                 265                 270

Val His Asp Lys Ala His Glu Ser Thr Thr Asp Asn Ile Val Ser Phe
        275                 280                 285

Asn Asp His Tyr Ala Ser Thr Leu Trp Asn Val Leu Pro Phe Ser Ile
    290                 295                 300

Ala Asn Leu Ser Thr Trp Val Ser His Leu Pro Ser Ala Tyr Gly Asp
305                 310                 315                 320

Gly Met Thr Arg Val Leu Glu Ser Gly Phe Tyr Glu Gln Met Thr Arg
                325                 330                 335

Asp Ser Thr Ile Ile Val Ala Asn Leu Ser Asp Pro Ala Arg Ala Asn
            340                 345                 350

Thr Trp Val Gln Asp Leu Asn Arg Asn Ala Glu Pro His Thr Gly Asn
        355                 360                 365

Thr Phe Ile Ile Gly Ser Asp Gly Asn Asp Leu Ile Gln Gly Gly Lys
    370                 375                 380

Gly Ala Asp Phe Ile Glu Gly Gly Lys Gly Asn Asp Thr Ile Arg Asp
385                 390                 395                 400

Asn Ser Gly His Asn Thr Phe Leu Phe Ser Gly His Phe Gly Gln Asp
                405                 410                 415

Arg Ile Ile Gly Tyr Gln Pro Thr Asp Arg Leu Val Phe Gln Gly Ala
            420                 425                 430

Asp Gly Ser Thr Asp Leu Arg Asp His Ala Lys Ala Val Gly Ala Asp
        435                 440                 445

Thr Val Leu Ser Phe Gly Ala Asp Ser Val Thr Leu Val Gly Val Gly
    450                 455                 460

Leu Gly Gly Leu Trp Ser Glu Gly Val Leu Ile Ser Lys Gly Arg Gly
465                 470                 475                 480

Lys Gln Gly Gly Lys Val Arg Ala Lys Ala Lys Thr Arg Ser Ser
                485                 490                 495

<210> SEQ ID NO 21
<211> LENGTH: 495
<212> TYPE: PRT

<213> ORGANISM: Artificial Sequence
<220> FEATURE:
<223> OTHER INFORMATION: lipase TliA - NKC

<400> SEQUENCE: 21

| | | | | | | | | | | | | | | |
|---|---|---|---|---|---|---|---|---|---|---|---|---|---|---|
| Met | Gly | Val | Phe | Asp | Tyr | Lys | Asn | Leu | Gly | Thr | Glu | Ala | Ser | Lys | Thr |
| 1 | | | | 5 | | | | | 10 | | | | | 15 | |
| Leu | Phe | Ala | Asp | Ala | Thr | Ala | Ile | Thr | Leu | Tyr | Thr | Tyr | His | Asn | Leu |
| | | | 20 | | | | | 25 | | | | | 30 | | |
| Asp | Asn | Gly | Phe | Ala | Val | Gly | Tyr | Gln | Gln | His | Gly | Leu | Gly | Leu | Gly |
| | | 35 | | | | | 40 | | | | | 45 | | | |
| Leu | Pro | Ala | Thr | Leu | Val | Gly | Ala | Leu | Leu | Gly | Ser | Thr | Asp | Ser | Gln |
| | 50 | | | | | 55 | | | | | 60 | | | | |
| Gly | Val | Ile | Pro | Gly | Ile | Pro | Trp | Asn | Pro | Asp | Ser | Glu | Lys | Ala | Ala |
| 65 | | | | | 70 | | | | | 75 | | | | | 80 |
| Leu | Asp | Ala | Val | His | Ala | Ala | Gly | Trp | Thr | Pro | Ile | Ser | Ala | Ser | Ala |
| | | | | 85 | | | | | 90 | | | | | 95 | |
| Leu | Gly | Tyr | Gly | Gly | Lys | Val | Asp | Ala | Arg | Gly | Thr | Phe | Phe | Gly | Glu |
| | | | 100 | | | | | 105 | | | | | 110 | | |
| Lys | Ala | Gly | Tyr | Thr | Thr | Ala | Gln | Ala | Glu | Val | Leu | Gly | Lys | Tyr | Asp |
| | | 115 | | | | | 120 | | | | | 125 | | | |
| Asp | Ala | Gly | Lys | Leu | Leu | Glu | Ile | Gly | Ile | Gly | Phe | Arg | Gly | Thr | Ser |
| | 130 | | | | | 135 | | | | | 140 | | | | |
| Gly | Pro | Arg | Glu | Ser | Leu | Ile | Thr | Asp | Ser | Ile | Gly | Asp | Leu | Val | Ser |
| 145 | | | | | 150 | | | | | 155 | | | | | 160 |
| Asp | Leu | Leu | Ala | Ala | Leu | Gly | Pro | Lys | Asp | Tyr | Ala | Lys | Asn | Tyr | Ala |
| | | | | 165 | | | | | 170 | | | | | 175 | |
| Gly | Glu | Ala | Phe | Gly | Gly | Leu | Leu | Lys | Thr | Val | Ala | Asp | Tyr | Ala | Gly |
| | | | 180 | | | | | 185 | | | | | 190 | | |
| Ala | His | Gly | Leu | Ser | Gly | Lys | Asp | Val | Leu | Val | Ser | Gly | His | Ser | Leu |
| | | 195 | | | | | 200 | | | | | 205 | | | |
| Gly | Gly | Leu | Ala | Val | Asn | Ser | Met | Ala | Asp | Leu | Ser | Thr | Ser | Lys | Trp |
| | 210 | | | | | 215 | | | | | 220 | | | | |
| Ala | Gly | Phe | Tyr | Lys | Asp | Ala | Asn | Tyr | Leu | Ala | Tyr | Ala | Ser | Pro | Thr |
| 225 | | | | | 230 | | | | | 235 | | | | | 240 |
| Gln | Ser | Ala | Gly | Asp | Lys | Val | Leu | Asn | Ile | Gly | Tyr | Glu | Asn | Asp | Pro |
| | | | | 245 | | | | | 250 | | | | | 255 | |
| Val | Phe | Arg | Ala | Leu | Asp | Gly | Ser | Thr | Phe | Asn | Leu | Ser | Ser | Leu | Gly |
| | | | 260 | | | | | 265 | | | | | 270 | | |
| Val | His | Asp | Lys | Ala | His | Glu | Ser | Thr | Thr | Asp | Asn | Ile | Val | Ser | Phe |
| | | 275 | | | | | 280 | | | | | 285 | | | |
| Asn | Asp | His | Tyr | Ala | Ser | Thr | Leu | Trp | Asn | Val | Leu | Pro | Phe | Ser | Ile |
| | 290 | | | | | 295 | | | | | 300 | | | | |
| Ala | Asn | Leu | Ser | Thr | Trp | Val | Ser | His | Leu | Pro | Ser | Ala | Tyr | Gly | Asp |
| 305 | | | | | 310 | | | | | 315 | | | | | 320 |
| Gly | Met | Thr | Arg | Val | Leu | Glu | Ser | Gly | Phe | Tyr | Glu | Gln | Met | Thr | Arg |
| | | | | 325 | | | | | 330 | | | | | 335 | |
| Asp | Ser | Thr | Ile | Ile | Val | Ala | Asn | Leu | Ser | Asp | Pro | Ala | Arg | Ala | Asn |
| | | | 340 | | | | | 345 | | | | | 350 | | |
| Thr | Trp | Val | Gln | Asp | Leu | Asn | Arg | Asn | Ala | Glu | Pro | His | Thr | Gly | Asn |
| | | 355 | | | | | 360 | | | | | 365 | | | |
| Thr | Phe | Ile | Ile | Gly | Ser | Asp | Gly | Asn | Asp | Leu | Ile | Gln | Gly | Gly | Lys |
| | 370 | | | | | 375 | | | | | 380 | | | | |
| Gly | Ala | Asp | Phe | Ile | Glu | Gly | Gly | Lys | Gly | Asn | Asp | Thr | Ile | Arg | Asp |

```
                385                 390                 395                 400
Asn Ser Gly His Asn Thr Phe Leu Phe Ser Gly His Phe Gly Gln Asp
                    405                 410                 415

Arg Ile Ile Gly Tyr Gln Pro Thr Asp Arg Leu Val Phe Gln Gly Ala
                420                 425                 430

Asp Gly Ser Thr Asp Leu Arg Asp His Ala Lys Ala Val Gly Ala Asp
            435                 440                 445

Thr Val Leu Ser Phe Gly Ala Asp Ser Val Thr Leu Val Gly Val Gly
        450                 455                 460

Leu Gly Gly Leu Trp Ser Glu Gly Val Leu Ile Ser Ala Pro Lys Ala
465                 470                 475                 480

Met Lys Leu Leu Lys Lys Leu Lys Leu Gln Lys Lys Gly Ile
                    485                 490                 495

<210> SEQ ID NO 22
<211> LENGTH: 495
<212> TYPE: PRT
<213> ORGANISM: Artificial Sequence
<220> FEATURE:
<223> OTHER INFORMATION: lipase TliA - NRC

<400> SEQUENCE: 22

Met Gly Val Phe Asp Tyr Lys Asn Leu Gly Thr Glu Ala Ser Lys Thr
1               5                   10                  15

Leu Phe Ala Asp Ala Thr Ala Ile Thr Leu Tyr Thr Tyr His Asn Leu
            20                  25                  30

Asp Asn Gly Phe Ala Val Gly Tyr Gln Gln His Gly Leu Gly Leu Gly
        35                  40                  45

Leu Pro Ala Thr Leu Val Gly Ala Leu Leu Gly Ser Thr Asp Ser Gln
    50                  55                  60

Gly Val Ile Pro Gly Ile Pro Trp Asn Pro Asp Ser Glu Lys Ala Ala
65                  70                  75                  80

Leu Asp Ala Val His Ala Ala Gly Trp Thr Pro Ile Ser Ala Ser Ala
                85                  90                  95

Leu Gly Tyr Gly Gly Lys Val Asp Ala Arg Gly Thr Phe Phe Gly Glu
            100                 105                 110

Lys Ala Gly Tyr Thr Thr Ala Gln Ala Glu Val Leu Gly Lys Tyr Asp
        115                 120                 125

Asp Ala Gly Lys Leu Leu Glu Ile Gly Ile Gly Phe Arg Gly Thr Ser
    130                 135                 140

Gly Pro Arg Glu Ser Leu Ile Thr Asp Ser Ile Gly Asp Leu Val Ser
145                 150                 155                 160

Asp Leu Leu Ala Ala Leu Gly Pro Lys Asp Tyr Ala Lys Asn Tyr Ala
                165                 170                 175

Gly Glu Ala Phe Gly Gly Leu Leu Lys Thr Val Ala Asp Tyr Ala Gly
            180                 185                 190

Ala His Gly Leu Ser Gly Lys Asp Val Leu Val Ser Gly His Ser Leu
        195                 200                 205

Gly Gly Leu Ala Val Asn Ser Met Ala Asp Leu Ser Thr Ser Lys Trp
    210                 215                 220

Ala Gly Phe Tyr Lys Asp Ala Asn Tyr Leu Ala Tyr Ala Ser Pro Thr
225                 230                 235                 240

Gln Ser Ala Gly Asp Lys Val Leu Asn Ile Gly Tyr Glu Asn Asp Pro
                245                 250                 255

Val Phe Arg Ala Leu Asp Gly Ser Thr Phe Asn Leu Ser Ser Leu Gly
```

```
                    260                 265                 270
Val His Asp Lys Ala His Glu Ser Thr Thr Asp Asn Ile Val Ser Phe
                275                 280                 285

Asn Asp His Tyr Ala Ser Thr Leu Trp Asn Val Leu Pro Phe Ser Ile
            290                 295                 300

Ala Asn Leu Ser Thr Trp Val Ser His Leu Pro Ser Ala Tyr Gly Asp
305                 310                 315                 320

Gly Met Thr Arg Val Leu Glu Ser Gly Phe Tyr Glu Gln Met Thr Arg
                325                 330                 335

Asp Ser Thr Ile Ile Val Ala Asn Leu Ser Asp Pro Ala Arg Ala Asn
            340                 345                 350

Thr Trp Val Gln Asp Leu Asn Arg Asn Ala Glu Pro His Thr Gly Asn
                355                 360                 365

Thr Phe Ile Ile Gly Ser Asp Gly Asn Asp Leu Ile Gln Gly Gly Lys
            370                 375                 380

Gly Ala Asp Phe Ile Glu Gly Gly Lys Gly Asn Asp Thr Ile Arg Asp
385                 390                 395                 400

Asn Ser Gly His Asn Thr Phe Leu Phe Ser Gly His Phe Gly Gln Asp
                405                 410                 415

Arg Ile Ile Gly Tyr Gln Pro Thr Asp Arg Leu Val Phe Gln Gly Ala
            420                 425                 430

Asp Gly Ser Thr Asp Leu Arg Asp His Ala Lys Ala Val Gly Ala Asp
                435                 440                 445

Thr Val Leu Ser Phe Gly Ala Asp Ser Val Thr Leu Val Gly Val Gly
            450                 455                 460

Leu Gly Gly Leu Trp Ser Glu Gly Val Leu Ile Ser Ala Pro Lys Ala
465                 470                 475                 480

Met Arg Leu Leu Arg Arg Leu Leu Arg Leu Gln Lys Lys Gly Ile
                485                 490                 495

<210> SEQ ID NO 23
<211> LENGTH: 361
<212> TYPE: PRT
<213> ORGANISM: Artificial Sequence
<220> FEATURE:
<223> OTHER INFORMATION: lipase M37- Buforin IIb

<400> SEQUENCE: 23

Met Ser Tyr Thr Lys Glu Gln Leu Met Leu Ala Phe Ser Tyr Met Ser
1               5                   10                  15

Tyr Tyr Gly Ile Thr His Thr Gly Ser Ala Lys Lys Asn Ala Glu Leu
            20                  25                  30

Ile Leu Lys Lys Met Lys Glu Ala Leu Lys Thr Trp Lys Pro Phe Gln
        35                  40                  45

Glu Asp Asp Trp Glu Val Val Trp Gly Pro Ala Val Tyr Thr Met Pro
    50                  55                  60

Phe Thr Ile Phe Asn Asp Ala Met Met Tyr Val Ile Gln Lys Lys Gly
65                  70                  75                  80

Ala Glu Gly Glu Tyr Val Ile Ala Ile Arg Gly Thr Asn Pro Val Ser
                85                  90                  95

Ile Ser Asp Trp Leu Phe Asn Asp Phe Met Val Ser Ala Met Lys Lys
            100                 105                 110

Trp Pro Tyr Ala Ser Val Glu Gly Arg Ile Leu Lys Ile Ser Glu Ser
        115                 120                 125

Thr Ser Tyr Gly Leu Lys Thr Leu Gln Lys Leu Lys Pro Lys Ser His
```

```
            130                 135                 140
Ile Pro Gly Glu Asn Lys Thr Ile Leu Gln Phe Leu Asn Glu Lys Ile
145                 150                 155                 160

Gly Pro Glu Gly Lys Ala Lys Ile Cys Val Thr Gly His Ser Lys Gly
                165                 170                 175

Gly Ala Leu Ser Ser Thr Leu Ala Leu Trp Leu Lys Asp Ile Gln Gly
                180                 185                 190

Val Lys Leu Ser Gln Asn Ile Asp Ile Ser Thr Ile Pro Phe Ala Gly
                195                 200                 205

Pro Thr Ala Gly Asn Ala Asp Phe Ala Asp Tyr Phe Asp Asp Cys Leu
                210                 215                 220

Gly Asp Gln Cys Thr Arg Ile Ala Asn Ser Leu Asp Ile Val Pro Tyr
225                 230                 235                 240

Ala Trp Asn Thr Asn Ser Leu Lys Lys Leu Lys Ser Ile Tyr Ile Ser
                245                 250                 255

Glu Gln Ala Ser Val Lys Pro Leu Leu Tyr Gln Arg Ala Leu Ile Arg
                260                 265                 270

Ala Met Ile Ala Glu Thr Lys Gly Lys Lys Tyr Lys Gln Ile Lys Ala
                275                 280                 285

Glu Thr Pro Pro Leu Glu Gly Asn Ile Asn Pro Ile Leu Ile Glu Tyr
                290                 295                 300

Leu Val Gln Ala Ala Tyr Gln His Val Val Gly Tyr Pro Glu Leu Met
305                 310                 315                 320

Gly Met Met Asp Asp Ile Pro Leu Thr Asp Ile Phe Glu Asp Ala Ile
                325                 330                 335

Ala Gly Leu Leu Arg Ala Gly Leu Gln Phe Pro Val Gly Arg Leu Leu
                340                 345                 350

Arg Arg Leu Leu Arg Arg Leu Leu Arg
                355                 360

<210> SEQ ID NO 24
<211> LENGTH: 349
<212> TYPE: PRT
<213> ORGANISM: Artificial Sequence
<220> FEATURE:
<223> OTHER INFORMATION: lipase M37 - B0

<400> SEQUENCE: 24

Met Ser Tyr Thr Lys Glu Gln Leu Met Leu Ala Phe Ser Tyr Met Ser
  1               5                  10                  15

Tyr Tyr Gly Ile Thr His Thr Gly Ser Ala Lys Lys Asn Ala Glu Leu
                 20                  25                  30

Ile Leu Lys Lys Met Lys Glu Ala Leu Lys Thr Trp Lys Pro Phe Gln
             35                  40                  45

Glu Asp Asp Trp Glu Val Val Trp Gly Pro Ala Val Tyr Thr Met Pro
         50                  55                  60

Phe Thr Ile Phe Asn Asp Ala Met Met Tyr Val Ile Gln Lys Lys Gly
 65                  70                  75                  80

Ala Glu Gly Glu Tyr Val Ile Ala Ile Arg Gly Thr Asn Pro Val Ser
                 85                  90                  95

Ile Ser Asp Trp Leu Phe Asn Asp Phe Met Val Ser Ala Met Lys Lys
                100                 105                 110

Trp Pro Tyr Ala Ser Val Glu Gly Arg Ile Leu Lys Ile Ser Glu Ser
             115                 120                 125

Thr Ser Tyr Gly Leu Lys Thr Leu Gln Lys Leu Lys Pro Lys Ser His
```

```
            130                 135                 140
Ile Pro Gly Glu Asn Lys Thr Ile Leu Gln Phe Leu Asn Glu Lys Ile
145                 150                 155                 160

Gly Pro Glu Gly Lys Ala Lys Ile Cys Val Thr Gly His Ser Lys Gly
                165                 170                 175

Gly Ala Leu Ser Ser Thr Leu Ala Leu Trp Leu Lys Asp Ile Gln Gly
                180                 185                 190

Val Lys Leu Ser Gln Asn Ile Asp Ile Ser Thr Ile Pro Phe Ala Gly
                195                 200                 205

Pro Thr Ala Gly Asn Ala Asp Phe Ala Asp Tyr Phe Asp Asp Cys Leu
            210                 215                 220

Gly Asp Gln Cys Thr Arg Ile Ala Asn Ser Leu Asp Ile Val Pro Tyr
225                 230                 235                 240

Ala Trp Asn Thr Asn Ser Leu Lys Lys Leu Lys Ser Ile Tyr Ile Ser
                245                 250                 255

Glu Gln Ala Ser Val Lys Pro Leu Leu Tyr Gln Arg Ala Leu Ile Arg
                260                 265                 270

Ala Met Ile Ala Glu Thr Lys Gly Lys Lys Tyr Lys Gln Ile Lys Ala
                275                 280                 285

Glu Thr Pro Pro Leu Glu Gly Asn Ile Asn Pro Ile Leu Ile Glu Tyr
            290                 295                 300

Leu Val Gln Ala Ala Tyr Gln His Val Val Gly Tyr Pro Glu Leu Met
305                 310                 315                 320

Gly Met Met Asp Asp Ile Pro Leu Thr Asp Ile Phe Glu Asp Ala Ile
                325                 330                 335

Ala Gly Leu Leu Arg Ala Gly Leu Gln Phe Pro Val Gly
                340                 345

<210> SEQ ID NO 25
<211> LENGTH: 359
<212> TYPE: PRT
<213> ORGANISM: Artificial Sequence
<220> FEATURE:
<223> OTHER INFORMATION: lipase M37 - Paracin I

<400> SEQUENCE: 25

Met Ser Tyr Thr Lys Glu Gln Leu Met Leu Ala Phe Ser Tyr Met Ser
1               5                   10                  15

Tyr Tyr Gly Ile Thr His Thr Gly Ser Ala Lys Lys Asn Ala Glu Leu
                20                  25                  30

Ile Leu Lys Lys Met Lys Glu Ala Leu Lys Thr Trp Lys Pro Phe Gln
            35                  40                  45

Glu Asp Asp Trp Glu Val Val Trp Gly Pro Ala Val Tyr Thr Met Pro
        50                  55                  60

Phe Thr Ile Phe Asn Asp Ala Met Met Tyr Val Ile Gln Lys Lys Gly
65                  70                  75                  80

Ala Glu Gly Glu Tyr Val Ile Ala Ile Arg Gly Thr Asn Pro Val Ser
                85                  90                  95

Ile Ser Asp Trp Leu Phe Asn Asp Phe Met Val Ser Ala Met Lys Lys
                100                 105                 110

Trp Pro Tyr Ala Ser Val Glu Gly Arg Ile Leu Lys Ile Ser Glu Ser
            115                 120                 125

Thr Ser Tyr Gly Leu Lys Thr Leu Gln Lys Leu Lys Pro Lys Ser His
            130                 135                 140

Ile Pro Gly Glu Asn Lys Thr Ile Leu Gln Phe Leu Asn Glu Lys Ile
```

```
            145                 150                 155                 160
        Gly Pro Glu Gly Lys Ala Lys Ile Cys Val Thr Gly His Ser Lys Gly
                        165                 170                 175

Gly Ala Leu Ser Ser Thr Leu Ala Leu Trp Leu Lys Asp Ile Gln Gly
                        180                 185                 190

Val Lys Leu Ser Gln Asn Ile Asp Ile Ser Thr Ile Pro Phe Ala Gly
                        195                 200                 205

Pro Thr Ala Gly Asn Ala Asp Phe Ala Asp Tyr Phe Asp Asp Cys Leu
                        210                 215                 220

Gly Asp Gln Cys Thr Arg Ile Ala Asn Ser Leu Asp Ile Val Pro Tyr
        225                 230                 235                 240

Ala Trp Asn Thr Asn Ser Leu Lys Lys Leu Lys Ser Ile Tyr Ile Ser
                        245                 250                 255

Glu Gln Ala Ser Val Lys Pro Leu Leu Tyr Gln Arg Ala Leu Ile Arg
                        260                 265                 270

Ala Met Ile Ala Glu Thr Lys Gly Lys Lys Tyr Lys Gln Ile Lys Ala
                        275                 280                 285

Glu Thr Pro Pro Leu Glu Gly Asn Ile Asn Pro Ile Leu Ile Glu Tyr
                        290                 295                 300

Leu Val Gln Ala Ala Tyr Gln His Val Val Gly Tyr Pro Glu Leu Met
        305                 310                 315                 320

Gly Met Met Asp Asp Ile Pro Leu Thr Asp Ile Phe Glu Asp Ala Ile
                        325                 330                 335

Ala Gly Leu Leu Lys Gly Arg Gly Lys Gln Gly Gly Lys Val Arg Ala
                        340                 345                 350

Lys Ala Lys Thr Arg Ser Ser
                        355

<210> SEQ ID NO 26
<211> LENGTH: 359
<212> TYPE: PRT
<213> ORGANISM: Artificial Sequence
<220> FEATURE:
<223> OTHER INFORMATION: lipase M37 - NKC

<400> SEQUENCE: 26

Met Ser Tyr Thr Lys Glu Gln Leu Met Leu Ala Phe Ser Tyr Met Ser
        1               5                   10                  15

Tyr Tyr Gly Ile Thr His Thr Gly Ser Ala Lys Lys Asn Ala Glu Leu
                        20                  25                  30

Ile Leu Lys Lys Met Lys Glu Ala Leu Lys Thr Trp Lys Pro Phe Gln
                        35                  40                  45

Glu Asp Asp Trp Glu Val Val Trp Gly Pro Ala Val Tyr Thr Met Pro
                50                  55                  60

Phe Thr Ile Phe Asn Asp Ala Met Met Tyr Val Ile Gln Lys Lys Gly
        65                  70                  75                  80

Ala Glu Gly Glu Tyr Val Ile Ala Ile Arg Gly Thr Asn Pro Val Ser
                        85                  90                  95

Ile Ser Asp Trp Leu Phe Asn Asp Phe Met Val Ser Ala Met Lys Lys
                        100                 105                 110

Trp Pro Tyr Ala Ser Val Glu Gly Arg Ile Leu Lys Ile Ser Glu Ser
                        115                 120                 125

Thr Ser Tyr Gly Leu Lys Thr Leu Gln Lys Leu Lys Pro Lys Ser His
                        130                 135                 140

Ile Pro Gly Glu Asn Lys Thr Ile Leu Gln Phe Leu Asn Glu Lys Ile
```

```
                145                 150                 155                 160
        Gly Pro Glu Gly Lys Ala Lys Ile Cys Val Thr Gly His Ser Lys Gly
                        165                 170                 175

Gly Ala Leu Ser Ser Thr Leu Ala Leu Trp Leu Lys Asp Ile Gln Gly
                    180                 185                 190

Val Lys Leu Ser Gln Asn Ile Asp Ile Ser Thr Ile Pro Phe Ala Gly
                195                 200                 205

Pro Thr Ala Gly Asn Ala Asp Phe Ala Asp Tyr Phe Asp Asp Cys Leu
            210                 215                 220

Gly Asp Gln Cys Thr Arg Ile Ala Asn Ser Leu Asp Ile Val Pro Tyr
        225                 230                 235                 240

Ala Trp Asn Thr Asn Ser Leu Lys Lys Leu Lys Ser Ile Tyr Ile Ser
                        245                 250                 255

Glu Gln Ala Ser Val Lys Pro Leu Leu Tyr Gln Arg Ala Leu Ile Arg
                    260                 265                 270

Ala Met Ile Ala Glu Thr Lys Gly Lys Lys Tyr Lys Gln Ile Lys Ala
                275                 280                 285

Glu Thr Pro Pro Leu Glu Gly Asn Ile Asn Pro Ile Leu Ile Glu Tyr
            290                 295                 300

Leu Val Gln Ala Ala Tyr Gln His Val Val Gly Tyr Pro Glu Leu Met
        305                 310                 315                 320

Gly Met Met Asp Asp Ile Pro Leu Thr Asp Ile Phe Glu Asp Ala Ile
                        325                 330                 335

Ala Gly Leu Leu Ala Pro Lys Ala Met Lys Leu Leu Lys Lys Leu Leu
                    340                 345                 350

Lys Leu Gln Lys Lys Gly Ile
                355

<210> SEQ ID NO 27
<211> LENGTH: 359
<212> TYPE: PRT
<213> ORGANISM: Artificial Sequence
<220> FEATURE:
<223> OTHER INFORMATION: lipase M37 - NRC

<400> SEQUENCE: 27

Met Ser Tyr Thr Lys Glu Gln Leu Met Leu Ala Phe Ser Tyr Met Ser
        1               5                   10                  15

Tyr Tyr Gly Ile Thr His Thr Gly Ser Ala Lys Lys Asn Ala Glu Leu
                    20                  25                  30

Ile Leu Lys Lys Met Lys Glu Ala Leu Lys Thr Trp Lys Pro Phe Gln
                35                  40                  45

Glu Asp Asp Trp Glu Val Val Trp Gly Pro Ala Val Tyr Thr Met Pro
            50                  55                  60

Phe Thr Ile Phe Asn Asp Ala Met Met Tyr Val Ile Gln Lys Lys Gly
        65                  70                  75                  80

Ala Glu Gly Glu Tyr Val Ile Ala Ile Arg Gly Thr Asn Pro Val Ser
                        85                  90                  95

Ile Ser Asp Trp Leu Phe Asn Asp Phe Met Val Ser Ala Met Lys Lys
                    100                 105                 110

Trp Pro Tyr Ala Ser Val Glu Gly Arg Ile Leu Lys Ile Ser Glu Ser
                115                 120                 125

Thr Ser Tyr Gly Leu Lys Thr Leu Gln Lys Leu Lys Pro Lys Ser His
            130                 135                 140

Ile Pro Gly Glu Asn Lys Thr Ile Leu Gln Phe Leu Asn Glu Lys Ile
```

```
                145                 150                 155                 160
Gly Pro Glu Gly Lys Ala Lys Ile Cys Val Thr Gly His Ser Lys Gly
                165                 170                 175
Gly Ala Leu Ser Ser Thr Leu Ala Leu Trp Leu Lys Asp Ile Gln Gly
                180                 185                 190
Val Lys Leu Ser Gln Asn Ile Asp Ile Ser Thr Ile Pro Phe Ala Gly
                195                 200                 205
Pro Thr Ala Gly Asn Ala Asp Phe Ala Asp Tyr Phe Asp Asp Cys Leu
                210                 215                 220
Gly Asp Gln Cys Thr Arg Ile Ala Asn Ser Leu Asp Ile Val Pro Tyr
225                 230                 235                 240
Ala Trp Asn Thr Asn Ser Leu Lys Lys Leu Lys Ser Ile Tyr Ile Ser
                245                 250                 255
Glu Gln Ala Ser Val Lys Pro Leu Leu Tyr Gln Arg Ala Leu Ile Arg
                260                 265                 270
Ala Met Ile Ala Glu Thr Lys Gly Lys Lys Tyr Lys Gln Ile Lys Ala
                275                 280                 285
Glu Thr Pro Pro Leu Glu Gly Asn Ile Asn Pro Ile Leu Ile Glu Tyr
                290                 295                 300
Leu Val Gln Ala Ala Tyr Gln His Val Val Gly Tyr Pro Glu Leu Met
305                 310                 315                 320
Gly Met Met Asp Asp Ile Pro Leu Thr Asp Ile Phe Glu Asp Ala Ile
                325                 330                 335
Ala Gly Leu Leu Ala Pro Lys Ala Met Arg Leu Leu Arg Arg Leu Leu
                340                 345                 350
Arg Leu Gln Lys Lys Gly Ile
                355

<210> SEQ ID NO 28
<211> LENGTH: 518
<212> TYPE: PRT
<213> ORGANISM: Artificial Sequence
<220> FEATURE:
<223> OTHER INFORMATION: Buforin IIb - lipase TliA - Buforin IIb

<400> SEQUENCE: 28

Arg Ala Gly Leu Gln Phe Pro Val Gly Arg Leu Leu Arg Arg Leu Leu
1               5                   10                  15
Arg Arg Leu Leu Arg Met Gly Val Phe Asp Tyr Lys Asn Leu Gly Thr
                20                  25                  30
Glu Ala Ser Lys Thr Leu Phe Ala Asp Ala Thr Ala Ile Thr Leu Tyr
            35                  40                  45
Thr Tyr His Asn Leu Asp Asn Gly Phe Ala Val Gly Tyr Gln Gln His
        50                  55                  60
Gly Leu Gly Leu Gly Leu Pro Ala Thr Leu Val Gly Ala Leu Leu Gly
65                  70                  75                  80
Ser Thr Asp Ser Gln Gly Val Ile Pro Gly Ile Pro Trp Asn Pro Asp
                85                  90                  95
Ser Glu Lys Ala Ala Leu Asp Ala Val His Ala Ala Gly Trp Thr Pro
                100                 105                 110
Ile Ser Ala Ser Ala Leu Gly Tyr Gly Gly Lys Val Asp Ala Arg Gly
                115                 120                 125
Thr Phe Phe Gly Glu Lys Ala Gly Tyr Thr Thr Ala Gln Ala Glu Val
                130                 135                 140
Leu Gly Lys Tyr Asp Asp Ala Gly Lys Leu Leu Glu Ile Gly Ile Gly
```

```
            145                 150                 155                 160
        Phe Arg Gly Thr Ser Gly Pro Arg Glu Ser Leu Ile Thr Asp Ser Ile
                        165                 170                 175
        Gly Asp Leu Val Ser Asp Leu Leu Ala Ala Leu Gly Pro Lys Asp Tyr
                        180                 185                 190
        Ala Lys Asn Tyr Ala Gly Glu Ala Phe Gly Gly Leu Leu Lys Thr Val
                        195                 200                 205
        Ala Asp Tyr Ala Gly Ala His Gly Leu Ser Gly Lys Asp Val Leu Val
                210                 215                 220
        Ser Gly His Ser Leu Gly Gly Leu Ala Val Asn Ser Met Ala Asp Leu
        225                 230                 235                 240
        Ser Thr Ser Lys Trp Ala Gly Phe Tyr Lys Asp Ala Asn Tyr Leu Ala
                        245                 250                 255
        Tyr Ala Ser Pro Thr Gln Ser Ala Gly Asp Lys Val Leu Asn Ile Gly
                        260                 265                 270
        Tyr Glu Asn Asp Pro Val Phe Arg Ala Leu Asp Gly Ser Thr Phe Asn
                        275                 280                 285
        Leu Ser Ser Leu Gly Val His Asp Lys Ala His Glu Ser Thr Thr Asp
                290                 295                 300
        Asn Ile Val Ser Phe Asn Asp His Tyr Ala Ser Thr Leu Trp Asn Val
        305                 310                 315                 320
        Leu Pro Phe Ser Ile Ala Asn Leu Ser Thr Trp Val Ser His Leu Pro
                        325                 330                 335
        Ser Ala Tyr Gly Asp Gly Met Thr Arg Val Leu Glu Ser Gly Phe Tyr
                        340                 345                 350
        Glu Gln Met Thr Arg Asp Ser Thr Ile Ile Val Ala Asn Leu Ser Asp
                        355                 360                 365
        Pro Ala Arg Ala Asn Thr Trp Val Gln Asp Leu Asn Arg Asn Ala Glu
                        370                 375                 380
        Pro His Thr Gly Asn Thr Phe Ile Ile Gly Ser Asp Gly Asn Asp Leu
        385                 390                 395                 400
        Ile Gln Gly Gly Lys Gly Ala Asp Phe Ile Glu Gly Gly Lys Gly Asn
                        405                 410                 415
        Asp Thr Ile Arg Asp Asn Ser Gly His Asn Thr Phe Leu Phe Ser Gly
                        420                 425                 430
        His Phe Gly Gln Asp Arg Ile Ile Gly Tyr Gln Pro Thr Asp Arg Leu
                        435                 440                 445
        Val Phe Gln Gly Ala Asp Gly Ser Thr Asp Leu Arg Asp His Ala Lys
                        450                 455                 460
        Ala Val Gly Ala Asp Thr Val Leu Ser Phe Gly Ala Asp Ser Val Thr
        465                 470                 475                 480
        Leu Val Gly Val Gly Leu Gly Gly Leu Trp Ser Glu Gly Val Leu Ile
                        485                 490                 495
        Ser Arg Ala Gly Leu Gln Phe Pro Val Gly Arg Leu Leu Arg Arg Leu
                        500                 505                 510
        Leu Arg Arg Leu Leu Arg
                515

<210> SEQ ID NO 29
<211> LENGTH: 494
<212> TYPE: PRT
<213> ORGANISM: Artificial Sequence
<220> FEATURE:
<223> OTHER INFORMATION: B0 - lipase TliA -B0
```

<400> SEQUENCE: 29

```
Arg Ala Gly Leu Gln Phe Pro Val Gly Met Gly Val Phe Asp Tyr Lys
 1               5                  10                  15

Asn Leu Gly Thr Glu Ala Ser Lys Thr Leu Phe Ala Asp Ala Thr Ala
            20                  25                  30

Ile Thr Leu Tyr Thr Tyr His Asn Leu Asp Asn Gly Phe Ala Val Gly
        35                  40                  45

Tyr Gln Gln His Gly Leu Gly Leu Gly Leu Pro Ala Thr Leu Val Gly
    50                  55                  60

Ala Leu Leu Gly Ser Thr Asp Ser Gln Gly Val Ile Pro Gly Ile Pro
 65                 70                  75                  80

Trp Asn Pro Asp Ser Glu Lys Ala Ala Leu Asp Ala Val His Ala Ala
                85                  90                  95

Gly Trp Thr Pro Ile Ser Ala Ser Ala Leu Gly Tyr Gly Gly Lys Val
            100                 105                 110

Asp Ala Arg Gly Thr Phe Phe Gly Glu Lys Ala Gly Tyr Thr Thr Ala
            115                 120                 125

Gln Ala Glu Val Leu Gly Lys Tyr Asp Asp Ala Gly Lys Leu Leu Glu
    130                 135                 140

Ile Gly Ile Gly Phe Arg Gly Thr Ser Gly Pro Arg Glu Ser Leu Ile
145                 150                 155                 160

Thr Asp Ser Ile Gly Asp Leu Val Ser Asp Leu Leu Ala Ala Leu Gly
                165                 170                 175

Pro Lys Asp Tyr Ala Lys Asn Tyr Ala Gly Glu Ala Phe Gly Gly Leu
            180                 185                 190

Leu Lys Thr Val Ala Asp Tyr Ala Gly Ala His Gly Leu Ser Gly Lys
        195                 200                 205

Asp Val Leu Val Ser Gly His Ser Leu Gly Gly Leu Ala Val Asn Ser
    210                 215                 220

Met Ala Asp Leu Ser Thr Ser Lys Trp Ala Gly Phe Tyr Lys Asp Ala
225                 230                 235                 240

Asn Tyr Leu Ala Tyr Ala Ser Pro Thr Gln Ser Ala Gly Asp Lys Val
                245                 250                 255

Leu Asn Ile Gly Tyr Glu Asn Asp Pro Val Phe Arg Ala Leu Asp Gly
            260                 265                 270

Ser Thr Phe Asn Leu Ser Ser Leu Gly Val His Asp Lys Ala His Glu
        275                 280                 285

Ser Thr Thr Asp Asn Ile Val Ser Phe Asn Asp His Tyr Ala Ser Thr
    290                 295                 300

Leu Trp Asn Val Leu Pro Phe Ser Ile Ala Asn Leu Ser Thr Trp Val
305                 310                 315                 320

Ser His Leu Pro Ser Ala Tyr Gly Asp Gly Met Thr Arg Val Leu Glu
                325                 330                 335

Ser Gly Phe Tyr Glu Gln Met Thr Arg Asp Ser Thr Ile Ile Val Ala
            340                 345                 350

Asn Leu Ser Asp Pro Ala Arg Ala Asn Thr Trp Val Gln Asp Leu Asn
        355                 360                 365

Arg Asn Ala Glu Pro His Thr Gly Asn Thr Phe Ile Ile Gly Ser Asp
    370                 375                 380

Gly Asn Asp Leu Ile Gln Gly Gly Lys Gly Ala Asp Phe Ile Glu Gly
385                 390                 395                 400

Gly Lys Gly Asn Asp Thr Ile Arg Asp Asn Ser Gly His Asn Thr Phe
                405                 410                 415
```

```
Leu Phe Ser Gly His Phe Gly Gln Asp Arg Ile Ile Gly Tyr Gln Pro
                420                 425                 430

Thr Asp Arg Leu Val Phe Gln Gly Ala Asp Gly Ser Thr Asp Leu Arg
            435                 440                 445

Asp His Ala Lys Ala Val Gly Ala Asp Thr Val Leu Ser Phe Gly Ala
    450                 455                 460

Asp Ser Val Thr Leu Val Gly Val Gly Leu Gly Gly Leu Trp Ser Glu
465                 470                 475                 480

Gly Val Leu Ile Ser Arg Ala Gly Leu Gln Phe Pro Val Gly
                485                 490

<210> SEQ ID NO 30
<211> LENGTH: 514
<212> TYPE: PRT
<213> ORGANISM: Artificial Sequence
<220> FEATURE:
<223> OTHER INFORMATION: Paracin I - lipase TliA - Paracin I

<400> SEQUENCE: 30

Lys Gly Arg Gly Lys Gln Gly Gly Lys Val Arg Ala Lys Ala Lys Thr
1               5                   10                  15

Arg Ser Ser Met Gly Val Phe Asp Tyr Lys Asn Leu Gly Thr Glu Ala
            20                  25                  30

Ser Lys Thr Leu Phe Ala Asp Ala Thr Ala Ile Thr Leu Tyr Thr Tyr
        35                  40                  45

His Asn Leu Asp Asn Gly Phe Ala Val Gly Tyr Gln Gln His Gly Leu
    50                  55                  60

Gly Leu Gly Leu Pro Ala Thr Leu Val Gly Ala Leu Leu Gly Ser Thr
65                  70                  75                  80

Asp Ser Gln Gly Val Ile Pro Gly Ile Pro Trp Asn Pro Asp Ser Glu
                85                  90                  95

Lys Ala Ala Leu Asp Ala Val His Ala Ala Gly Trp Thr Pro Ile Ser
            100                 105                 110

Ala Ser Ala Leu Gly Tyr Gly Gly Lys Val Asp Ala Arg Gly Thr Phe
        115                 120                 125

Phe Gly Glu Lys Ala Gly Tyr Thr Thr Ala Gln Ala Glu Val Leu Gly
    130                 135                 140

Lys Tyr Asp Asp Ala Gly Lys Leu Leu Glu Ile Gly Ile Gly Phe Arg
145                 150                 155                 160

Gly Thr Ser Gly Pro Arg Glu Ser Leu Ile Thr Asp Ser Ile Gly Asp
                165                 170                 175

Leu Val Ser Asp Leu Leu Ala Ala Leu Gly Pro Lys Asp Tyr Ala Lys
            180                 185                 190

Asn Tyr Ala Gly Glu Ala Phe Gly Gly Leu Leu Lys Thr Val Ala Asp
        195                 200                 205

Tyr Ala Gly Ala His Gly Leu Ser Gly Lys Asp Val Leu Val Ser Gly
    210                 215                 220

His Ser Leu Gly Gly Leu Ala Val Asn Ser Met Ala Asp Leu Ser Thr
225                 230                 235                 240

Ser Lys Trp Ala Gly Phe Tyr Lys Asp Ala Asn Tyr Leu Ala Tyr Ala
                245                 250                 255

Ser Pro Thr Gln Ser Ala Gly Asp Lys Val Leu Asn Ile Gly Tyr Glu
            260                 265                 270

Asn Asp Pro Val Phe Arg Ala Leu Asp Gly Ser Thr Phe Asn Leu Ser
        275                 280                 285
```

Ser Leu Gly Val His Asp Lys Ala His Glu Ser Thr Thr Asp Asn Ile
290 295 300

Val Ser Phe Asn Asp His Tyr Ala Ser Thr Leu Trp Asn Val Leu Pro
305 310 315 320

Phe Ser Ile Ala Asn Leu Ser Thr Trp Val Ser His Leu Pro Ser Ala
325 330 335

Tyr Gly Asp Gly Met Thr Arg Val Leu Glu Ser Gly Phe Tyr Glu Gln
340 345 350

Met Thr Arg Asp Ser Thr Ile Ile Val Ala Asn Leu Ser Asp Pro Ala
355 360 365

Arg Ala Asn Thr Trp Val Gln Asp Leu Asn Arg Asn Ala Glu Pro His
370 375 380

Thr Gly Asn Thr Phe Ile Ile Gly Ser Asp Gly Asn Asp Leu Ile Gln
385 390 395 400

Gly Gly Lys Gly Ala Asp Phe Ile Glu Gly Gly Lys Gly Asn Asp Thr
405 410 415

Ile Arg Asp Asn Ser Gly His Asn Thr Phe Leu Phe Ser Gly His Phe
420 425 430

Gly Gln Asp Arg Ile Ile Gly Tyr Gln Pro Thr Asp Arg Leu Val Phe
435 440 445

Gln Gly Ala Asp Gly Ser Thr Asp Leu Arg Asp His Ala Lys Ala Val
450 455 460

Gly Ala Asp Thr Val Leu Ser Phe Gly Ala Asp Ser Val Thr Leu Val
465 470 475 480

Gly Val Gly Leu Gly Leu Trp Ser Glu Val Gly Leu Ile Ser Lys
485 490 495

Gly Arg Gly Lys Gln Gly Gly Lys Val Arg Ala Lys Lys Thr Arg
500 505 510

Ser Ser

<210> SEQ ID NO 31
<211> LENGTH: 514
<212> TYPE: PRT
<213> ORGANISM: Artificial Sequence
<220> FEATURE:
<223> OTHER INFORMATION: NKC - lipase TliA - NKC

<400> SEQUENCE: 31

Ala Pro Lys Ala Met Lys Leu Leu Lys Leu Leu Lys Leu Gln Lys
1 5 10 15

Lys Gly Ile Met Gly Val Phe Asp Tyr Lys Asn Leu Gly Thr Glu Ala
20 25 30

Ser Lys Thr Leu Phe Ala Asp Ala Thr Ala Ile Thr Leu Tyr Thr Tyr
35 40 45

His Asn Leu Asp Asn Gly Phe Ala Val Gly Tyr Gln Gln His Gly Leu
50 55 60

Gly Leu Gly Leu Pro Ala Thr Leu Val Gly Ala Leu Leu Gly Ser Thr
65 70 75 80

Asp Ser Gln Gly Val Ile Pro Gly Ile Pro Trp Asn Pro Asp Ser Glu
85 90 95

Lys Ala Ala Leu Asp Ala Val His Ala Ala Gly Trp Thr Pro Ile Ser
100 105 110

Ala Ser Ala Leu Gly Tyr Gly Gly Lys Val Asp Ala Arg Gly Thr Phe
115 120 125

Phe Gly Glu Lys Ala Gly Tyr Thr Thr Ala Gln Ala Glu Val Leu Gly
            130                 135                 140

Lys Tyr Asp Asp Ala Gly Lys Leu Leu Glu Ile Gly Ile Gly Phe Arg
145                 150                 155                 160

Gly Thr Ser Gly Pro Arg Glu Ser Leu Ile Thr Asp Ser Ile Gly Asp
                165                 170                 175

Leu Val Ser Asp Leu Leu Ala Ala Leu Gly Pro Lys Asp Tyr Ala Lys
            180                 185                 190

Asn Tyr Ala Gly Glu Ala Phe Gly Gly Leu Leu Lys Thr Val Ala Asp
            195                 200                 205

Tyr Ala Gly Ala His Gly Leu Ser Gly Lys Asp Val Leu Val Ser Gly
    210                 215                 220

His Ser Leu Gly Gly Leu Ala Val Asn Ser Met Ala Asp Leu Ser Thr
225                 230                 235                 240

Ser Lys Trp Ala Gly Phe Tyr Lys Asp Ala Asn Tyr Leu Ala Tyr Ala
                245                 250                 255

Ser Pro Thr Gln Ser Ala Gly Asp Lys Val Leu Asn Ile Gly Tyr Glu
            260                 265                 270

Asn Asp Pro Val Phe Arg Ala Leu Asp Gly Ser Thr Phe Asn Leu Ser
            275                 280                 285

Ser Leu Gly Val His Asp Lys Ala His Glu Ser Thr Thr Asp Asn Ile
    290                 295                 300

Val Ser Phe Asn Asp His Tyr Ala Ser Thr Leu Trp Asn Val Leu Pro
305                 310                 315                 320

Phe Ser Ile Ala Asn Leu Ser Thr Trp Val Ser His Leu Pro Ser Ala
                325                 330                 335

Tyr Gly Asp Gly Met Thr Arg Val Leu Glu Ser Gly Phe Tyr Glu Gln
            340                 345                 350

Met Thr Arg Asp Ser Thr Ile Ile Val Ala Asn Leu Ser Asp Pro Ala
            355                 360                 365

Arg Ala Asn Thr Trp Val Gln Asp Leu Asn Arg Asn Ala Glu Pro His
    370                 375                 380

Thr Gly Asn Thr Phe Ile Ile Gly Ser Asp Gly Asn Asp Leu Ile Gln
385                 390                 395                 400

Gly Gly Lys Gly Ala Asp Phe Ile Glu Gly Gly Lys Gly Asn Asp Thr
                405                 410                 415

Ile Arg Asp Asn Ser Gly His Asn Thr Phe Leu Phe Ser Gly His Phe
            420                 425                 430

Gly Gln Asp Arg Ile Ile Gly Tyr Gln Pro Thr Asp Arg Leu Val Phe
            435                 440                 445

Gln Gly Ala Asp Gly Ser Thr Asp Leu Arg Asp His Ala Lys Ala Val
    450                 455                 460

Gly Ala Asp Thr Val Leu Ser Phe Gly Ala Asp Ser Val Thr Leu Val
465                 470                 475                 480

Gly Val Gly Leu Gly Gly Leu Trp Ser Glu Gly Val Leu Ile Ser Ala
                485                 490                 495

Pro Lys Ala Met Lys Leu Leu Lys Lys Leu Leu Lys Leu Gln Lys Lys
            500                 505                 510

Gly Ile

<210> SEQ ID NO 32
<211> LENGTH: 514
<212> TYPE: PRT
<213> ORGANISM: Artificial Sequence
<220> FEATURE:
<223> OTHER INFORMATION: NRC - lipase TliA - NRC

<400> SEQUENCE: 32

```
Ala Pro Lys Ala Met Arg Leu Leu Arg Arg Leu Leu Arg Leu Gln Lys
  1               5                  10                  15

Lys Gly Ile Met Gly Val Phe Asp Tyr Lys Asn Leu Gly Thr Glu Ala
             20                  25                  30

Ser Lys Thr Leu Phe Ala Asp Ala Thr Ala Ile Thr Leu Tyr Thr Tyr
         35                  40                  45

His Asn Leu Asp Asn Gly Phe Ala Val Gly Tyr Gln Gln His Gly Leu
     50                  55                  60

Gly Leu Gly Leu Pro Ala Thr Leu Val Gly Ala Leu Leu Gly Ser Thr
 65                  70                  75                  80

Asp Ser Gln Gly Val Ile Pro Gly Ile Pro Trp Asn Pro Asp Ser Glu
                 85                  90                  95

Lys Ala Ala Leu Asp Ala Val His Ala Ala Gly Trp Thr Pro Ile Ser
            100                 105                 110

Ala Ser Ala Leu Gly Tyr Gly Gly Lys Val Asp Ala Arg Gly Thr Phe
        115                 120                 125

Phe Gly Glu Lys Ala Gly Tyr Thr Thr Ala Gln Ala Glu Val Leu Gly
    130                 135                 140

Lys Tyr Asp Asp Ala Gly Lys Leu Leu Glu Ile Gly Ile Gly Phe Arg
145                 150                 155                 160

Gly Thr Ser Gly Pro Arg Glu Ser Leu Ile Thr Asp Ser Ile Gly Asp
                165                 170                 175

Leu Val Ser Asp Leu Leu Ala Ala Leu Gly Pro Lys Asp Tyr Ala Lys
            180                 185                 190

Asn Tyr Ala Gly Glu Ala Phe Gly Gly Leu Leu Lys Thr Val Ala Asp
        195                 200                 205

Tyr Ala Gly Ala His Gly Leu Ser Gly Lys Asp Val Leu Val Ser Gly
    210                 215                 220

His Ser Leu Gly Gly Leu Ala Val Asn Ser Met Ala Asp Leu Ser Thr
225                 230                 235                 240

Ser Lys Trp Ala Gly Phe Tyr Lys Asp Ala Asn Tyr Leu Ala Tyr Ala
                245                 250                 255

Ser Pro Thr Gln Ser Ala Gly Asp Lys Val Leu Asn Ile Gly Tyr Glu
            260                 265                 270

Asn Asp Pro Val Phe Arg Ala Leu Asp Gly Ser Thr Phe Asn Leu Ser
        275                 280                 285

Ser Leu Gly Val His Asp Lys Ala His Glu Ser Thr Thr Asp Asn Ile
    290                 295                 300

Val Ser Phe Asn Asp His Tyr Ala Ser Thr Leu Trp Asn Val Leu Pro
305                 310                 315                 320

Phe Ser Ile Ala Asn Leu Ser Thr Trp Val Ser His Leu Pro Ser Ala
                325                 330                 335

Tyr Gly Asp Gly Met Thr Arg Val Leu Glu Ser Gly Phe Tyr Glu Gln
            340                 345                 350

Met Thr Arg Asp Ser Thr Ile Ile Val Ala Asn Leu Ser Asp Pro Ala
        355                 360                 365

Arg Ala Asn Thr Trp Val Gln Asp Leu Asn Arg Asn Ala Glu Pro His
    370                 375                 380

Thr Gly Asn Thr Phe Ile Ile Gly Ser Asp Gly Asn Asp Leu Ile Gln
385                 390                 395                 400
```

```
Gly Gly Lys Gly Ala Asp Phe Ile Glu Gly Lys Gly Asn Asp Thr
            405                 410                 415

Ile Arg Asp Asn Ser Gly His Asn Thr Phe Leu Phe Ser Gly His Phe
        420                 425                 430

Gly Gln Asp Arg Ile Ile Gly Tyr Gln Pro Thr Asp Arg Leu Val Phe
    435                 440                 445

Gln Gly Ala Asp Gly Ser Thr Asp Leu Arg Asp His Ala Lys Ala Val
450                 455                 460

Gly Ala Asp Thr Val Leu Ser Phe Gly Ala Asp Ser Val Thr Leu Val
465                 470                 475                 480

Gly Val Gly Leu Gly Leu Trp Ser Glu Gly Val Leu Ile Ser Ala
            485                 490                 495

Pro Lys Ala Met Arg Leu Leu Arg Arg Leu Leu Arg Leu Gln Lys Lys
            500                 505                 510

Gly Ile

<210> SEQ ID NO 33
<211> LENGTH: 382
<212> TYPE: PRT
<213> ORGANISM: Artificial Sequence
<220> FEATURE:
<223> OTHER INFORMATION: Buforin IIb - lipase M37 - Buforin IIb

<400> SEQUENCE: 33

Arg Ala Gly Leu Gln Phe Pro Val Gly Arg Leu Leu Arg Arg Leu Leu
 1               5                  10                  15

Arg Arg Leu Leu Arg Met Ser Tyr Thr Lys Glu Gln Leu Met Leu Ala
            20                  25                  30

Phe Ser Tyr Met Ser Tyr Tyr Gly Ile Thr His Thr Gly Ser Ala Lys
        35                  40                  45

Lys Asn Ala Glu Leu Ile Leu Lys Lys Met Lys Glu Ala Leu Lys Thr
 50                  55                  60

Trp Lys Pro Phe Gln Glu Asp Asp Trp Glu Val Val Trp Gly Pro Ala
 65                  70                  75                  80

Val Tyr Thr Met Pro Phe Thr Ile Phe Asn Asp Ala Met Met Tyr Val
             85                  90                  95

Ile Gln Lys Lys Gly Ala Glu Gly Glu Tyr Val Ile Ala Ile Arg Gly
            100                 105                 110

Thr Asn Pro Val Ser Ile Ser Asp Trp Leu Phe Asn Asp Phe Met Val
        115                 120                 125

Ser Ala Met Lys Lys Trp Pro Tyr Ala Ser Val Glu Gly Arg Ile Leu
130                 135                 140

Lys Ile Ser Glu Ser Thr Ser Tyr Gly Leu Lys Thr Leu Gln Lys Leu
145                 150                 155                 160

Lys Pro Lys Ser His Ile Pro Gly Glu Asn Lys Thr Ile Leu Gln Phe
                165                 170                 175

Leu Asn Glu Lys Ile Gly Pro Glu Gly Lys Ala Lys Ile Cys Val Thr
            180                 185                 190

Gly His Ser Lys Gly Gly Ala Leu Ser Ser Thr Leu Ala Leu Trp Leu
        195                 200                 205

Lys Asp Ile Gln Gly Val Lys Leu Ser Gln Asn Ile Asp Ile Ser Thr
210                 215                 220

Ile Pro Phe Ala Gly Pro Thr Ala Gly Asn Ala Asp Phe Ala Asp Tyr
225                 230                 235                 240
```

```
Phe Asp Asp Cys Leu Gly Asp Gln Cys Thr Arg Ile Ala Asn Ser Leu
                245                 250                 255

Asp Ile Val Pro Tyr Ala Trp Asn Thr Asn Ser Leu Lys Lys Leu Lys
            260                 265                 270

Ser Ile Tyr Ile Ser Glu Gln Ala Ser Val Lys Pro Leu Leu Tyr Gln
        275                 280                 285

Arg Ala Leu Ile Arg Ala Met Ile Ala Glu Thr Lys Gly Lys Lys Tyr
        290                 295                 300

Lys Gln Ile Lys Ala Glu Thr Pro Pro Leu Glu Gly Asn Ile Asn Pro
305                 310                 315                 320

Ile Leu Ile Glu Tyr Leu Val Gln Ala Ala Tyr Gln His Val Val Gly
                325                 330                 335

Tyr Pro Glu Leu Met Gly Met Met Asp Asp Ile Pro Leu Thr Asp Ile
            340                 345                 350

Phe Glu Asp Ala Ile Ala Gly Leu Leu Arg Ala Gly Leu Gln Phe Pro
        355                 360                 365

Val Gly Arg Leu Leu Arg Arg Leu Leu Arg Arg Leu Leu Arg
        370                 375                 380

<210> SEQ ID NO 34
<211> LENGTH: 358
<212> TYPE: PRT
<213> ORGANISM: Artificial Sequence
<220> FEATURE:
<223> OTHER INFORMATION: B0 - lipase M37 - B0

<400> SEQUENCE: 34

Arg Ala Gly Leu Gln Phe Pro Val Gly Met Ser Tyr Thr Lys Glu Gln
1               5                   10                  15

Leu Met Leu Ala Phe Ser Tyr Met Ser Tyr Tyr Gly Ile Thr His Thr
            20                  25                  30

Gly Ser Ala Lys Lys Asn Ala Glu Leu Ile Leu Lys Lys Met Lys Glu
        35                  40                  45

Ala Leu Lys Thr Trp Lys Pro Phe Gln Glu Asp Asp Trp Glu Val Val
    50                  55                  60

Trp Gly Pro Ala Val Tyr Thr Met Pro Phe Thr Ile Phe Asn Asp Ala
65                  70                  75                  80

Met Met Tyr Val Ile Gln Lys Lys Gly Ala Glu Gly Glu Tyr Val Ile
                85                  90                  95

Ala Ile Arg Gly Thr Asn Pro Val Ser Ile Ser Asp Trp Leu Phe Asn
            100                 105                 110

Asp Phe Met Val Ser Ala Met Lys Lys Trp Pro Tyr Ala Ser Val Glu
        115                 120                 125

Gly Arg Ile Leu Lys Ile Ser Glu Ser Thr Ser Tyr Gly Leu Lys Thr
    130                 135                 140

Leu Gln Lys Leu Lys Pro Lys Ser His Ile Pro Gly Glu Asn Lys Thr
145                 150                 155                 160

Ile Leu Gln Phe Leu Asn Glu Lys Ile Gly Pro Glu Gly Lys Ala Lys
                165                 170                 175

Ile Cys Val Thr Gly His Ser Lys Gly Gly Ala Leu Ser Ser Thr Leu
            180                 185                 190

Ala Leu Trp Leu Lys Asp Ile Gln Gly Val Lys Leu Ser Gln Asn Ile
        195                 200                 205

Asp Ile Ser Thr Ile Pro Phe Ala Gly Pro Thr Ala Gly Asn Ala Asp
    210                 215                 220
```

Phe Ala Asp Tyr Phe Asp Asp Cys Leu Gly Asp Gln Cys Thr Arg Ile
225                 230                 235                 240

Ala Asn Ser Leu Asp Ile Val Pro Tyr Ala Trp Asn Thr Asn Ser Leu
            245                 250                 255

Lys Lys Leu Lys Ser Ile Tyr Ile Ser Glu Gln Ala Ser Val Lys Pro
        260                 265                 270

Leu Leu Tyr Gln Arg Ala Leu Ile Arg Ala Met Ile Ala Glu Thr Lys
    275                 280                 285

Gly Lys Lys Tyr Lys Gln Ile Lys Ala Glu Thr Pro Pro Leu Glu Gly
290                 295                 300

Asn Ile Asn Pro Ile Leu Ile Glu Tyr Leu Val Gln Ala Ala Tyr Gln
305                 310                 315                 320

His Val Val Gly Tyr Pro Glu Leu Met Gly Met Met Asp Asp Ile Pro
                325                 330                 335

Leu Thr Asp Ile Phe Glu Asp Ala Ile Ala Gly Leu Leu Arg Ala Gly
            340                 345                 350

Leu Gln Phe Pro Val Gly
        355

<210> SEQ ID NO 35
<211> LENGTH: 378
<212> TYPE: PRT
<213> ORGANISM: Artificial Sequence
<220> FEATURE:
<223> OTHER INFORMATION: Paracin I - lipase M37 - Paracin I

<400> SEQUENCE: 35

Lys Gly Arg Gly Lys Gln Gly Gly Lys Val Arg Ala Lys Ala Lys Thr
1               5                   10                  15

Arg Ser Ser Met Ser Tyr Thr Lys Glu Gln Leu Met Leu Ala Phe Ser
            20                  25                  30

Tyr Met Ser Tyr Tyr Gly Ile Thr His Thr Gly Ser Ala Lys Lys Asn
        35                  40                  45

Ala Glu Leu Ile Leu Lys Lys Met Lys Glu Ala Leu Lys Thr Trp Lys
    50                  55                  60

Pro Phe Gln Glu Asp Asp Trp Glu Val Val Trp Gly Pro Ala Val Tyr
65                  70                  75                  80

Thr Met Pro Phe Thr Ile Phe Asn Asp Ala Met Met Tyr Val Ile Gln
                85                  90                  95

Lys Lys Gly Ala Glu Gly Glu Tyr Val Ile Ala Ile Arg Gly Thr Asn
            100                 105                 110

Pro Val Ser Ile Ser Asp Trp Leu Phe Asn Asp Phe Met Val Ser Ala
        115                 120                 125

Met Lys Lys Trp Pro Tyr Ala Ser Val Glu Gly Arg Ile Leu Lys Ile
130                 135                 140

Ser Glu Ser Thr Ser Tyr Gly Leu Lys Thr Leu Gln Lys Leu Lys Pro
145                 150                 155                 160

Lys Ser His Ile Pro Gly Glu Asn Lys Thr Ile Leu Gln Phe Leu Asn
                165                 170                 175

Glu Lys Ile Gly Pro Glu Gly Lys Ala Lys Ile Cys Val Thr Gly His
            180                 185                 190

Ser Lys Gly Gly Ala Leu Ser Ser Thr Leu Ala Leu Trp Leu Lys Asp
        195                 200                 205

Ile Gln Gly Val Lys Leu Ser Gln Asn Ile Asp Ile Ser Thr Ile Pro
210                 215                 220

```
Phe Ala Gly Pro Thr Ala Gly Asn Ala Asp Phe Ala Asp Tyr Phe Asp
225                 230                 235                 240

Asp Cys Leu Gly Asp Gln Cys Thr Arg Ile Ala Asn Ser Leu Asp Ile
            245                 250                 255

Val Pro Tyr Ala Trp Asn Thr Asn Ser Leu Lys Lys Leu Lys Ser Ile
            260                 265                 270

Tyr Ile Ser Glu Gln Ala Ser Val Lys Pro Leu Leu Tyr Gln Arg Ala
            275                 280                 285

Leu Ile Arg Ala Met Ile Ala Glu Thr Lys Gly Lys Lys Tyr Lys Gln
            290                 295                 300

Ile Lys Ala Glu Thr Pro Pro Leu Glu Gly Asn Ile Asn Pro Ile Leu
305                 310                 315                 320

Ile Glu Tyr Leu Val Gln Ala Ala Tyr Gln His Val Val Gly Tyr Pro
                325                 330                 335

Glu Leu Met Gly Met Met Asp Asp Ile Pro Leu Thr Asp Ile Phe Glu
                340                 345                 350

Asp Ala Ile Ala Gly Leu Leu Lys Gly Arg Gly Lys Gln Gly Gly Lys
                355                 360                 365

Val Arg Ala Lys Ala Lys Thr Arg Ser Ser
            370                 375

<210> SEQ ID NO 36
<211> LENGTH: 378
<212> TYPE: PRT
<213> ORGANISM: Artificial Sequence
<220> FEATURE:
<223> OTHER INFORMATION: NKC - lipase M37 - NKC

<400> SEQUENCE: 36

Ala Pro Lys Ala Met Lys Leu Leu Lys Lys Leu Leu Lys Leu Gln Lys
1               5                   10                  15

Lys Gly Ile Met Ser Tyr Thr Lys Glu Gln Leu Met Leu Ala Phe Ser
            20                  25                  30

Tyr Met Ser Tyr Tyr Gly Ile Thr His Thr Gly Ser Ala Lys Lys Asn
            35                  40                  45

Ala Glu Leu Ile Leu Lys Lys Met Lys Glu Ala Leu Lys Thr Trp Lys
        50                  55                  60

Pro Phe Gln Glu Asp Asp Trp Glu Val Val Trp Gly Pro Ala Val Tyr
65                  70                  75                  80

Thr Met Pro Phe Thr Ile Phe Asn Asp Ala Met Met Tyr Val Ile Gln
                85                  90                  95

Lys Lys Gly Ala Glu Gly Glu Tyr Val Ile Ala Ile Arg Gly Thr Asn
            100                 105                 110

Pro Val Ser Ile Ser Asp Trp Leu Phe Asn Asp Phe Met Val Ser Ala
            115                 120                 125

Met Lys Lys Trp Pro Tyr Ala Ser Val Glu Gly Arg Ile Leu Lys Ile
130                 135                 140

Ser Glu Ser Thr Ser Tyr Gly Leu Lys Thr Leu Gln Lys Leu Lys Pro
145                 150                 155                 160

Lys Ser His Ile Pro Gly Glu Asn Lys Thr Ile Leu Gln Phe Leu Asn
            165                 170                 175

Glu Lys Ile Gly Pro Glu Gly Lys Ala Lys Ile Cys Val Thr Gly His
            180                 185                 190

Ser Lys Gly Gly Ala Leu Ser Ser Thr Leu Ala Leu Trp Leu Lys Asp
            195                 200                 205
```

```
Ile Gln Gly Val Lys Leu Ser Gln Asn Ile Asp Ile Ser Thr Ile Pro
    210                 215                 220

Phe Ala Gly Pro Thr Ala Gly Asn Ala Asp Phe Ala Asp Tyr Phe Asp
225                 230                 235                 240

Asp Cys Leu Gly Asp Gln Cys Thr Arg Ile Ala Asn Ser Leu Asp Ile
                245                 250                 255

Val Pro Tyr Ala Trp Asn Thr Asn Ser Leu Lys Lys Leu Lys Ser Ile
            260                 265                 270

Tyr Ile Ser Glu Gln Ala Ser Val Lys Pro Leu Leu Tyr Gln Arg Ala
        275                 280                 285

Leu Ile Arg Ala Met Ile Ala Glu Thr Lys Gly Lys Lys Tyr Lys Gln
    290                 295                 300

Ile Lys Ala Glu Thr Pro Pro Leu Glu Gly Asn Ile Asn Pro Ile Leu
305                 310                 315                 320

Ile Glu Tyr Leu Val Gln Ala Ala Tyr Gln His Val Val Gly Tyr Pro
                325                 330                 335

Glu Leu Met Gly Met Met Asp Asp Ile Pro Leu Thr Asp Ile Phe Glu
                340                 345                 350

Asp Ala Ile Ala Gly Leu Leu Ala Pro Lys Ala Met Lys Leu Leu Lys
                355                 360                 365

Lys Leu Leu Lys Leu Gln Lys Lys Gly Ile
    370                 375
```

<210> SEQ ID NO 37
<211> LENGTH: 378
<212> TYPE: PRT
<213> ORGANISM: Artificial Sequence
<220> FEATURE:
<223> OTHER INFORMATION: NRC - lipase M37 - NRC

<400> SEQUENCE: 37

```
Ala Pro Lys Ala Met Arg Leu Leu Arg Arg Leu Leu Arg Leu Gln Lys
  1               5                  10                  15

Lys Gly Ile Met Ser Tyr Thr Lys Glu Gln Leu Met Leu Ala Phe Ser
                20                  25                  30

Tyr Met Ser Tyr Tyr Gly Ile Thr His Thr Gly Ser Ala Lys Lys Asn
            35                  40                  45

Ala Glu Leu Ile Leu Lys Lys Met Lys Glu Ala Leu Lys Thr Trp Lys
    50                  55                  60

Pro Phe Gln Glu Asp Asp Trp Glu Val Val Trp Gly Pro Ala Val Tyr
65                  70                  75                  80

Thr Met Pro Phe Thr Ile Phe Asn Asp Ala Met Met Tyr Val Ile Gln
                85                  90                  95

Lys Lys Gly Ala Glu Gly Glu Tyr Val Ile Ala Ile Arg Gly Thr Asn
            100                 105                 110

Pro Val Ser Ile Ser Asp Trp Leu Phe Asn Asp Phe Met Val Ser Ala
    115                 120                 125

Met Lys Lys Trp Pro Tyr Ala Ser Val Glu Gly Arg Ile Leu Lys Ile
130                 135                 140

Ser Glu Ser Thr Ser Tyr Gly Leu Lys Thr Leu Gln Lys Leu Lys Pro
145                 150                 155                 160

Lys Ser His Ile Pro Gly Glu Asn Lys Thr Ile Leu Gln Phe Leu Asn
                165                 170                 175

Glu Lys Ile Gly Pro Glu Gly Lys Ala Lys Ile Cys Val Thr Gly His
            180                 185                 190
```

```
Ser Lys Gly Gly Ala Leu Ser Ser Thr Leu Ala Leu Trp Leu Lys Asp
            195                 200                 205

Ile Gln Gly Val Lys Leu Ser Gln Asn Ile Asp Ile Ser Thr Ile Pro
210                 215                 220

Phe Ala Gly Pro Thr Ala Gly Asn Ala Asp Phe Ala Asp Tyr Phe Asp
225                 230                 235                 240

Asp Cys Leu Gly Asp Gln Cys Thr Arg Ile Ala Asn Ser Leu Asp Ile
            245                 250                 255

Val Pro Tyr Ala Trp Asn Thr Asn Ser Leu Lys Lys Leu Lys Ser Ile
            260                 265                 270

Tyr Ile Ser Glu Gln Ala Ser Val Lys Pro Leu Leu Tyr Gln Arg Ala
            275                 280                 285

Leu Ile Arg Ala Met Ile Ala Glu Thr Lys Gly Lys Lys Tyr Lys Gln
            290                 295                 300

Ile Lys Ala Glu Thr Pro Pro Leu Glu Gly Asn Ile Asn Pro Ile Leu
305                 310                 315                 320

Ile Glu Tyr Leu Val Gln Ala Ala Tyr Gln His Val Val Gly Tyr Pro
            325                 330                 335

Glu Leu Met Gly Met Met Asp Asp Ile Pro Leu Thr Asp Ile Phe Glu
            340                 345                 350

Asp Ala Ile Ala Gly Leu Leu Ala Pro Lys Ala Met Arg Leu Leu Arg
            355                 360                 365

Arg Leu Leu Arg Leu Gln Lys Lys Gly Ile
            370                 375
```

```
<210> SEQ ID NO 38
<211> LENGTH: 63
<212> TYPE: DNA
<213> ORGANISM: Artificial Sequence
<220> FEATURE:
<223> OTHER INFORMATION: Buforin IIb

<400> SEQUENCE: 38
cgtgctggtc tgcagttccc ggttggtcgt ctgctgcgtc gtctgctgcg tcgtctgctg      60
cgt                                                                   63

<210> SEQ ID NO 39
<211> LENGTH: 27
<212> TYPE: DNA
<213> ORGANISM: Artificial Sequence
<220> FEATURE:
<223> OTHER INFORMATION: B0

<400> SEQUENCE: 39
cgtgctggtc tgcagttccc ggttggt                                         27

<210> SEQ ID NO 40
<211> LENGTH: 57
<212> TYPE: DNA
<213> ORGANISM: Artificial Sequence
<220> FEATURE:
<223> OTHER INFORMATION: Paracin I

<400> SEQUENCE: 40
aaaggaagag gcaaacaggg aggcaaggtg cgtgcgaagg caaagacacg ttcatcc        57

<210> SEQ ID NO 41
<211> LENGTH: 57
<212> TYPE: DNA
<213> ORGANISM: Artificial Sequence
```

```
<220> FEATURE:
<223> OTHER INFORMATION: NKC

<400> SEQUENCE: 41
gcgccgaaag cgatgaaact gttgaagaaa ttgctgaaat tacagaaaaa aggcatt        57

<210> SEQ ID NO 42
<211> LENGTH: 57
<212> TYPE: DNA
<213> ORGANISM: Artificial Sequence
<220> FEATURE:
<223> OTHER INFORMATION: NRC

<400> SEQUENCE: 42
gcgccgaaag cgatgcgtct gttgcgtcgc ttgctgcgtt tacagaaaaa aggcatt        57

<210> SEQ ID NO 43
<211> LENGTH: 1432
<212> TYPE: DNA
<213> ORGANISM: Artificial Sequence
<220> FEATURE:
<223> OTHER INFORMATION: lipase TliA

<400> SEQUENCE: 43
atgggtgtat ttgactacaa gaacctcggc accgaagcca gcaaaacctt gttcgccgat      60
gccaccgcaa tcacgttgta tacctatcac aacctggata acggcttcgc agtcggctac     120
cagcaacatg gcttggggct cggcctgccg gccacactgg tcgggcgtt gctcggcagc     180 acagactccc agggagtgat ccccggcatt ccctggaatc ctgactcgga aaaggccgcc     240
ctggacgcgg tgcacgcagc cggttggacg ccaatcagcg ccagcgcact gggctacggc     300
ggcaaggtgg atgcgcgggg cactttttt ggcgagaagg ccggctacac cacgcccag     360 gccgaagtgc tgggcaagta cgatgacgcc ggcaaactgc tcgagatcgg catcggtttt     420
cgtggcacct cgggccctcg ggaaagcctg attaccgact ccatcggcga tctggtcagc     480
gacctgctcg ccgcgctggg ccccaaggac tatgcgaaaa actatgccgg cgaagcgttt     540
ggcggcttgc tcaagacggt ggccgactat gccggcgccc atggcctgag tggcaaggat     600
gtgctggtca gcggccacag cctgggcggc ctggcggtca cagcatggc cgacctgagc     660 accagcaaat gggcgggttt ctacaaggac gccaactacc tggcctacgc ctcgcccacc     720
cagagcgccg gcgataaggt cctgaatatc ggctacgaaa acgacccggt attccgtgcg     780
ctggacggct ccaccttcaa cctgtcgtcc ctcggcgtgc atgacaaggc ccacgagtcg     840
accaccgaca acatcgtcag cttcaacgac cactacgcct cgacgttgtg gaatgtgctg     900
ccgttttcca tcgccaacct gtcgacctgg gtgtcgcatt gccagcgct acggcgacg     960 gcatgacgcg tgtgctggaa tcggggttct acgagcaaat gacccgtgac tcgacgatta    1020
tcgtcgccaa cctgtccgac ccggcgcgcg ccaacacctg gtccaggac ctcaaccgca    1080 atgccgagcc gcacacaggc aataccttca tcatcggcag cgacggcaat gacctgatcc    1140
agggcggcaa gggcgcggac ttcatcgaag gcggcaaggg caatgacacg atccgcgaca    1200
acagcgggca caacaccttt ttgttcagcg ggcattttgg ccaggatcgg attatcggct    1260
accagccgac cgacaggctg gtgttccagg gcgccgacgg cagcaccgac ctgcgcgacc    1320
acgcgaaggc cgtgggggcc gatacggtgc tgagttttgg cgccgactcg gtgaccctgg    1380
tcggggtcgg gctggcggc ctgtggagcg agggtgtgct gatcagttga gg            1432

<210> SEQ ID NO 44
```

```
<211> LENGTH: 1022
<212> TYPE: DNA
<213> ORGANISM: Artificial Sequence
<220> FEATURE:
<223> OTHER INFORMATION: lipase M37

<400> SEQUENCE: 44
atgtcttata caaaagaaca actcatgttg cattcagct atatgagcta ctatggcatc      60
actcacacag gttcagcaaa aaaaaatgct gagctcatcc ttaaaaaaat gaaagaagcc    120
ttgaaaacat ggaagccttt tcaggaagat gactgggaag tcgtctgggg tcctgcggtt    180
tataccatgc cttcacaat cttcaacgat gccatgatgt atgtcataca aagaaaggt     240
gctgaagggg aatacgtgat agccattcgc ggcaccaatc cagtatcaat ttcagactgg    300
ctgtttaatg atttcatggt cagcgcaatg aagaagtggc cttacgcatc cgttgaaggc    360
cgcatactca aaatatccga agtaccagc tacggactga aaaccttaca gaaattgaag     420
ccaaaatccc atatccccgg cgaaaataaa acgattctgc agttcctgaa tgaaaagata    480
ggcccagagg gtaaagcaaa aatctgtgta acaggccaca gtaaaggcgg cgccttgtct    540
tccactctgg cactgtggtt gaaggacatc caaggagtaa aactctcgca aaacatcgat    600
atctcaacga ttccgtttgc cggaccaaca gccggtaatg ctgactttgc cgattacttt    660
gatgattgtc ttggtgatca atgcacccgc attgccaact cgttagatat tgtgccttat    720
gcctggaata aaattcatta aaaaaactta aatctatata tatttctgaa caagcatcag    780
ttaaaccgct tctatatcaa cgcgctttaa tccgtgcaat gatcgcagaa actaaaggta    840
aaaaatacaa gcaaattaag gcggaaacac caccattaga aggcaacatt aatcctattc    900
ttattgaata ccttgtgcag gcagcatatc agcatgtcgt cggttaccca gaattaatgg    960
gtatgatgga tgatattcct ttaacagaca tattcgaaga tgcgatcgcg ggtttgttat    1020
aa                                                                   1022

<210> SEQ ID NO 45
<211> LENGTH: 1495
<212> TYPE: DNA
<213> ORGANISM: Artificial Sequence
<220> FEATURE:
<223> OTHER INFORMATION: Buforin IIb - lipase TliA

<400> SEQUENCE: 45
cgtgctggtc tgcagttccc ggttggtcgt ctgctgcgtc gtctgctgcg tcgtctgctg      60
cgtatgggtg tatttgacta caagaacctc ggcaccgaag ccagcaaaac cttgttcgcc    120
gatgccaccg caatcacgtt gtataccttat cacaacctgg ataacggctt cgcagtcggc    180
taccagcaac atggcttggg gctcggcctg ccggccacac tggtcggggc gttgctcggc    240
agcacagact cccagggagt gatccccggc attccctgga atcctgactc ggaaaaggcc    300
gccctggacg cggtgcacgc agccggttgg acgccaatca gcgccagcgc actgggctac    360
ggcggcaagg tggatgcgcg gggcactttt tttggcgaga aggccggcta caccacggcc    420
caggccgaag tgctgggcaa gtacgatgac gccggcaaac tgctcgagat cggcatcggt    480
tttcgtggca cctcgggccc tcgggaaagc ctgattaccg actccatcgg cgatctggtc    540
agcgacctgc tcgccgcgct gggccccaag gactatgcga aaaactatgc cggcgaagcg    600
tttggcggct tgctcaagac ggtggccgac tatgccggcg cccatggcct gagtggcaag    660
gatgtgctgt tcagcggcca cagcctgggc ggcctggcgg tcaacagcat ggccgacctg    720
agcaccagca aatgggcggg tttctacaag gacgccaact acctggccta cgcctcgccc    780
```

```
acccagagcg ccggcgataa ggtcctgaat atcggctacg aaaacgaccc ggtattccgt    840
gcgctggacg gctccacctt caacctgtcg tccctcggcg tgcatgacaa ggcccacgag    900
tcgaccaccg acaacatcgt cagcttcaac gaccactacg cctcgacgtt gtggaatgtg    960
ctgccgtttt ccatcgccaa cctgtcgacc tgggtgtcgc atttgccagc gcttacggcg   1020
acggcatgac gcgtgtgctg gaatcggggt tctacgagca aatgacccgt gactcgacga   1080
ttatcgtcgc caacctgtcc gaccggcgcg cgccaacac ctgggtccag gacctcaacc    1140
gcaatgccga ccgcacaca ggcaataccct tcatcatcgg cagcgacggc aatgacctga    1200
tccagggcgg caagggcgcg gacttcatcg aaggcggcaa gggcaatgac acgatccgcg   1260
acaacagcgg gcacaacacc tttttgttca gcgggcattt tggccaggat cggattatcg   1320
gctaccagcc gaccgacagg ctggtgttcc agggcgccga cggcagcacc gacctgcgcg   1380
accacgcgaa ggccgtgggg gccgatacgg tgctgagttt tggcgccgac tcggtgaccc   1440
tggtcggggt cgggctgggc ggcctgtgga gcgagggtgt gctgatcagt tgagg         1495

<210> SEQ ID NO 46
<211> LENGTH: 1459
<212> TYPE: DNA
<213> ORGANISM: Artificial Sequence
<220> FEATURE:
<223> OTHER INFORMATION: B0 - lipase TliA

<400> SEQUENCE: 46
cgtgctggtc tgcagttccc ggttggtatg ggtgtatttg actacaagaa cctcggcacc     60
gaagccagca aaaccttgtt cgccgatgcc accgcaatca cgttgtatac ctatcacaac    120
ctggataacg gcttcgcagt cggctaccag caacatggct tggggctcgg cctgccggcc    180
acactggtcg gggcgttgct cggcagcaca gactcccagg gagtgatccc cggcattccc    240
tggaatcctg actcggaaaa ggccgccctg gacgcgtgc acgcagccgg ttggacgcca    300
atcagcgcca gcgcactggg ctacgcggc aaggtggatg cgcggggcac tttttttggc    360
gagaaggccg gctacaccac ggcccaggcc gaagtgctgg gcaagtacga tgacgccggc    420
aaactgctcg agatcggcat cggttttcgt ggcacctcgg gccctcggga aagcctgatt    480
accgactcca tcggcgatct ggtcagcgac ctgctcgccg cgctgggccc caaggactat    540
gcgaaaaact atgccggcga agcgtttggc ggcttgctca agacggtggc cgactatgcc    600
ggcgcccatg gcctgagtgg caaggatgtg ctggtcagcg ccacagcct gggcggcctg    660 gcggtcaaca gcatggccga cctgagcacc agcaaatggg cgggtttcta caaggacgcc    720
aactacctgg cctacgcctc gcccacccag agcgccggcg ataaggtcct gaatatcggc    780
tacgaaaacg cccggtatt ccgtgcgctg gacggctcca ccttcaacct gtcgtccctc    840
ggcgtgcatg acaaggccca cgagtcgacc accgacaaca tcgtcagctt caacgaccac    900
tacgcctcga cgttgtggaa tgtgctgccg ttttccatcg ccaacctgtc gacctgggtg    960
tcgcatttgc cagcgcttac ggcgacggca tgacgcgtgt gctggaatcg gggttctacg   1020
agcaaatgac ccgtgactcg acgattatcg tcgccaacct gtccgacccg gcgcgccca    1080 acacctgggt ccaggacctc aaccgcaatg ccgaccgca cacaggcaat accttcatca    1140
tcggcagcga cggcaatgac ctgatccagg gcggcaaggg cgcggacttc atcgaaggcg   1200
gcaagggcaa tgacacgatc cgcgacaaca gcgggcacaa cacctttttg ttcagcgggc   1260
attttggcca ggatcggatt atcggctacc agccgaccga caggctggtg ttccagggcg   1320
```

```
ccgacggcag caccgacctg cgcgaccacg cgaaggccgt gggggccgat acggtgctga    1380
gttttggcgc cgactcggtg accctggtcg gggtcgggct gggcggcctg tggagcgagg    1440
gtgtgctgat cagttgagg                                                 1459

<210> SEQ ID NO 47
<211> LENGTH: 1489
<212> TYPE: DNA
<213> ORGANISM: Artificial Sequence
<220> FEATURE:
<223> OTHER INFORMATION: Paracin I - lipase TliA

<400> SEQUENCE: 47
aaaggaagag gcaaacaggg aggcaaggtg cgtgcgaagg caaagacacg ttcatccatg      60
ggtgtatttg actacaagaa cctcggcacc gaagccagca aaaccttgtt cgccgatgcc    120
accgcaatca cgttgtatac ctatcacaac ctggataacg gcttcgcagt cggctaccag    180
caacatggct tggggctcgg cctgccggcc acactggtcg gggcgttgct cggcagcaca    240
gactcccagg gagtgatccc cggcattccc tggaatcctg actcggaaaa ggccgccctg    300
gacgcggtgc acgcagccgg ttggacgcca atcagcgcca gcgcactggg ctacggcggc    360
aaggtggatg cgcggggcac ttttttttggc gagaaggccg gctacaccac ggcccaggcc    420
gaagtgctgg gcaagtacga tgacgccggc aaactgctcg agatcggcat cggttttcgt    480
ggcacctcgg gccctcggga aagcctgatt accgactcca tcggcgatct ggtcagcgac    540
ctgctcgccg cgctgggccc caaggactat gcgaaaaact atgccggcga agcgtttggc    600
ggcttgctca agacggtggc cgactatgcc ggcgcccatg gcctgagtgg caaggatgtg    660
ctggtcagcg gccacagcct gggcggcctg gcggtcaaca gcatggccga cctgagcacc    720
agcaaatggg cggtttctca aaggacgcc aactacctgg cctacgcctc gcccacccag    780
agcgccggcg ataaggtcct gaatatcggc tacgaaaacg accggtatt ccgtgcgctg    840 gacggctcca ccttcaacct gtcgtccctc ggcgtgcatg acaaggccca cgagtcgacc    900
accgacaaca tcgtcagctt caacgaccac tacgcctcga cgttgtggaa tgtgctgccg    960
ttttccatcg ccaacctgtc gacctgggtg tcgcatttgc cagcgcttac ggcgacggca    1020
tgacgcgtgt gctggaatcg gggttctacg agcaaatgac ccgtgactcg acgattatcg    1080
tcgccaacct gtccgacccg cgcgcgccaa cacctgggt ccaggacctc aaccgcaatg    1140
ccgagccgca cacaggcaat accttcatca tcggcagcga cggcaatgac ctgatccagg    1200
gcggcaaggg cgccggactc atcgaaggcg gcaagggcaa tgacacgatc cgcgacaaca    1260
gcgggcacaa caccttttg ttcagcgggc atttttggcca ggatcggatt atcggctacc    1320
agccgaccga caggctggtg ttccaggcg ccgacggcag caccgacctg cgcgaccacg    1380
cgaaggccgt gggggccgat acggtgctga gttttggcgc cgactcggtg accctggtcg    1440
gggtcgggct gggcggcctg tggagcgagg gtgtgctgat cagttgagg                1489

<210> SEQ ID NO 48
<211> LENGTH: 1489
<212> TYPE: DNA
<213> ORGANISM: Artificial Sequence
<220> FEATURE:
<223> OTHER INFORMATION: NKC - lipase TliA

<400> SEQUENCE: 48
gcgccgaaag cgatgaaact gttgaagaaa ttgctgaaat tacagaaaaa aggcattatg      60
ggtgtatttg actacaagaa cctcggcacc gaagccagca aaaccttgtt cgccgatgcc    120
```

```
accgcaatca cgttgtatac ctatcacaac ctggataacg gcttcgcagt cggctaccag    180
caacatggct tggggctcgg cctgccggcc acactggtcg gggcgttgct cggcagcaca    240
gactcccagg gagtgatccc cggcattccc tggaatcctg actcggaaaa ggccgccctg    300
gacgcggtgc acgcagccgg ttggacgcca atcagcgcca gcgcactggg ctacggcggc    360
aaggtggatg cgcggggcac ttttttttggc gagaaggccg gctacaccac ggcccaggcc    420
gaagtgctgg gcaagtacga tgacgccggc aaactgctcg agatcggcat cggttttcgt    480
ggcacctcgg gccctcggga aagcctgatt accgactcca tcggcgatct ggtcagcgac    540
ctgctcgccg cgctgggccc caaggactat gcgaaaaact atgccggcga agcgtttggc    600
ggcttgctca agacggtggc cgactatgcc ggcgcccatg gcctgagtgg caaggatgtg    660
ctggtcagcg ccacagcct gggcggcctg gcggtcaaca gcatggccga cctgagcacc    720
agcaaatggg cgggtttcta caaggacgcc aactacctgg cctacgcctc gcccacccag    780
agcgccggca taaggtcct gaatatcggc tacgaaaacg acccggtatt ccgtgcgctg    840
gacggctcca ccttcaacct gtcgtccctc ggcgtgcatg acaaggccca cgagtcgacc    900
accgacaaca tcgtcagctt caacgaccac tacgcctcga cgttgtggaa tgtgctgccg    960
ttttccatcg ccaacctgtc gacctgggtg tcgcatttgc cagcgcttac ggcgacggca    1020
tgacgcgtgt gctggaatcg gggttctacg agcaaatgac ccgtgactcg acgattatcg    1080
tcgccaacct gtccgacccg gcgcgcgcca acacctgggt ccaggacctc aaccgcaatg    1140
ccgagccgca cacaggcaat accttcatca tcggcagcga cggcaatgac ctgatccagg    1200
gcggcaaggg cgcggacttc atcgaaggcg gcaagggcaa tgacacgatc cgcgacaaca    1260
gcgggcacaa caccttttg ttcagcgggc attttggcca ggatcggatt atcggctacc    1320
agccgaccga caggctggtg ttccagggcg ccgacgcag caccgacctg cgcgaccacg    1380
cgaaggccgt ggggccgat acggtgctga gtttttggcgc cgactcggtg accctggtcg    1440
gggtcgggct gggcggcctg tggagcgagg gtgtgctgat cagttgagg                1489
```

<210> SEQ ID NO 49
<211> LENGTH: 1489
<212> TYPE: DNA
<213> ORGANISM: Artificial Sequence
<220> FEATURE:
<223> OTHER INFORMATION: NRC - lipase TliA

<400> SEQUENCE: 49

```
gcgccgaaag cgatgcgtct gttgcgtcgc ttgctgcgtt tacagaaaaa aggcattatg     60
ggtgtatttg actacaagaa cctcggcacc gaagccagca aaaccttgtt cgccgatgcc    120
accgcaatca cgttgtatac ctatcacaac ctggataacg gcttcgcagt cggctaccag    180
caacatggct tggggctcgg cctgccggcc acactggtcg gggcgttgct cggcagcaca    240
gactcccagg gagtgatccc cggcattccc tggaatcctg actcggaaaa ggccgccctg    300
gacgcggtgc acgcagccgg ttggacgcca atcagcgcca gcgcactggg ctacggcggc    360
aaggtggatg cgcggggcac ttttttttggc gagaaggccg gctacaccac ggcccaggcc    420
gaagtgctgg gcaagtacga tgacgccggc aaactgctcg agatcggcat cggttttcgt    480
ggcacctcgg gccctcggga aagcctgatt accgactcca tcggcgatct ggtcagcgac    540
ctgctcgccg cgctgggccc caaggactat gcgaaaaact atgccggcga agcgtttggc    600
ggcttgctca agacggtggc cgactatgcc ggcgcccatg gcctgagtgg caaggatgtg    660
```

```
ctggtcagcg ccacagcct gggcggcctg gcggtcaaca gcatggccga cctgagcacc    720
agcaaatggg cgggtttcta caaggacgcc aactacctgg cctacgcctc gcccacccag    780
agcgccggcg ataaggtcct gaatatcggc tacgaaaacg acccggtatt ccgtgcgctg    840
gacggctcca ccttcaacct gtcgtccctc ggcgtgcatg acaaggccca cgagtcgacc    900
accgacaaca tcgtcagctt caacgaccac tacgcctcga cgttgtggaa tgtgctgccg    960
ttttccatcg ccaacctgtc gacctgggtg tcgcatttgc cagcgcttac ggcgacggca   1020
tgacgcgtgt gctggaatcg gggttctacg agcaaatgac ccgtgactcg acgattatcg   1080
tcgccaacct gtccgacccg gcgcgcgcca cacctgggt ccaggacctc aaccgcaatg   1140
ccgagccgca cacaggcaat accttcatca tcggcagcga cggcaatgac ctgatccagg   1200
gcggcaaggg cgcggacttc atcgaaggcg gcaagggcaa tgacacgatc cgcgacaaca   1260
gcgggcacaa cacctttttg ttcagcgggc attttggcca ggatcggatt atcggctacc   1320
agccgaccga caggctggtg ttccagggcg ccgacggcag caccgacctg cgcgaccacg   1380
cgaaggccgt gggggccgat acggtgctga gttttggcgc cgactcggtg accctggtcg   1440
gggtcgggct gggcggcctg tggagcgagg gtgtgctgat cagttgagg               1489
```

```
<210> SEQ ID NO 50
<211> LENGTH: 1085
<212> TYPE: DNA
<213> ORGANISM: Artificial Sequence
<220> FEATURE:
<223> OTHER INFORMATION: Buforin IIb - lipase M37

<400> SEQUENCE: 50
```

```
cgtgctggtc tgcagttccc ggttggtcgt ctgctgcgtc gtctgctgcg tcgtctgctg     60
cgtatgtctt atacaaaaga caactcatg ttggcattca gctatatgag ctactatggc    120
atcactcaca caggttcagc aaaaaaaat gctgagctca tccttaaaaa aatgaaagaa    180
gccttgaaaa catggaagcc ttttcaggaa gatgactggg aagtcgtctg gggtcctgcg    240
gtttatacca tgcctttcac aatcttcaac gatgccatga tgtatgtcat acagaagaaa    300
ggtgctgaag gggaatacgt gatagccatt cgcggcacca atccagtatc aatttcagac    360 tggctgtttta atgatttcat ggtcagcgca atgaagaagt ggccttacgc atccgttgaa    420
ggccgcatac tcaaaatatc cgaaagtacc agctacggac tgaaaacctt acagaaattg    480
aagccaaaat cccatatccc cggcgaaaat aaaacgattc tgcagttcct gaatgaaaag    540
ataggcccag agggtaaagc aaaaatctgt gtaacaggcc acagtaaagg cggcgccttg    600
tcttccactc tggcactgtg gttgaaggac atccaaggag taaaactctc gcaaaacatc    660
gatatctcaa cgattccgtt tgccggacca acagccggta atgctgactt tgccgattac    720
tttgatgatt gtcttggtga tcaatgcacc cgcattgcca actcgttaga tattgtgcct    780
tatgcctgga ataaaattca ttaaaaaaac ttaaatctat atatatttct gaacaagcat    840
cagttaaacc gcttctatat caacgcgctt taatccgtgc aatgatcgca gaaactaaag    900
gtaaaaaata caagcaaatt aaggcggaaa caccaccatt agaaggcaac attaatccta    960
ttcttattga atccttgtg caggcagcat atcagcatgt cgtcggttac ccagaattaa   1020
tgggtatgat ggatgatatt cctttaacag acatattcga agatgcgatc gcgggtttgt   1080
tataa                                                               1085
```

```
<210> SEQ ID NO 51
<211> LENGTH: 1049
```

```
<212> TYPE: DNA
<213> ORGANISM: Artificial Sequence
<220> FEATURE:
<223> OTHER INFORMATION: B0 - lipase M37

<400> SEQUENCE: 51
cgtgctggtc tgcagttccc ggttggtatg tcttatacaa agaacaact  catgttggca      60
ttcagctata tgagctacta tggcatcact cacacaggtt cagcaaaaaa aaatgctgag     120
ctcatcctta aaaaaatgaa agaagccttg aaaacatgga agccttttca ggaagatgac     180
tgggaagtcg tctggggtcc tgcggtttat accatgcctt tcacaatctt caacgatgcc     240
atgatgtatg tcatacagaa gaaaggtgct gaagggggaat acgtgatagc cattcgcggc     300
accaatccag tatcaatttc agactggctg tttaatgatt tcatggtcag cgcaatgaag     360
aagtggcctt acgcatccgt tgaaggccgc atactcaaaa tatccgaaag taccagctac     420
ggactgaaaa ccttacagaa attgaagcca aaatcccata tccccggcga aaataaaacg     480
attctgcagt tcctgaatga aaagatagcc cagagggta aagcaaaaat ctgtgtaaca     540
ggccacagta aaggcggcgc cttgtcttcc actctggcac tgtggttgaa ggacatccaa     600
ggagtaaaac tctcgcaaaa catcgatatc tcaacgattc cgtttgccgg accaacagcc     660
ggtaatgctg actttgccga ttactttgat gattgtcttg gtgatcaatg cacccgcatt     720
gccaactcgt tagatattgt gccttatgcc tggaataaaa ttcattaaaa aaacttaaat     780
ctatatatat ttctgaacaa gcatcagtta aaccgcttct atatcaacgc gctttaatcc     840
gtgcaatgat cgcagaaact aaaggtaaaa aatacaagca aattaaggcg gaaacaccac     900
cattgaagg caacattaat cctattctta ttgaatacct tgtgcaggca gcatatcagc     960
atgtcgtcgg ttacccagaa ttaatgggta tgatggatga tattcctta acagacatat    1020
tcgaagatgc gatcgcgggt ttgttataa                                      1049

<210> SEQ ID NO 52
<211> LENGTH: 1079
<212> TYPE: DNA
<213> ORGANISM: Artificial Sequence
<220> FEATURE:
<223> OTHER INFORMATION: Paracin I - lipase M37

<400> SEQUENCE: 52
aaaggaagag gcaaacaggg aggcaaggtg cgtgcgaagg caaagacacg ttcatccatg      60
tcttatacaa agaacaact  catgttggca ttcagctata tgagctacta tggcatcact     120
cacacaggtt cagcaaaaaa aaatgctgag ctcatcctta aaaaaatgaa agaagccttg     180
aaaacatgga agccttttca ggaagatgac tgggaagtcg tctggggtcc tgcggtttat     240
accatgcctt tcacaatctt caacgatgcc atgatgtatg tcatacagaa gaaaggtgct     300
gaagggggaat acgtgatagc cattcgcggc accaatccag tatcaatttc agactggctg     360
tttaatgatt tcatggtcag cgcaatgaag aagtggcctt acgcatccgt tgaaggccgc     420
atactcaaaa tatccgaaag taccagctac ggactgaaaa ccttacagaa attgaagcca     480
aaatcccata tccccggcga aaataaaacg attctgcagt tcctgaatga aaagataggc     540
ccagagggta aagcaaaaat ctgtgtaaca ggccacagta aaggcggcgc cttgtcttcc     600
actctggcac tgtggttgaa ggacatccaa ggagtaaaac tctcgcaaaa catcgatatc     660
tcaacgattc cgtttgccgg accaacagcc ggtaatgctg actttgccga ttactttgat     720
gattgtcttg gtgatcaatg cacccgcatt gccaactcgt tagatattgt gccttatgcc     780
```

| tggaataaaa ttcattaaaa aaacttaaat ctatatatat ttctgaacaa gcatcagtta | 840 |
| aaccgcttct atatcaacgc gctttaatcc gtgcaatgat cgcagaaact aaaggtaaaa | 900 |
| aatacaagca aattaaggcg gaaacaccac cattagaagg caacattaat cctattctta | 960 |
| ttgaataccct tgtgcaggca gcatatcagc atgtcgtcgg ttacccagaa ttaatgggta | 1020 |
| tgatggatga tattcctta acagacatat tcgaagatgc gatcgcgggt ttgttataa | 1079 |

<210> SEQ ID NO 53
<211> LENGTH: 1079
<212> TYPE: DNA
<213> ORGANISM: Artificial Sequence
<220> FEATURE:
<223> OTHER INFORMATION: NKC - lipase M37

<400> SEQUENCE: 53

| gcgccgaaag cgatgaaact gttgaagaaa ttgctgaaat tacagaaaaa aggcattatg | 60 |
| tcttatacaa aagaacaact catgttggca ttcagctata tgagctacta tggcatcact | 120 |
| cacacaggtt cagcaaaaaa aaatgctgag ctcatcctta aaaaaatgaa agaagccttg | 180 |
| aaaacatgga agcctttttca ggaagatgac tgggaagtcg tctggggtcc tgcggtttat | 240 |
| accatgcctt tcacaatctt caacgatgcc atgatgtatg tcatacagaa gaaaggtgct | 300 |
| gaaggggaat acgtgatagc cattcgcggc accaatccag tatcaatttc agactggctg | 360 |
| tttaatgatt tcatggtcag cgcaatgaag aagtggcctt acgcatccgt tgaaggccgc | 420 |
| atactcaaaa tatccgaaag taccagctac ggactgaaaa ccttacagaa attgaagcca | 480 |
| aaatcccata tccccggcga aaataaaacg attctgcagt tcctgaatga aaagataggc | 540 |
| ccagagggta agcaaaaaat ctgtgtaaca ggccacagta aaggcggcgc cttgtcttcc | 600 |
| actctggcac tgtggttgaa ggacatccaa ggagtaaaac tctcgcaaaa catcgatatc | 660 |
| tcaacgattc cgtttgccgg accaacagcc ggtaatgctg actttgccga ttactttgat | 720 |
| gattgtcttg gtgatcaatg cacccgcatt gccaactcgt tagatattgt gccttatgcc | 780 |
| tggaataaaa ttcattaaaa aaacttaaat ctatatatat ttctgaacaa gcatcagtta | 840 |
| aaccgcttct atatcaacgc gctttaatcc gtgcaatgat cgcagaaact aaaggtaaaa | 900 |
| aatacaagca aattaaggcg gaaacaccac cattagaagg caacattaat cctattctta | 960 |
| ttgaataccct tgtgcaggca gcatatcagc atgtcgtcgg ttacccagaa ttaatgggta | 1020 |
| tgatggatga tattcctta acagacatat tcgaagatgc gatcgcgggt ttgttataa | 1079 |

<210> SEQ ID NO 54
<211> LENGTH: 1079
<212> TYPE: DNA
<213> ORGANISM: Artificial Sequence
<220> FEATURE:
<223> OTHER INFORMATION: NRC - lipase M37

<400> SEQUENCE: 54

| gcgccgaaag cgatgcgtct gttgcgtcgc ttgctgcgtt tacagaaaaa aggcattatg | 60 |
| tcttatacaa aagaacaact catgttggca ttcagctata tgagctacta tggcatcact | 120 |
| cacacaggtt cagcaaaaaa aaatgctgag ctcatcctta aaaaaatgaa agaagccttg | 180 |
| aaaacatgga agcctttttca ggaagatgac tgggaagtcg tctggggtcc tgcggtttat | 240 |
| accatgcctt tcacaatctt caacgatgcc atgatgtatg tcatacagaa gaaaggtgct | 300 |
| gaaggggaat acgtgatagc cattcgcggc accaatccag tatcaatttc agactggctg | 360 |
| tttaatgatt tcatggtcag cgcaatgaag aagtggcctt acgcatccgt tgaaggccgc | 420 |

| atactcaaaa tatccgaaag taccagctac ggactgaaaa ccttacagaa attgaagcca | 480 |
| aaatcccata tccccggcga aaataaaacg attctgcagt tcctgaatga aaagataggc | 540 |
| ccagagggta aagcaaaaat ctgtgtaaca ggccacagta aaggcggcgc cttgtcttcc | 600 |
| actctggcac tgtggttgaa ggacatccaa ggagtaaaac tctcgcaaaa catcgatatc | 660 |
| tcaacgattc cgtttgccgg accaacagcc ggtaatgctg actttgccga ttactttgat | 720 |
| gattgtcttg gtgatcaatg cacccgcatt gccaactcgt tagatattgt gccttatgcc | 780 |
| tggaataaaa ttcattaaaa aaacttaaat ctatatatat ttctgaacaa gcatcagtta | 840 |
| aaccgcttct atatcaacgc gctttaatcc gtgcaatgat cgcagaaact aaaggtaaaa | 900 |
| aatacaagca aattaaggcg gaaacaccac cattagaagg caacattaat cctattctta | 960 |
| ttgaatacct tgtgcaggca gcatatcagc atgtcgtcgg ttacccagaa ttaatgggta | 1020 |
| tgatggatga tattccttta acagacatat tcgaagatgc gatcgcgggt ttgttataa | 1079 |

<210> SEQ ID NO 55
<211> LENGTH: 1495
<212> TYPE: DNA
<213> ORGANISM: Artificial Sequence
<220> FEATURE:
<223> OTHER INFORMATION: lipase TliA - Buforin IIb

<400> SEQUENCE: 55

| atgggtgtat ttgactacaa gaacctcggc accgaagcca gcaaaacctt gttcgccgat | 60 |
| gccaccgcaa tcacgttgta tacctatcac aacctggata acggcttcgc agtcggctac | 120 |
| cagcaacatg gcttggggct cggcctgccg gccacactgg tcgggcgtt gctcggcagc | 180 |
| acagactccc agggagtgat ccccggcatt ccctggaatc ctgactcgga aaaggccgcc | 240 |
| ctggacgcgg tgcacgcagc cggttggacg ccaatcagcg ccagcgcact gggctacggc | 300 |
| ggcaaggtgg atgcgcgggg cacttttttt ggcgagaagg ccggctacac cacgcccag | 360 |
| gccgaagtgc tgggcaagta cgatgacgcc ggcaaactgc tcgagatcgg catcggtttt | 420 |
| cgtggcacct cgggccctcg ggaaagcctg attaccgact ccatcggcga tctggtcagc | 480 |
| gacctgctcg ccgcgctggg ccccaaggac tatgcgaaaa actatgccgg cgaagcgttt | 540 |
| ggcggcttgc tcaagacggt ggccgactat gccggcgccc atggcctgag tggcaaggat | 600 |
| gtgctggtca gcgccacag cctggcggg ctggcggtca acagcatggc cgacctgagc | 660 |
| accagcaaat gggcgggttt ctacaaggac gccaactacc tggcctacgc ctcgcccacc | 720 |
| cagagcgccg gcgataaggt cctgaatatc ggctacgaaa acgacccggt attccgtgcg | 780 |
| ctggacggct ccaccttcaa cctgtcgtcc ctcggcgtgc atgacaaggc ccacgagtcg | 840 |
| accaccgaca acatcgtcag cttcaacgac cactacgcct cgacgttgtg gaatgtgctg | 900 |
| ccgttttcca tcgccaacct gtcgacctgg gtgtcgcatt gccagcgct acggcgacg | 960 |
| gcatgacgcg tgtgctggaa tcggggttct acgagcaaat gacccgtgac tcgacgatta | 1020 |
| tcgtcgccaa cctgtccgac ccggcgcgcg ccaacacctg ggtccaggac ctcaaccgca | 1080 |
| atgccgagcc gcacacaggc aatacccтtca tcatcggcag cgacggcaat gacctgatcc | 1140 |
| agggcggcaa gggcgcggac ttcatcgaag cggcaaggg caatgacacg atccgcgaca | 1200 |
| acagcgggca aacaccttt tgttcagcg ggcattttgg ccaggatcgg attatcggct | 1260 |
| accagccgac cgacaggctg gtgttccagg gcgccgacgg cagcaccgac ctgcgcgacc | 1320 |
| acgcgaaggc cgtgggggcc gatacggtgc tgagttttgg cgccgactcg gtgaccctgg | 1380 |

| | |
|---|---|
| tcggggtcgg gctgggcggc ctgtggagcg agggtgtgct gatcagttga ggcgtgctgg | 1440 |
| tctgcagttc ccggttggtc gtctgctgcg tcgtctgctg cgtcgtctgc tgcgt | 1495 |

<210> SEQ ID NO 56
<211> LENGTH: 1459
<212> TYPE: DNA
<213> ORGANISM: Artificial Sequence
<220> FEATURE:
<223> OTHER INFORMATION: lipase TliA - B0

<400> SEQUENCE: 56

| | |
|---|---|
| atgggtgtat ttgactacaa gaacctcggc accgaagcca gcaaaacctt gttcgccgat | 60 |
| gccaccgcaa tcacgttgta tacctatcac aacctggata acggcttcgc agtcggctac | 120 |
| cagcaacatg gcttggggct cggcctgccg gccacactgg tcggggcgtt gctcggcagc | 180 |
| acagactccc agggagtgat ccccggcatt ccctggaatc ctgactcgga aaaggccgcc | 240 |
| ctggacgcgg tgcacgcagc cggttggacg ccaatcagcg ccagcgcact gggctacggc | 300 |
| ggcaaggtgg atgcgcgggg cacttttttt ggcgagaagg ccggctacac cacggcccag | 360 |
| gccgaagtgc tggcaagta cgatgacgcc ggcaaactgc tcgagatcgg catcggtttt | 420 |
| cgtggcacct cgggccctcg ggaaagcctg attaccgact ccatcggcga tctggtcagc | 480 |
| gacctgctcg ccgcgctggg ccccaaggac tatgccaaaa actatgccgg cgaagcgttt | 540 |
| ggcggcttgc tcaagacggt ggccgactat gccggcgccc atggcctgag tggcaaggat | 600 |
| gtgctggtca gcggccacag cctgggcggc ctggcggtca acagcatggc cgacctgagc | 660 |
| accagcaaat gggcgggttt ctacaaggac gccaactacc tggcctacgc ctcgcccacc | 720 |
| cagagcgccg gcgataaggt cctgaatatc ggctacgaaa acgacccggt attccgtgcg | 780 |
| ctggacggct ccaccttcaa cctgtcgtcc ctcggcgtgc atgacaaggc ccacgagtcg | 840 |
| accaccgaca acatcgtcag cttcaacgac cactacgcct cgacgttgtg aatgtgctg | 900 |
| ccgttttcca tcgccaacct gtcgacctgg gtgtcgcatt gccagcgct acgcgacg | 960 |
| gcatgacgcg tgtgctggaa tcggggttct acagcaaat gacccgtgac tcgacgatta | 1020 |
| tcgtcgccaa cctgtccgac ccggcgcgcg ccaacacctg gtccaggac ctcaaccgca | 1080 |
| atgccgagcc gcacacaggc aatacccttca tcatcggcag cgacggcaat gacctgatcc | 1140 |
| agggcggcaa gggcgcggac ttcatcgaag gcggcaaggg caatgacacg atccgcgaca | 1200 |
| acagcgggca caacaccttt tgttcagcg ggcatttgg ccaggatcgg attatcggct | 1260 |
| accagccgac cgacaggctg gtgttccagg gcgccgacgg cagcaccgac ctgcgcgacc | 1320 |
| acgcgaaggc cgtgggggcc gatacggtgc tgagtttgg cgccgactcg gtgaccctgg | 1380 |
| tcggggtcgg gctgggcggc ctgtggagcg agggtgtgct gatcagttga ggcgtgctgg | 1440 |
| tctgcagttc ccggttggt | 1459 |

<210> SEQ ID NO 57
<211> LENGTH: 1489
<212> TYPE: DNA
<213> ORGANISM: Artificial Sequence
<220> FEATURE:
<223> OTHER INFORMATION: lipase TliA - Paracin I

<400> SEQUENCE: 57

| | |
|---|---|
| atgggtgtat ttgactacaa gaacctcggc accgaagcca gcaaaacctt gttcgccgat | 60 |
| gccaccgcaa tcacgttgta tacctatcac aacctggata acggcttcgc agtcggctac | 120 |
| cagcaacatg gcttggggct cggcctgccg gccacactgg tcggggcgtt gctcggcagc | 180 |

```
acagactccc agggagtgat ccccggcatt ccctggaatc ctgactcgga aaaggccgcc      240
ctggacgcgg tgcacgcagc cggttggacg ccaatcagcg ccagcgcact gggctacggc      300
ggcaaggtgg atgcgcgggg cacttttttt ggcgagaagg ccggctacac cacggcccag      360
gccgaagtgc tgggcaagta cgatgacgcc ggcaaactgc tcgagatcgg catcggtttt      420
cgtggcacct cgggccctcg ggaaagcctg attaccgact ccatcggcga tctggtcagc      480
gacctgctcg ccgcgctggg ccccaaggac tatgcgaaaa actatgccgg cgaagcgttt      540
ggcggcttgc tcaagacggt ggccgactat gccggcgccc atggcctgag tggcaaggat      600
gtgctggtca gcggccacag cctgggcggc ctggcggtca acagcatggc cgacctgagc      660
accagcaaat gggcgggttt ctacaaggac gccaactacc tggcctacgc ctcgcccacc      720
cagagcgccg gcgataaggt cctgaatatc ggctacgaaa acgacccggt attccgtgcg      780
ctggacggct ccaccttcaa cctgtcgtcc ctcggcgtgc atgacaaggc ccacgagtcg      840
accaccgaca catcgtcag cttcaacgac cactacgcct cgacgttgtg gaatgtgctg       900
ccgttttcca tcgccaacct gtcgacctgg gtgtcgcatt gccagcgct acggcgacg       960 gcatgacgcg tgtgctggaa tcggggttct acgagcaaat gacccgtgac tcgacgatta     1020
tcgtcgccaa cctgtccgac ccggcgcgcg ccaacacctg gtccaggac ctcaaccgca     1080 atgccgagcc gcacacaggc aataccttca tcatcggcag cgacggcaat gacctgatcc     1140
agggcggcaa gggcgcggac ttcatcgaag cggcaaggg caatgacacg atccgcgaca     1200
acagcgggca caacaccttt ttgttcagcg ggcattttgg ccaggatcgg attatcggct     1260
accagccgac cgacaggctg tgttccagg cgccgacgg cagcaccgac ctgcgcgacc     1320
acgcgaaggc cgtgggggcc gatacggtgc tgagttttgg cgccgactcg gtgaccctgg     1380
tcggggtcgg gctgggcggc ctgtggagcg agggtgtgct gatcagttga ggaaaggaag     1440
aggcaaacag ggaggcaagg tgcgtgcgaa ggcaaagaca cgttcatcc                 1489
```

<210> SEQ ID NO 58
<211> LENGTH: 1489
<212> TYPE: DNA
<213> ORGANISM: Artificial Sequence
<220> FEATURE:
<223> OTHER INFORMATION: lipase TliA - NRC

<400> SEQUENCE: 58

```
atgggtgtat ttgactacaa gaacctcggc accgaagcca gcaaaacctt gttcgccgat       60
gccaccgcaa tcacgttgta tacctatcac aacctggata acggcttcgc agtcggctac      120
cagcaacatg gcttggggct cggcctgccg gccacactgg tcggggcgtt gctcggcagc      180
acagactccc agggagtgat ccccggcatt ccctggaatc ctgactcgga aaaggccgcc      240
ctggacgcgg tgcacgcagc cggttggacg ccaatcagcg ccagcgcact gggctacggc      300
ggcaaggtgg atgcgcgggg cacttttttt ggcgagaagg ccggctacac cacggcccag      360
gccgaagtgc tgggcaagta cgatgacgcc ggcaaactgc tcgagatcgg catcggtttt      420
cgtggcacct cgggccctcg ggaaagcctg attaccgact ccatcggcga tctggtcagc      480
gacctgctcg ccgcgctggg ccccaaggac tatgcgaaaa actatgccgg cgaagcgttt      540
ggcggcttgc tcaagacggt ggccgactat gccggcgccc atggcctgag tggcaaggat      600
gtgctggtca gcggccacag cctgggcggc ctggcggtca acagcatggc cgacctgagc      660
accagcaaat gggcgggttt ctacaaggac gccaactacc tggcctacgc ctcgcccacc      720
```

| | |
|---|---|
| cagagcgccg gcgataaggt cctgaatatc ggctacgaaa cgacccggt attccgtgcg | 780 |
| ctggacggct ccaccttcaa cctgtcgtcc ctcggcgtgc atgacaaggc ccacgagtcg | 840 |
| accaccgaca acatcgtcag cttcaacgac cactacgcct cgacgttgtg gaatgtgctg | 900 |
| ccgttttcca tcgccaacct gtcgacctgg gtgtcgcatt tgccagcgct tacggcgacg | 960 |
| gcatgacgcg tgtgctggaa tcggggttct acgagcaaat gacccgtgac tcgacgatta | 1020 |
| tcgtcgccaa cctgtccgac ccggcgcgcg ccaacacctg gtccaggac ctcaaccgca | 1080 |
| atgccgagcc gcacacaggc aataccttca tcatcggcag cgacggcaat gacctgatcc | 1140 |
| agggcggcaa gggcgcggac ttcatcgaag gcggcaaggg caatgacacg atccgcgaca | 1200 |
| acagcgggca caacaccttt tgttcagcg ggcattttgg ccaggatcgg attatcggct | 1260 |
| accagccgac cgacaggctg gtgttccagg gcgccgacgg cagcaccgac ctgcgcgacc | 1320 |
| acgcgaaggc cgtgggggcc gatacggtgc tgagttttgg cgccgactcg gtgaccctgg | 1380 |
| tcggggtcgg gctgggcggc ctgtggagcg agggtgtgct gatcagttga gggcgccgaa | 1440 |
| agcgatgaaa ctgttgaaga aattgctgaa attacagaaa aaaggcatt | 1489 |

<210> SEQ ID NO 59
<211> LENGTH: 1489
<212> TYPE: DNA
<213> ORGANISM: Artificial Sequence
<220> FEATURE:
<223> OTHER INFORMATION: lipase TliA - NRC

<400> SEQUENCE: 59

| | |
|---|---|
| atgggtgtat tgactacaa gaacctcggc accgaagcca gcaaaacctt gttcgccgat | 60 |
| gccaccgcaa tcacgttgta tacctatcac aacctggata acggcttcgc agtcggctac | 120 |
| cagcaacatg gcttggggct cggcctgccg gccacactgg tcgggggcgtt gctcggcagc | 180 |
| acagactccc agggagtgat ccccggcatt ccctggaatc ctgactcgga aaaggccgcc | 240 |
| ctggacgcgt tgcacgcagc cggttggacg ccaatcagcg ccagcgcact gggctacggc | 300 |
| ggcaaggtgg atgcgcgggg cacttttttt ggcgagaagg ccggctacac cacggcccag | 360 |
| gccgaagtgc tgggcaagta cgatgacgcc ggcaaactgc tcgagatcgg catcggtttt | 420 |
| cgtggcacct cgggccctcg ggaaagcctg attaccgact ccatcggcga tctggtcagc | 480 |
| gacctgctcg ccgcgctggg ccccaaggac tatgcgaaaa actatgccgg cgaagcgttt | 540 |
| ggcggcttgc tcaagacggt ggccgactat gccggcgccc atggcctgag tggcaaggat | 600 |
| gtgctggtca gcgccacag cctgggcggc ctggcggtca acagcatggc cgacctgagc | 660 |
| accagcaaat gggcgggttt ctacaaggac gccaactacc tggcctacgc ctcgcccacc | 720 |
| cagagcgccg gcgataaggt cctgaatatc ggctacgaaa cgacccggt attccgtgcg | 780 |
| ctggacggct ccaccttcaa cctgtcgtcc ctcggcgtgc atgacaaggc ccacgagtcg | 840 |
| accaccgaca acatcgtcag cttcaacgac cactacgcct cgacgttgtg gaatgtgctg | 900 |
| ccgttttcca tcgccaacct gtcgacctgg gtgtcgcatt tgccagcgct tacggcgacg | 960 |
| gcatgacgcg tgtgctggaa tcggggttct acgagcaaat gacccgtgac tcgacgatta | 1020 |
| tcgtcgccaa cctgtccgac ccggcgcgcg ccaacacctg gtccaggac ctcaaccgca | 1080 |
| atgccgagcc gcacacaggc aataccttca tcatcggcag cgacggcaat gacctgatcc | 1140 |
| agggcggcaa gggcgcggac ttcatcgaag gcggcaaggg caatgacacg atccgcgaca | 1200 |
| acagcgggca caacaccttt tgttcagcg ggcattttgg ccaggatcgg attatcggct | 1260 |
| accagccgac cgacaggctg gtgttccagg gcgccgacgg cagcaccgac ctgcgcgacc | 1320 |

```
acgcgaaggc cgtgggggcc gatacggtgc tgagttttgg cgccgactcg gtgaccctgg   1380
tcggggtcgg gctgggcggc ctgtggagcg agggtgtgct gatcagttga gggcgccgaa   1440
agcgatgcgt ctgttgcgtc gcttgctgcg tttacagaaa aaaggcatt               1489
```

<210> SEQ ID NO 60
<211> LENGTH: 1085
<212> TYPE: DNA
<213> ORGANISM: Artificial Sequence
<220> FEATURE:
<223> OTHER INFORMATION: lipase M37 - Buforin IIb

<400> SEQUENCE: 60

```
atgtcttata caaaagaaca actcatgttg gcattcagct atatgagcta ctatggcatc    60
actcacacag gttcagcaaa aaaaaatgct gagctcatcc ttaaaaaaat gaagaagcc    120 ttgaaaacat ggaagccttt tcaggaagat gactgggaag tcgtctgggg tcctgcggtt   180
tataccatgc ctttcacaat cttcaacgat gccatgatgt atgtcataca aagaaaggt    240 gctgaagggg aatacgtgat agccattcgc ggcaccaatc cagtatcaat tcagactgg    300 ctgtttaatg atttcatggt cagcgcaatg aagaagtggc cttacgcatc cgttgaaggc   360
cgcatactca aaatatccga agtaccagc tacggactga aaaccttaca gaaattgaag   420
ccaaaatccc atatccccgg cgaaaataaa acgattctgc agttcctgaa tgaaaagata   480
ggcccagagg gtaaagcaaa aatctgtgta acaggccaca gtaaaggcgg cgccttgtct   540
tccactctgg cactgtggtt gaaggacatc caaggagtaa aactctcgca aaacatcgat   600
atctcaacga ttccgtttgc cggaccaaca gccggtaatg ctgactttgc cgattacttt   660
gatgattgtc ttggtgatca atgcacccgc attgccaact cgttagatat tgtgccttat   720
gcctggaata aaattcatta aaaaaactta aatctatata tatttctgaa caagcatcag   780
ttaaaccgct tctatatcaa cgcgctttaa tccgtgcaat gatcgcagaa actaaaggta   840
aaaaatacaa gcaaattaag gcggaaacac caccattaga aggcaacatt aatcctattc   900
ttattgaata ccttgtgcag gcagcatatc agcatgtcgt cggttaccca gaattaatgg   960
gtatgatgga tgatattcct ttaacagaca tattcgaaga tgcgatcgcg ggtttgttat  1020
aacgtgctgg tctgcagttc ccggttggtc gtctgctgcg tcgtctgctg cgtcgtctgc  1080
tgcgt                                                              1085
```

<210> SEQ ID NO 61
<211> LENGTH: 1049
<212> TYPE: DNA
<213> ORGANISM: Artificial Sequence
<220> FEATURE:
<223> OTHER INFORMATION: lipase M37 - B0

<400> SEQUENCE: 61

```
atgtcttata caaaagaaca actcatgttg gcattcagct atatgagcta ctatggcatc    60
actcacacag gttcagcaaa aaaaaatgct gagctcatcc ttaaaaaaat gaagaagcc    120 ttgaaaacat ggaagccttt tcaggaagat gactgggaag tcgtctgggg tcctgcggtt   180
tataccatgc ctttcacaat cttcaacgat gccatgatgt atgtcataca aagaaaggt    240 gctgaagggg aatacgtgat agccattcgc ggcaccaatc cagtatcaat tcagactgg    300 ctgtttaatg atttcatggt cagcgcaatg aagaagtggc cttacgcatc cgttgaaggc   360
cgcatactca aaatatccga agtaccagc tacggactga aaaccttaca gaaattgaag   420
```

| | |
|---|---|
| ccaaaatccc atatccccgg cgaaaataaa acgattctgc agttcctgaa tgaaaagata | 480 |
| ggcccagagg gtaaagcaaa aatctgtgta acaggccaca gtaaaggcgg cgccttgtct | 540 |
| tccactctgg cactgtggtt gaaggacatc caaggagtaa aactctcgca aaacatcgat | 600 |
| atctcaacga ttccgtttgc cggaccaaca gccgtaatg ctgactttgc cgattacttt | 660 |
| gatgattgtc ttggtgatca atgcacccgc attgccaact cgttagatat tgtgccttat | 720 |
| gcctggaata aaattcatta aaaaaactta aatctatata tatttctgaa caagcatcag | 780 |
| ttaaaccgct tctatatcaa cgcgctttaa tccgtgcaat gatcgcagaa actaaaggta | 840 |
| aaaaatacaa gcaaattaag gcggaaacac caccattaga aggcaacatt aatcctattc | 900 |
| ttattgaata ccttgtgcag gcagcatatc agcatgtcgt cggttaccca gaattaatgg | 960 |
| gtatgatgga tgatattcct ttaacagaca tattcgaaga tgcgatcgcg ggtttgttat | 1020 |
| aacgtgctgg tctgcagttc ccggttggt | 1049 |

<210> SEQ ID NO 62
<211> LENGTH: 1079
<212> TYPE: DNA
<213> ORGANISM: Artificial Sequence
<220> FEATURE:
<223> OTHER INFORMATION: lipase M37 - Paracin I

<400> SEQUENCE: 62

| | |
|---|---|
| atgtcttata caaagaaca actcatgttg gcattcagct atatgagcta ctatggcatc | 60 |
| actcacacag gttcagcaaa aaaaaatgct gagctcatcc ttaaaaaaat gaagaagcc | 120 |
| ttgaaaacat ggaagccttt tcaggaagat gactgggaag tcgtctgggg tcctgcggtt | 180 |
| tataccatgc ctttcacaat cttcaacgat gccatgatgt atgtcataca gaagaaaggt | 240 |
| gctgaagggg aatacgtgat agccattcgc ggcaccaatc cagtatcaat ttcagactgg | 300 |
| ctgtttaatg atttcatggt cagcgcaatg aagaagtggc cttacgcatc cgttgaaggc | 360 |
| cgcatactca aaatatccga aagtaccagc tacggactga aaaccttaca gaaattgaag | 420 |
| ccaaaatccc atatccccgg cgaaaataaa acgattctgc agttcctgaa tgaaaagata | 480 |
| ggcccagagg gtaaagcaaa aatctgtgta acaggccaca gtaaaggcgg cgccttgtct | 540 |
| tccactctgg cactgtggtt gaaggacatc caaggagtaa aactctcgca aaacatcgat | 600 |
| atctcaacga ttccgtttgc cggaccaaca gccgtaatg ctgactttgc cgattacttt | 660 |
| gatgattgtc ttggtgatca atgcacccgc attgccaact cgttagatat tgtgccttat | 720 |
| gcctggaata aaattcatta aaaaaactta aatctatata tatttctgaa caagcatcag | 780 |
| ttaaaccgct tctatatcaa cgcgctttaa tccgtgcaat gatcgcagaa actaaaggta | 840 |
| aaaaatacaa gcaaattaag gcggaaacac caccattaga aggcaacatt aatcctattc | 900 |
| ttattgaata ccttgtgcag gcagcatatc agcatgtcgt cggttaccca gaattaatgg | 960 |
| gtatgatgga tgatattcct ttaacagaca tattcgaaga tgcgatcgcg ggtttgttat | 1020 |
| aaaaaggaag aggcaaacag ggaggcaagg tgcgtgcgaa ggcaaagaca cgttcatcc | 1079 |

<210> SEQ ID NO 63
<211> LENGTH: 1079
<212> TYPE: DNA
<213> ORGANISM: Artificial Sequence
<220> FEATURE:
<223> OTHER INFORMATION: lipase M37 - NKC

<400> SEQUENCE: 63

| | |
|---|---|
| atgtcttata caaagaaca actcatgttg gcattcagct atatgagcta ctatggcatc | 60 |

```
actcacacag gttcagcaaa aaaaaatgct gagctcatcc ttaaaaaaat gaaagaagcc      120
ttgaaaacat ggaagccttt tcaggaagat gactgggaag tcgtctgggg tcctgcggtt      180
tataccatgc ctttcacaat cttcaacgat gccatgatgt atgtcataca aagaaaggt       240 gctgaagggg aatacgtgat agccattcgc ggcaccaatc cagtatcaat ttcagactgg      300
ctgtttaatg atttcatggt cagcgcaatg aagaagtggc cttacgcatc cgttgaaggc      360
cgcatactca aaatatccga aagtaccagc tacggactga aaaccttaca gaaattgaag      420
ccaaaatccc atatccccgg cgaaaataaa acgattctgc agttcctgaa tgaaagata       480 ggcccagagg gtaaagcaaa atctgtgta acaggccaca gtaaaggcgg cgccttgtct       540
tccactctgg cactgtggtt gaaggacatc caaggagtaa aactctcgca aacatcgat       600 atctcaacga ttccgtttgc cggaccaaca gccgtaatg ctgactttgc cgattacttt       660
gatgattgtc ttggtgatca atgcacccgc attgccaact cgttagatat tgtgccttat      720
gcctggaata aaattcatta aaaaaactta aatctatata tatttctgaa caagcatcag      780
ttaaaccgct tctatatcaa cgcgctttaa tccgtgcaat gatcgcagaa actaaaggta      840
aaaaatacaa gcaaattaag gcggaaacac caccattaga aggcaacatt aatcctattc      900
ttattgaata ccttgtgcag gcagcatatc agcatgtcgt cggttaccca gaattaatgg      960
gtatgatgga tgatattcct ttaacagaca tattcgaaga tgcgatcgcg ggtttgttat     1020
aagcgccgaa agcgatgaaa ctgttgaaga aattgctgaa attacagaaa aaaggcatt      1079
```

<210> SEQ ID NO 64
<211> LENGTH: 1079
<212> TYPE: DNA
<213> ORGANISM: Artificial Sequence
<220> FEATURE:
<223> OTHER INFORMATION: lipase M37 - NRC

<400> SEQUENCE: 64

```
atgtcttata caaagaaca actcatgttg gcattcagct atatgagcta ctatggcatc       60
actcacacag gttcagcaaa aaaaaatgct gagctcatcc ttaaaaaaat gaaagaagcc      120
ttgaaaacat ggaagccttt tcaggaagat gactgggaag tcgtctgggg tcctgcggtt      180
tataccatgc ctttcacaat cttcaacgat gccatgatgt atgtcataca aagaaaggt       240 gctgaagggg aatacgtgat agccattcgc ggcaccaatc cagtatcaat ttcagactgg      300
ctgtttaatg atttcatggt cagcgcaatg aagaagtggc cttacgcatc cgttgaaggc      360
cgcatactca aaatatccga aagtaccagc tacggactga aaaccttaca gaaattgaag      420
ccaaaatccc atatccccgg cgaaaataaa acgattctgc agttcctgaa tgaaagata       480 ggcccagagg gtaaagcaaa atctgtgta acaggccaca gtaaaggcgg cgccttgtct       540
tccactctgg cactgtggtt gaaggacatc caaggagtaa aactctcgca aacatcgat       600 atctcaacga ttccgtttgc cggaccaaca gccgtaatg ctgactttgc cgattacttt       660
gatgattgtc ttggtgatca atgcacccgc attgccaact cgttagatat tgtgccttat      720
gcctggaata aaattcatta aaaaaactta aatctatata tatttctgaa caagcatcag      780
ttaaaccgct tctatatcaa cgcgctttaa tccgtgcaat gatcgcagaa actaaaggta      840
aaaaatacaa gcaaattaag gcggaaacac caccattaga aggcaacatt aatcctattc      900
ttattgaata ccttgtgcag gcagcatatc agcatgtcgt cggttaccca gaattaatgg      960
gtatgatgga tgatattcct ttaacagaca tattcgaaga tgcgatcgcg ggtttgttat     1020
```
aagcgccgaa agcgatgcgt ctgttgcgtc gcttgctgcg tttacagaaa aaaggcatt    1079

<210> SEQ ID NO 65
<211> LENGTH: 1558
<212> TYPE: DNA
<213> ORGANISM: Artificial Sequence
<220> FEATURE:
<223> OTHER INFORMATION: Buforin IIb - lipase TliA - Buforin IIb

<400> SEQUENCE: 65

| | | | | | |
|---|---|---|---|---|---|
| cgtgctggtc | tgcagttccc | ggttggtcgt | ctgctgcgtc | gtctgctgcg | tcgtctgctg | 60 |
| cgtatgggtg | tatttgacta | caagaaccct | ggcaccgaag | ccagcaaaac | cttgttcgcc | 120 |
| gatgccaccg | caatcacgtt | gtataccttat | cacaacctgg | ataacggctt | cgcagtcggc | 180 |
| taccagcaac | atggcttggg | gctcggcctg | ccggccacac | tggtcggggc | gttgctcggc | 240 |
| agcacagact | cccagggagt | gatccccggc | attccctgga | atcctgactc | ggaaaaggcc | 300 |
| gccctggacg | cggtgcacgc | agccggttgg | acgccaatca | gcgccagcgc | actgggctac | 360 |
| ggcggcaagg | tggatgcgcg | ggcacttttt | tttggcgaga | aggccggcta | caccacggcc | 420 |
| caggccgaag | tgctgggcaa | gtacgatgac | gccggcaaac | tgctcgagat | cggcatcggt | 480 |
| tttcgtggca | cctcgggccc | tcgggaaagc | ctgattaccg | actccatcgg | cgatctggtc | 540 |
| agcgacctgc | tcgccgcgct | gggccccaag | gactatgcga | aaaactatgc | cggcgaagcg | 600 |
| tttggcggct | tgctcaagac | ggtggccgac | tatgccggcg | cccatggcct | gagtggcaag | 660 |
| gatgtgctgg | tcagcggcca | cagcctgggc | ggcctggcgg | tcaacagcat | ggccgacctg | 720 |
| agcaccagca | atgggcgggt | tttctacaag | gacgccaact | acctggccta | cgcctcgccc | 780 |
| acccagagcg | ccggcgataa | ggtcctgaat | atcggctacg | aaaacgaccc | ggtattccgt | 840 |
| gcgctggacg | gctccacctt | caacctgtcg | tccctcggcg | tgcatgacaa | ggcccacgag | 900 |
| tcgaccaccg | acaacatcgt | cagcttcaac | gaccactacg | cctcgacgtt | gtggaatgtg | 960 |
| ctgccgtttt | ccatcgccaa | cctgtcgacc | tgggtgtcgc | atttgccagc | gcttacggcg | 1020 |
| acggcatgac | gcgtgtgctg | gaatcggggt | tctacgagca | aatgacccgt | gactcgacga | 1080 |
| ttatcgtcgc | caacctgtcc | gaccggcgcg | cgccaacac | ctgggtccag | gacctcaacc | 1140 |
| gcaatgccga | gccgcacaca | ggcaatacct | tcatcatcgg | cagcgacggc | aatgacctga | 1200 |
| tccagggcgg | caagggcgcg | gacttcatcg | aaggcggcaa | gggcaatgac | acgatccgcg | 1260 |
| acaacagcgg | gcacaacacc | ttttttgttca | gcgggcattt | tggccaggat | cggattatcg | 1320 |
| gctaccagcc | gaccgacagg | ctggtgttcc | agggcgccga | cggcagcacc | gacctgcgcg | 1380 |
| accacgcgaa | ggccgtgggg | gccgatacgg | tgctgagttt | tggcgccgac | tcggtgaccc | 1440 |
| tggtcggggt | cgggctgggc | ggcctgtgga | gcgagggtgt | gctgatcagt | tgaggcgtgc | 1500 |
| tggtctgcag | ttcccggttg | gtcgtctgct | gcgtcgtctg | ctgcgtcgtc | tgctgcgt | 1558 |

<210> SEQ ID NO 66
<211> LENGTH: 1486
<212> TYPE: DNA
<213> ORGANISM: Artificial Sequence
<220> FEATURE:
<223> OTHER INFORMATION: B0 - lipase TliA - B0

<400> SEQUENCE: 66

| | | | | | |
|---|---|---|---|---|---|
| cgtgctggtc | tgcagttccc | ggttggtatg | ggtgtatttg | actacaagaa | cctcggcacc | 60 |
| gaagccagca | aaaccttgtt | cgccgatgcc | accgcaatca | cgttgtatac | ctatcacaac | 120 |
| ctggataacg | gcttcgcagt | cggctaccag | caacatggct | tggggctcgg | cctgccggcc | 180 |

```
acactggtcg gggcgttgct cggcagcaca gactcccagg gagtgatccc cggcattccc    240
tggaatcctg actcggaaaa ggccgccctg gacgcggtgc acgcagccgg ttggacgcca    300
atcagcgcca gcgcactggg ctacggcggc aaggtggatg cgcggggcac ttttttttggc   360 gagaaggccg gctacaccac ggcccaggcc gaagtgctgg gcaagtacga tgacgccggc    420
aaactgctcg agatcggcat cggttttcgt ggcacctcgg ccctcgggga aagcctgatt    480
accgactcca tcggcgatct ggtcagcgac ctgctcgccg cgctgggccc caaggactat    540
gcgaaaaact atgccggcga agcgtttggc ggcttgctca agacggtggc cgactatgcc    600
ggcgcccatg gcctgagtgg caaggatgtg ctggtcagcg ccacagcct gggcggcctg     660 gcggtcaaca gcatggccga cctgagcacc agcaaatggg cgggtttcta caaggacgcc    720
aactacctgg cctacgcctc gcccacccag agcgccggcg ataaggtcct gaatatcggc    780
tacgaaaacg acccggtatt ccgtgcgctg gacggctcca ccttcaacct gtcgtccctc    840
ggcgtgcatg acaaggccca cgagtcgacc accgacaaca tcgtcagctt caacgaccac    900
tacgcctcga cgttgtggaa tgtgctgccg ttttccatcg ccaacctgtc gacctgggtg    960
tcgcatttgc cagcgcttac ggcgacggca tgacgcgtgt gctggaatcg gggttctacg   1020
agcaaatgac ccgtgactcg acgattatcg tcgccaacct gtccgacccg gcgcgcgcca   1080
acacctgggt ccaggacctc aaccgcaatg ccgagccgca cacaggcaat accttcatca   1140
tcggcagcga cggcaatgac ctgatccagg cggcaaggg cgcggacttc atcgaaggcg    1200
gcaagggcaa tgacacgatc cgcgacaaca gcgggcacaa cacctttttg ttcagcgggc   1260
attttggcca ggatcggatt atcggctacc agccgaccga caggctggtg ttccagggcg   1320
ccgacggcag caccgacctg cgcgaccacg cgaaggccgt gggggccgat acggtgctga   1380
gttttggcgc cgactcggtg accctggtcg gggtcgggct gggcggcctg tggagcgagg   1440
gtgtgctgat cagttgaggc gtgctggtct gcagttcccg gttggt                  1486
```

<210> SEQ ID NO 67
<211> LENGTH: 1546
<212> TYPE: DNA
<213> ORGANISM: Artificial Sequence
<220> FEATURE:
<223> OTHER INFORMATION: Paracin I - lipase TliA - Paracin I

<400> SEQUENCE: 67

```
aaaggaagag gcaaacaggg aggcaaggtg cgtgcgaagg caaagacacg ttcatccatg     60
ggtgtatttg actacaagaa cctcggcacc gaagccagca aaaccttgtt cgccgatgcc    120
accgcaatca cgttgtatac ctatcacaac ctggataacg gcttcgcagt cggctaccag    180
caacatggct gggggctcgg cctgccggcc acactggtcg gggcgttgct cggcagcaca    240
gactcccagg gagtgatccc cggcattccc tggaatcctg actcggaaaa ggccgccctg    300
gacgcggtgc acgcagccgg ttggacgcca atcagcgcca gcgcactggg ctacggcggc    360
aaggtggatg cgcggggcac ttttttttggc gagaaggccg gctacaccac ggcccaggcc   420
gaagtgctgg gcaagtacga tgacgccggc aaactgctcg agatcggcat cggttttcgt    480
ggcacctcgg ccctcgggga aagcctgatt accgactcca tcggcgatct ggtcagcgac    540
ctgctcgccg cgctgggccc caaggactat gcgaaaaact atgccggcga agcgtttggc    600
ggcttgctca agacggtggc cgactatgcc ggcgcccatg gcctgagtgg caaggatgtg    660
ctggtcagcg ccacagcct gggcggcctg gcggtcaaca gcatggccga cctgagcacc     720
```

| | |
|---|---|
| agcaaatggg cgggtttcta caaggacgcc aactacctgg cctacgcctc gcccacccag | 780 |
| agcgccggcg ataaggtcct gaatatcggc tacgaaaacg acccggtatt ccgtgcgctg | 840 |
| gacggctcca ccttcaacct gtcgtccctc ggcgtgcatg acaaggccca cgagtcgacc | 900 |
| accgacaaca tcgtcagctt caacgaccac tacgcctcga cgttgtggaa tgtgctgccg | 960 |
| ttttccatcg ccaacctgtc gacctggtg tcgcatttgc cagcgcttac ggcgacggca | 1020 |
| tgacgcgtgt gctggaatcg gggttctacg agcaaatgac ccgtgactcg acgattatcg | 1080 |
| tcgccaacct gtccgacccg gcgcgcgcca cacctgggt ccaggacctc aaccgcaatg | 1140 |
| ccgagccgca cacaggcaat accttcatca tcggcagcga cggcaatgac ctgatccagg | 1200 |
| gcggcaaggg cgcggacttc atcgaaggcg gcaagggcaa tgacacgatc cgcgacaaca | 1260 |
| gcgggcacaa caccttttg ttcagcgggc attttggcca ggatcggatt atcggctacc | 1320 |
| agccgaccga caggctggtg ttccaggcg ccgacggcag caccgacctg cgcgaccacg | 1380 |
| cgaaggccgt gggggccgat acggtgctga gttttggcgc cgactcggtg accctggtcg | 1440 |
| gggtcgggct gggcggcctg tggagcgagg gtgtgctgat cagttgagga aaggaagagg | 1500 |
| caaacaggga ggcaaggtgc gtgcgaaggc aaagacacgt tcatcc | 1546 |

<210> SEQ ID NO 68
<211> LENGTH: 1546
<212> TYPE: DNA
<213> ORGANISM: Artificial Sequence
<220> FEATURE:
<223> OTHER INFORMATION: NKC - lipase TliA - NKC

<400> SEQUENCE: 68

| | |
|---|---|
| gcgccgaaag cgatgaaact gttgaagaaa ttgctgaaat tacagaaaaa aggcattatg | 60 |
| ggtgtatttg actacaagaa cctcggcacc gaagccagca aaaccttgtt cgccgatgcc | 120 |
| accgcaatca cgttgtatac ctatcacaac ctggataacg gcttcgcagt cggctaccag | 180 |
| caacatggct tggggctcgg cctgccggcc acactggtcg gggcgttgct cggcagcaca | 240 |
| gactcccagg gagtgatccc cggcattccc tggaatcctg actcggaaaa ggccgccctg | 300 |
| gacgcggtgc acgcagccgg ttggacgcca atcagcgcca gcgcactggg ctacggcggc | 360 |
| aaggtggatg cgcggggcac tttttttggc gagaaggccg gctacaccac ggcccaggcc | 420 |
| gaagtgctgg gcaagtacga tgacgccggc aaactgctcg agatcggcat cggttttcgt | 480 |
| ggcacctcgg gccctcggga agcctgatt accgactcca tcggcgatct ggtcagcgac | 540 |
| ctgctcgccg cgctgggccc caaggactat gcgaaaaact atgccggcga agcgtttggc | 600 |
| ggcttgctca agacggtggc cgactatgcc ggcgcccatg gcctgagtgg caaggatgtg | 660 |
| ctggtcagcg gccacagcct gggcggcctg cgcgtcaaca gcatggccga cctgagcacc | 720 |
| agcaaatggg cgggtttcta caaggacgcc aactacctgg cctacgcctc gcccacccag | 780 |
| agcgccggcg ataaggtcct gaatatcggc tacgaaaacg acccggtatt ccgtgcgctg | 840 |
| gacggctcca ccttcaacct gtcgtccctc ggcgtgcatg acaaggccca cgagtcgacc | 900 |
| accgacaaca tcgtcagctt caacgaccac tacgcctcga cgttgtggaa tgtgctgccg | 960 |
| ttttccatcg ccaacctgtc gacctggtg tcgcatttgc cagcgcttac ggcgacggca | 1020 |
| tgacgcgtgt gctggaatcg gggttctacg agcaaatgac ccgtgactcg acgattatcg | 1080 |
| tcgccaacct gtccgacccg gcgcgcgcca cacctgggt ccaggacctc aaccgcaatg | 1140 |
| ccgagccgca cacaggcaat accttcatca tcggcagcga cggcaatgac ctgatccagg | 1200 |
| gcggcaaggg cgcggacttc atcgaaggcg gcaagggcaa tgacacgatc cgcgacaaca | 1260 |

```
gcgggcacaa caccttttg ttcagcgggc attttggcca ggatcggatt atcggctacc    1320
agccgaccga caggctggtg ttccagggcg ccgacggcag caccgacctg cgcgaccacg    1380
cgaaggccgt gggggccgat acggtgctga gttttggcgc cgactcggtg accctggtcg    1440
gggtcgggct gggcggcctg tggagcgagg gtgtgctgat cagttgaggg cgccgaaagc    1500
gatgaaactg ttgaagaaat tgctgaaatt acagaaaaaa ggcatt                   1546
```

<210> SEQ ID NO 69
<211> LENGTH: 1546
<212> TYPE: DNA
<213> ORGANISM: Artificial Sequence
<220> FEATURE:
<223> OTHER INFORMATION: NRC - lipase TliA - NRC

<400> SEQUENCE: 69

```
gcgccgaaag cgatgcgtct gttgcgtcgc ttgctgcgtt tacagaaaaa aggcattatg     60
ggtgtatttg actacaagaa cctcggcacc gaagccagca aaaccttgtt cgccgatgcc    120
accgcaatca cgttgtatac ctatcacaac ctggataacg gcttcgcagt cggctaccag    180
caacatggct gggctcgg cctgccggcc acactggtcg gggcgttgct cggcagcaca    240
gactcccagg gagtgatccc cggcattccc tggaatcctg actcggaaaa ggccgccctg    300
gacgcggtgc acgcagccgg ttggacgcca atcagcgcca cgcactgggc tacggcggc    360 aaggtggatg cgcggggcac ttttttggc gagaaggccg gctacaccac ggcccaggcc    420
gaagtgctgg gcaagtacga tgacgccggc aaactgctcg agatcggcat cggttttcgt    480
ggcacctcgg gccctcggga agcctgatt accgactcca tcggcgatct ggtcagcgac    540
ctgctcgccg cgctgggccc caaggactat gcgaaaaact atgccggcga agcgtttggc    600
ggcttgctca agacggtggc cgactatgcc ggcgcccatg gcctgagtgg caaggatgtg    660
ctggtcagcg gccacagcct gggcggcctg gcggtcaaca gcatggccga cctgagcacc    720
agcaaatggg cgggttttcta caaggacgcc aactacctgg cctacgcctc gcccacccag    780
agcgccggcg ataaggtcct gaatatcggc tacgaaaacg accggtatt ccgtgcgctg    840 gacggctcca ccttcaacct gtcgtccctc ggcgtgcatg acaaggccca cgagtcgacc    900
accgacaaca tcgtcagctt caacgaccac tacgcctcga cgttgtggaa tgtgctgccg    960
ttttccatcg ccaacctgtc gacctgggtg tcgcatttgc cagcgcttac ggcgacggca   1020
tgacgcgtgt gctggaatcg gggttctacg agcaaatgac ccgtgactcg acgattatcg   1080
tcgccaacct gtccgacccg gcgcgcgcca cacctgggt ccaggactc aaccgcaatg    1140 ccgagccgca cacaggcaat accttcatca tcggcagcga cggcaatgac ctgatccagg   1200
gcggcaaggg cgcggacttc atcgaaggcg gcaaggcaa tgcacgatc cgcgacaaca   1260 gcgggcacaa caccttttg ttcagcgggc attttggcca ggatcggatt atcggctacc   1320
agccgaccga caggctggtg ttccagggcg ccgacggcag caccgacctg cgcgaccacg   1380
cgaaggccgt gggggccgat acggtgctga gttttggcgc cgactcggtg accctggtcg   1440
gggtcgggct gggcggcctg tggagcgagg gtgtgctgat cagttgaggg cgccgaaagc   1500
gatgcgtctg ttgcgtcgct tgctgcgttt acagaaaaaa ggcatt                   1546
```

<210> SEQ ID NO 70
<211> LENGTH: 1148
<212> TYPE: DNA
<213> ORGANISM: Artificial Sequence
<220> FEATURE:

<223> OTHER INFORMATION: Buforin IIb - lipase M37 - Buforin IIb

<400> SEQUENCE: 70

```
cgtgctggtc tgcagttccc ggttggtcgt ctgctgcgtc gtctgctgcg tcgtctgctg     60
cgtatgtctt atacaaaaga acaactcatg ttggcattca gctatatgag ctactatggc    120
atcactcaca caggttcagc aaaaaaaaat gctgagctca tccttaaaaa aatgaaagaa    180
gccttgaaaa catggaagcc ttttcaggaa gatgactggg aagtcgtctg ggtcctgcg    240
gtttatacca tgcctttcac aatcttcaac gatgccatga tgtatgtcat acagaagaaa    300
ggtgctgaag gggaatacgt gatagccatt cgcggcacca atccagtatc aatttcagac    360
tggctgttta atgatttcat ggtcagcgca atgaagaagt ggccttacgc atccgttgaa    420
ggccgcatac tcaaaatatc cgaaagtacc agctacggac tgaaaacctt acagaaattg    480
aagccaaaat cccatatccc cggcgaaaat aaaacgattc tgcagttcct gaatgaaaag    540
ataggcccag agggtaaagc aaaaatctgt gtaacaggcc acagtaaagg cggcgccttg    600
tcttccactc tggcactgtg gttgaaggac atccaaggag taaaactctc gcaaaacatc    660
gatatctcaa cgattccgtt tgccggacca acagccggta atgctgactt tgccgattac    720
tttgatgatt gtcttggtga tcaatgcacc cgcattgcca actcgttaga tattgtgcct    780
tatgcctgga ataaaattca ttaaaaaaac ttaaatctat atatatttct gaacaagcat    840
cagttaaacc gcttctatat caacgcgctt taatccgtgc aatgatcgca gaaactaaag    900
gtaaaaaata caagcaaatt aaggcggaaa caccaccatt agaaggcaac attaatccta    960
ttcttattga ataccttgtg caggcagcat atcagcatgt cgtcggttac ccagaattaa   1020
tgggtatgat ggatgatatt cctttaacag acatattcga agatgcgatc gcgggtttgt   1080
tataacgtgc tggtctgcag ttcccggttg gtcgtctgct gcgtcgtctg ctgcgtcgtc   1140
tgctgcgt                                                            1148
```

<210> SEQ ID NO 71
<211> LENGTH: 1076
<212> TYPE: DNA
<213> ORGANISM: Artificial Sequence
<220> FEATURE:
<223> OTHER INFORMATION: B0 - lipase M37 - B0

<400> SEQUENCE: 71

```
cgtgctggtc tgcagttccc ggttggtatg tcttatacaa aagaacaact catgttggca     60
ttcagctata tgagctacta tggcatcact cacacaggtt cagcaaaaaa aaatgctgag    120
ctcatcctta aaaaaatgaa agaagccttg aaaacatgga agccttttca ggaagatgac    180
tgggaagtcg tctggggtcc tgcggtttat accatgcctt tcacaatctt caacgatgcc    240
atgatgtatg tcatacagaa gaaaggtgct gaaggggaat acgtgatagc cattcgcggc    300
accaatccag tatcaatttc agactggctg tttaatgatt tcatggtcag cgcaatgaag    360
aagtggcctt acgcatccgt tgaaggccgc atactcaaaa tatccgaaag taccagctac    420
ggactgaaaa ccttacagaa attgaagcca aaatcccata tccccggcga aaataaaacg    480
attctgcagt tcctgaatga aaagataggc ccagagggta aagcaaaaat ctgtgtaaca    540
ggccacagta aaggcggcgc cttgtcttcc actctggcac tgtggttgaa ggacatccaa    600
ggagtaaaac tctcgcaaaa catcgatatc tcaacgattc cgtttgccgg accaacagcc    660
ggtaatgctg actttgccga ttactttgat gattgtcttg gtgatcaatg cacccgcatt    720
gccaactcgt tagatattgt gccttatgcc tggaataaaa ttcattaaaa aaacttaaat    780
```

```
ctatatatat ttctgaacaa gcatcagtta aaccgcttct atatcaacgc gctttaatcc    840
gtgcaatgat cgcagaaact aaaggtaaaa aatacaagca aattaaggcg gaaacaccac    900
cattagaagg caacattaat cctattctta ttgaatacct tgtgcaggca gcatatcagc    960
atgtcgtcgg ttacccagaa ttaatgggta tgatggatga tattcctttta acagacatat   1020 tcgaagatgc gatcgcgggt ttgttataac gtgctggtct gcagttcccg gttggt        1076
```

<210> SEQ ID NO 72
<211> LENGTH: 1136
<212> TYPE: DNA
<213> ORGANISM: Artificial Sequence
<220> FEATURE:
<223> OTHER INFORMATION: Paracin I - lipase M37 - Paracin I

<400> SEQUENCE: 72

```
aaaggaagag gcaaacaggg aggcaaggtg cgtgcgaagg caaagacacg ttcatccatg     60
tcttatacaa agaacaact catgttggca ttcagctata tgagctacta tggcatcact    120
cacacaggtt cagcaaaaaa aaatgctgag ctcatcctta aaaaaatgaa agaagccttg    180
aaaacatgga agccttttca ggaagatgac tgggaagtcg tctggggtcc tgcggtttat    240
accatgcctt tcacaatctt caacgatgcc atgatgtatg tcatacagaa gaaaggtgct    300
gaaggggaat acgtgatagc cattcgcggc accaatccag tatcaatttc agactggctg    360
tttaatgatt tcatggtcag cgcaatgaag aagtggcctt acgcatccgt tgaaggccgc    420
atactcaaaa tatccgaaag taccagctac ggactgaaaa ccttacagaa attgaagcca    480
aaatcccata tccccggcga aaataaaacg attctgcagt tcctgaatga aagataggc     540 ccagagggta aagcaaaaat ctgtgtaaca ggccacagta aaggcggcgc cttgtcttcc    600
actctggcac tgtggttgaa ggacatccaa ggagtaaaac tctcgcaaaa catcgatatc    660
tcaacgattc cgtttgccgg accaacagcc ggtaatgctg actttgccga ttactttgat    720
gattgtcttg gtgatcaatg cacccgcatt gccaactcgt tagatattgt gccttatgcc    780
tggaataaaa ttcattaaaa aaacttaaat ctatatatat ttctgaacaa gcatcagtta   840
aaccgcttct atatcaacgc gctttaatcc gtgcaatgat cgcagaaact aaaggtaaaa    900
aatacaagca aattaaggcg gaaacaccac cattagaagg caacattaat cctattctta    960
ttgaatacct tgtgcaggca gcatatcagc atgtcgtcgg ttacccagaa ttaatgggta   1020
tgatggatga tattcctttta acagacatat tcgaagatgc gatcgcgggt ttgttataaa   1080
aaggaagagg caaacaggga ggcaaggtgc gtgcgaaggc aaagacacgt tcatcc        1136
```

<210> SEQ ID NO 73
<211> LENGTH: 1136
<212> TYPE: DNA
<213> ORGANISM: Artificial Sequence
<220> FEATURE:
<223> OTHER INFORMATION: NKC - lipase M37 - NKC

<400> SEQUENCE: 73

```
gcgccgaaag cgatgaaact gttgaagaaa ttgctgaaat tacagaaaaa aggcattatg     60
tcttatacaa agaacaact catgttggca ttcagctata tgagctacta tggcatcact    120
cacacaggtt cagcaaaaaa aaatgctgag ctcatcctta aaaaaatgaa agaagccttg    180
aaaacatgga agccttttca ggaagatgac tgggaagtcg tctggggtcc tgcggtttat    240
accatgcctt tcacaatctt caacgatgcc atgatgtatg tcatacagaa gaaaggtgct    300
```

```
gaaggggaat acgtgatagc cattcgcggc accaatccag tatcaatttc agactggctg    360
tttaatgatt tcatggtcag cgcaatgaag aagtggcctt acgcatccgt tgaaggccgc    420
atactcaaaa tatccgaaag taccagctac ggactgaaaa ccttacagaa attgaagcca    480
aaatcccata tccccggcga aaataaaacg attctgcagt tcctgaatga aaagataggc    540
ccagagggta aagcaaaaat ctgtgtaaca ggccacagta aaggcggcgc cttgtcttcc    600
actctggcac tgtggttgaa ggacatccaa ggagtaaaac tctcgcaaaa catcgatatc    660
tcaacgattc cgtttgccgg accaacagcc ggtaatgctg actttgccga ttactttgat    720
gattgtcttg gtgatcaatg cacccgcatt gccaactcgt tagatattgt gccttatgcc    780
tggaataaaa ttcattaaaa aaacttaaat ctatatatat ttctgaacaa gcatcagtta    840
aaccgcttct atatcaacgc gctttaatcc gtgcaatgat cgcagaaact aaaggtaaaa    900
aatacaagca aattaaggcg gaaacaccac cattagaagg caacattaat cctattctta    960
ttgaatacct tgtgcaggca gcatatcagc atgtcgtcgg ttacccagaa ttaatgggta   1020
tgatggatga tattccttta acagacatat tcgaagatgc gatcgcgggt ttgttataag   1080
cgccgaaagc gatgaaactg ttgaagaaat tgctgaaatt acagaaaaaa ggcatt       1136
```

<210> SEQ ID NO 74
<211> LENGTH: 1136
<212> TYPE: DNA
<213> ORGANISM: Artificial Sequence
<220> FEATURE:
<223> OTHER INFORMATION: NRC - lipase M37 - NRC

<400> SEQUENCE: 74

```
gcgccgaaag cgatgcgtct gttgcgtcgc ttgctgcgtt tacagaaaaa aggcattatg     60
tcttatacaa aagaacaact catgttggca ttcagctata tgagctacta tggcatcact    120
cacacaggtt cagcaaaaaa aaatgctgag ctcatcctta aaaaaatgaa agaagccttg    180
aaaacatgga agccttttca ggaagatgac tgggaagtcg tctggggtcc tgcggtttat    240
accatgcctt tcacaatctt caacgatgcc atgatgtatg tcatacagaa gaaaggtgct    300
gaaggggaat acgtgatagc cattcgcggc accaatccag tatcaatttc agactggctg    360
tttaatgatt tcatggtcag cgcaatgaag aagtggcctt acgcatccgt tgaaggccgc    420
atactcaaaa tatccgaaag taccagctac ggactgaaaa ccttacagaa attgaagcca    480
aaatcccata tccccggcga aaataaaacg attctgcagt tcctgaatga aaagataggc    540
ccagagggta aagcaaaaat ctgtgtaaca ggccacagta aaggcggcgc cttgtcttcc    600
actctggcac tgtggttgaa ggacatccaa ggagtaaaac tctcgcaaaa catcgatatc    660
tcaacgattc cgtttgccgg accaacagcc ggtaatgctg actttgccga ttactttgat    720
gattgtcttg gtgatcaatg cacccgcatt gccaactcgt tagatattgt gccttatgcc    780
tggaataaaa ttcattaaaa aaacttaaat ctatatatat ttctgaacaa gcatcagtta    840
aaccgcttct atatcaacgc gctttaatcc gtgcaatgat cgcagaaact aaaggtaaaa    900
aatacaagca aattaaggcg gaaacaccac cattagaagg caacattaat cctattctta    960
ttgaatacct tgtgcaggca gcatatcagc atgtcgtcgg ttacccagaa ttaatgggta   1020
tgatggatga tattccttta acagacatat tcgaagatgc gatcgcgggt ttgttataag   1080
cgccgaaagc gatgcgtctg ttgcgtcgct tgctgcgttt acagaaaaaa ggcatt       1136
```

<210> SEQ ID NO 75
<211> LENGTH: 24

<212> TYPE: DNA
<213> ORGANISM: Artificial Sequence
<220> FEATURE:
<223> OTHER INFORMATION: primer pET16-L

<400> SEQUENCE: 75
cgtagaggat cgagatctcg atcc                                    24

<210> SEQ ID NO 76
<211> LENGTH: 60
<212> TYPE: DNA
<213> ORGANISM: Artificial Sequence
<220> FEATURE:
<223> OTHER INFORMATION: primer pET-R(Par)

<400> SEQUENCE: 76
gccttcgcac gcaccttgcc tccctgtttg cctcttcctt tacgaccttc gatatggccg    60

<210> SEQ ID NO 77
<211> LENGTH: 62
<212> TYPE: DNA
<213> ORGANISM: Artificial Sequence
<220> FEATURE:
<223> OTHER INFORMATION: primer TliA-rev(Par)

<400> SEQUENCE: 77
gggaggcaag gtgcgtgcga aggcaaagac acgttcatcc ggtgtatttg actacaagaa    60
cc                                                                  62

<210> SEQ ID NO 78
<211> LENGTH: 35
<212> TYPE: DNA
<213> ORGANISM: Artificial Sequence
<220> FEATURE:
<223> OTHER INFORMATION: primer NdeI-TliA-for

<400> SEQUENCE: 78
cttaaggcat atgtcaactg atcagcacac cctcg                              35

<210> SEQ ID NO 79
<211> LENGTH: 60
<212> TYPE: DNA
<213> ORGANISM: Artificial Sequence
<220> FEATURE:
<223> OTHER INFORMATION: primer pET-R(Buf)

<400> SEQUENCE: 79
cgacgcagca gacgaccaac cgggaactgc agaccagcac gacgaccttc gatatggccg    60

<210> SEQ ID NO 80
<211> LENGTH: 68
<212> TYPE: DNA
<213> ORGANISM: Artificial Sequence
<220> FEATURE:
<223> OTHER INFORMATION: primer TliA-rev(Buf)

<400> SEQUENCE: 80
cccggttggt cgtctgctgc gtcgtctgct gcgtcgtctg ctgcgtggtg tatttgacta    60
caagaacc                                                            68

<210> SEQ ID NO 81
<211> LENGTH: 44
<212> TYPE: DNA
<213> ORGANISM: Artificial Sequence
<220> FEATURE:

<223> OTHER INFORMATION: primer pET-R(B0)

<400> SEQUENCE: 81
caaccgggaa ctgcagacca gcacgacgac cttcgatatg gccg        44

<210> SEQ ID NO 82
<211> LENGTH: 46
<212> TYPE: DNA
<213> ORGANISM: Artificial Sequence
<220> FEATURE:
<223> OTHER INFORMATION: primer TliA-rev(B0)

<400> SEQUENCE: 82
gctggtctgc agttcccggt tggtggtgta tttgactaca agaacc        46

<210> SEQ ID NO 83
<211> LENGTH: 19
<212> TYPE: DNA
<213> ORGANISM: Artificial Sequence
<220> FEATURE:
<223> OTHER INFORMATION: primer pET-R(con)

<400> SEQUENCE: 83
acgaccttcg atatggccg        19

<210> SEQ ID NO 84
<211> LENGTH: 41
<212> TYPE: DNA
<213> ORGANISM: Artificial Sequence
<220> FEATURE:
<223> OTHER INFORMATION: primer TliA-rev(con)

<400> SEQUENCE: 84
cggccatatc gaaggtcgtg gtgtatttga ctacaagaac c        41

<210> SEQ ID NO 85
<211> LENGTH: 68
<212> TYPE: DNA
<213> ORGANISM: Artificial Sequence
<220> FEATURE:
<223> OTHER INFORMATION: primer M37-rev(Buf)

<400> SEQUENCE: 85
cccggttggt cgtctgctgc gtcgtctgct gcgtcgtctg ctgcgtgcat ctccacgcgc        60
caatgatg        68

<210> SEQ ID NO 86
<211> LENGTH: 35
<212> TYPE: DNA
<213> ORGANISM: Artificial Sequence
<220> FEATURE:
<223> OTHER INFORMATION: primer Nde-M37-for

<400> SEQUENCE: 86
cttaaggcat atgttataac aaacccgcga tcgca        35

<210> SEQ ID NO 87
<211> LENGTH: 62
<212> TYPE: DNA
<213> ORGANISM: Artificial Sequence
<220> FEATURE:
<223> OTHER INFORMATION: primer M37-rev(Par)

<400> SEQUENCE: 87
gggaggcaag gtgcgtgcga aggcaaagac acgttcatcc gcatctccac gcgccaatga        60

```
                                                    tg                                                              62

<210> SEQ ID NO 88
<211> LENGTH: 46
<212> TYPE: DNA
<213> ORGANISM: Artificial Sequence
<220> FEATURE:
<223> OTHER INFORMATION: primer M37-rev(B0)

<400> SEQUENCE: 88
gctggtctgc agttcccggt tggtgcatct ccacgcgcca atgatg                  46

<210> SEQ ID NO 89
<211> LENGTH: 62
<212> TYPE: DNA
<213> ORGANISM: Artificial Sequence
<220> FEATURE:
<223> OTHER INFORMATION: primer M37-rev(NKC)

<400> SEQUENCE: 89
actgttgaag aaattgctga aattacagaa aaaaggcatt gcatctccac gcgccaatga   60
tg                                                                  62

<210> SEQ ID NO 90
<211> LENGTH: 62
<212> TYPE: DNA
<213> ORGANISM: Artificial Sequence
<220> FEATURE:
<223> OTHER INFORMATION: primer M37-rev(NRC)

<400> SEQUENCE: 90
tctgttgcgt cgcttgctgc gtttacagaa aaaaggcatt gcatctccac gcgccaatga   60
tg                                                                  62

<210> SEQ ID NO 91
<211> LENGTH: 42
<212> TYPE: DNA
<213> ORGANISM: Artificial Sequence
<220> FEATURE:
<223> OTHER INFORMATION: primer M37-rev(con)

<400> SEQUENCE: 91
gcagcggcca tatcgaaggt cgtgcatctc cacgcgccaa tg                      42
```